US009585657B2

(12) United States Patent
Shelton, IV et al.

(10) Patent No.: US 9,585,657 B2
(45) Date of Patent: Mar. 7, 2017

(54) ACTUATOR FOR RELEASING A LAYER OF MATERIAL FROM A SURGICAL END EFFECTOR

(71) Applicant: Ethicon Endo-Surgery, Inc., Cincinnati, OH (US)

(72) Inventors: Frederick E. Shelton, IV, Hillsboro, OH (US); Jerome R. Morgan, Cincinnati, OH (US); Jeffrey S. Swayze, Hamilton, OH (US); Michael J. Vendely, Lebanon, OH (US); Taylor W. Aronhalt, Loveland, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1029 days.

(21) Appl. No.: 13/763,177

(22) Filed: Feb. 8, 2013

(65) Prior Publication Data

US 2013/0146641 A1  Jun. 13, 2013

Related U.S. Application Data

(63) Continuation-in-part of application No. 12/032,002, filed on Feb. 15, 2008, now Pat. No. 8,371,491.

(51) Int. Cl.
*A61B 17/068* (2006.01)
*A61B 17/072* (2006.01)

(52) U.S. Cl.
CPC .......... *A61B 17/068* (2013.01); *A61B 17/072* (2013.01); *A61B 17/07292* (2013.01)

(58) Field of Classification Search
CPC ............ A61B 17/068; A61B 17/07292; A61B 17/072

(Continued)

(56) References Cited

U.S. PATENT DOCUMENTS

| 60,052 A | 6/1867 | Smith |
| 662,587 A | 11/1900 | Blake |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

U.S. Appl. No. 13/763,021, filed Feb. 8, 2013.

(Continued)

*Primary Examiner* — Thanh Truong
*Assistant Examiner* — Dianne Mitchell

(57) ABSTRACT

An end effector assembly for use with a surgical instrument. The end effector assembly can comprise an anvil, a fastener cartridge including fastener cavities, fasteners removably positioned in the fastener cavities, a piece of buttress material releasably secured intermediate the anvil and the fastener cartridge, a connector, and an actuator configured to overcome the connector when actuated. The connector can secure the piece of buttress material relative to the anvil or the fastener cartridge at a location that is distal to at least one fastener cavity. The actuator can overcome the connector prior to the removal of the fasteners from the fastener cavities. Further, the actuator can extend past the fasteners in the fastener cavities, and can be actuated proximal to the fastener cavities.

20 Claims, 59 Drawing Sheets

(58) Field of Classification Search
USPC .................................. 227/175.1, 176.1, 180.1
See application file for complete search history.

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Siegel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |

(56) References Cited

U.S. PATENT DOCUMENTS

| | | |
|---|---|---|
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |

(56) References Cited

U.S. PATENT DOCUMENTS

| | | |
|---|---|---|
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,343,391 A | 8/1994 | Mushabac |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |

(56) References Cited

U.S. PATENT DOCUMENTS

| | | |
|---|---|---|
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A * | 8/1996 | McKean ......... A61B 17/07207 227/178.1 |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |

(56) References Cited

U.S. PATENT DOCUMENTS

| | | |
|---|---|---|
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |

(56) References Cited

U.S. PATENT DOCUMENTS

| | | |
|---|---|---|
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A * | 5/1999 | Frater .............. A61B 17/07207 606/148 |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Törmäläet al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |

(56) References Cited

U.S. PATENT DOCUMENTS

| | | |
|---|---|---|
| 6,056,735 A | 5/2000 | Okada et al. |
| 6,056,746 A | 5/2000 | Goble et al. |
| 6,062,360 A | 5/2000 | Shields |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,106,511 A | 8/2000 | Jensen |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,430,298 B1 | 8/2002 | Kettl et al. |

(56) References Cited

U.S. PATENT DOCUMENTS

| | | |
|---|---|---|
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 * | 12/2003 | Grant .................. A61B 17/072 227/175.1 |
| 6,663,623 B1 | 12/2003 | Oyama et al. |
| 6,663,641 B1 | 12/2003 | Kovac et al. |
| 6,666,854 B2 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |

(56) References Cited

U.S. PATENT DOCUMENTS

| | | |
|---|---|---|
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,025,743 B2 | 4/2006 | Mann et al. |
| 7,029,435 B2 | 4/2006 | Nakao |
| 7,029,439 B2 | 4/2006 | Roberts et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |

(56) References Cited

U.S. PATENT DOCUMENTS

| | | |
|---|---|---|
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,980 B2 | 11/2006 | Buysse et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |

(56) References Cited

U.S. PATENT DOCUMENTS

| | | |
|---|---|---|
| 7,306,597 B2 | 12/2007 | Manzo |
| 7,308,998 B2 | 12/2007 | Mastri et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |

(56) References Cited

U.S. PATENT DOCUMENTS

| | | |
|---|---|---|
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |

(56) References Cited

U.S. PATENT DOCUMENTS

| | | |
|---|---|---|
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scircia |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |

(56) References Cited

U.S. PATENT DOCUMENTS

| | | |
|---|---|---|
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,079,950 B2 | 12/2011 | Stern et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,286,845 B2 | 10/2012 | Perry et al. |
| 8,287,561 B2 | 10/2012 | Nunez et al. |
| 8,292,150 B2 | 10/2012 | Bryant |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |

(56) References Cited

U.S. PATENT DOCUMENTS

| | | |
|---|---|---|
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,574,199 B2 | 11/2013 | von Bülow et al. |
| 8,579,176 B2 | 11/2013 | Smith et al. |
| 8,579,178 B2 | 11/2013 | Holsten et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |

(56) References Cited

U.S. PATENT DOCUMENTS

| | | |
|---|---|---|
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,746,529 B2 | 6/2014 | Shelton, IV et al. |
| 8,746,530 B2 | 6/2014 | Giordano et al. |
| 8,747,238 B2 | 6/2014 | Shelton, IV et al. |
| 8,752,264 B2 | 6/2014 | Ackley et al. |
| 8,752,747 B2 | 6/2014 | Shelton, IV et al. |
| 8,752,749 B2 | 6/2014 | Moore et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,879 B2 | 7/2014 | Shelton, IV et al. |
| 8,771,169 B2 | 7/2014 | Whitman et al. |
| 8,783,541 B2 | 7/2014 | Shelton, IV et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,807,414 B2 | 8/2014 | Ross et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,858,571 B2 | 10/2014 | Shelton, IV et al. |
| 8,858,590 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,967,443 B2 | 3/2015 | McCuen |
| 8,967,446 B2 | 3/2015 | Beardsley et al. |
| 8,968,312 B2 | 3/2015 | Marczyk et al. |
| 8,968,337 B2 | 3/2015 | Whitfield et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,955 B2 | 3/2015 | Aronhalt et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,230 B2 | 6/2015 | Morgan et al. |
| 9,050,083 B2 | 6/2015 | Yates et al. |
| 9,050,100 B2 | 6/2015 | Yates et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |

(56) References Cited

U.S. PATENT DOCUMENTS

| | | |
|---|---|---|
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,873 B2 | 8/2015 | Marczyk et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Sharbnik et al. |
| 9,138,225 B2 | 9/2015 | Huang et al. |
| 9,149,274 B2 | 10/2015 | Spivey et al. |
| 9,149,325 B2 | 10/2015 | Worrell et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,192,380 B2 | 11/2015 | (Tarinelli) Racenet et al. |
| 9,192,384 B2 | 11/2015 | Bettuchi |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,211,121 B2 | 12/2015 | Hall et al. |
| 9,211,122 B2 | 12/2015 | Hagerty et al. |
| 9,226,750 B2 | 1/2016 | Weir et al. |
| 9,226,751 B2 | 1/2016 | Shelton, IV et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,259,274 B2 | 2/2016 | Prisco |
| 9,271,799 B2 | 3/2016 | Shelton, IV et al. |
| 9,277,922 B2 | 3/2016 | Carter et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,320,520 B2 | 4/2016 | Shelton, IV et al. |
| 9,320,521 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,005 B2 | 6/2016 | Shelton, IV et al. |
| 9,364,230 B2 | 6/2016 | Shelton, IV et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0029032 A1 | 3/2002 | Arkin |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0165541 A1 | 11/2002 | Whitman |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |

(56) References Cited

U.S. PATENT DOCUMENTS

| | | |
|---|---|---|
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025816 A1* | 2/2006 | Shelton, IV ...... A61B 17/07207 606/215 |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |

(56) References Cited

U.S. PATENT DOCUMENTS

| | | |
|---|---|---|
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0134200 A1* | 5/2009 | Tarinelli .......... A61B 17/07207 227/180.1 |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247901 A1 | 10/2009 | Zimmer |
| 2009/0248038 A1 | 10/2009 | Blumenkranz et al. |
| 2009/0253959 A1 | 10/2009 | Yoshie et al. |

(56) References Cited

U.S. PATENT DOCUMENTS

| | | |
|---|---|---|
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0022032 A1 | 1/2011 | Zemlok et al. |
| 2011/0024477 A1 | 2/2011 | Hall et al. |
| 2011/0024478 A1 | 2/2011 | Shelton, Iv |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118778 A1 | 5/2011 | Burbank |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0208093 A1 | 8/2011 | Gross et al. |
| 2011/0210156 A1 | 9/2011 | Smith et al. |
| 2011/0241597 A1 | 10/2011 | Zhu et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0290851 A1 | 12/2011 | Shelton, IV |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0046692 A1 | 2/2012 | Smith et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0078071 A1 | 3/2012 | Bohm et al. |
| 2012/0078244 A1 | 3/2012 | Worrell et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |

(56) References Cited

U.S. PATENT DOCUMENTS

| | | |
|---|---|---|
| 2012/0083835 A1 | 4/2012 | Shelton, IV et al. |
| 2012/0083836 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0138660 A1 | 6/2012 | Shelton, IV |
| 2012/0160721 A1 | 6/2012 | Shelton, IV et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248167 A1 | 10/2012 | Flanagan et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0131651 A1 | 5/2013 | Strobl et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek (nee Prommersberger) et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |

(56) References Cited

U.S. PATENT DOCUMENTS

| | | |
|---|---|---|
| 2014/0005678 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0097227 A1 | 4/2014 | Aronhalt et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207166 A1 | 7/2014 | Shelton, IV et al. |
| 2014/0224857 A1 | 8/2014 | Schmid |
| 2014/0230595 A1 | 8/2014 | Butt et al. |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |

(56) References Cited

U.S. PATENT DOCUMENTS

| | | |
|---|---|---|
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |

(56) References Cited

U.S. PATENT DOCUMENTS

| | | |
|---|---|---|
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101137402 A | 3/2008 |
| CN | 101507620 A | 8/2009 |
| CN | 101507622 A | 8/2009 |
| CN | 101507623 A | 8/2009 |
| CN | 101507625 A | 8/2009 |
| CN | 101541251 A | 9/2009 |
| CN | 101675898 A | 3/2010 |
| CN | 101683280 A | 3/2010 |
| CN | 201949071 U | 8/2011 |
| CN | 101336835 B | 9/2011 |
| CN | 102188270 A | 9/2011 |
| CN | 101534723 B | 1/2012 |
| CN | 101310680 B | 4/2012 |
| CN | 101507633 B | 2/2013 |
| CN | 101023879 B | 3/2013 |
| CN | 101401736 B | 6/2013 |
| CN | 101332110 B | 7/2013 |
| CN | 101683281 B | 1/2014 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 A1 | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |

(56) References Cited

FOREIGN PATENT DOCUMENTS

| | | |
|---|---|---|
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |

(56) References Cited

FOREIGN PATENT DOCUMENTS

| | | | |
|---|---|---|---|
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 B1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A1 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A2 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 1982657 B1 | 7/2013 |
| EP | 2614782 A2 | 7/2013 |

(56) References Cited

FOREIGN PATENT DOCUMENTS

| | | |
|---|---|---|
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777538 A2 | 9/2014 |
| EP | 2446835 B1 | 1/2015 |
| EP | 2923660 A2 | 9/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 47-11908 Y1 | 5/1972 |
| JP | 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147499 A | 6/1988 |
| JP | 63-203149 A | 8/1988 |
| JP | 10-512469 A | 12/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-63054 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |

(56) References Cited

FOREIGN PATENT DOCUMENTS

| | | |
|---|---|---|
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-006137 A | 1/2009 |
| JP | 2009-502351 A | 1/2009 |
| JP | 2009-022742 A | 2/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |

(56) References Cited

FOREIGN PATENT DOCUMENTS

| | | |
|---|---|---|
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |

(56) References Cited

FOREIGN PATENT DOCUMENTS

| | | |
|---|---|---|
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/167427 A1 | 3/2013 |
| WO | WO 2013/062978 A2 | 5/2013 |
| WO | WO 2013/148762 A2 | 10/2013 |
| WO | WO 2014/004199 A1 | 1/2014 |

OTHER PUBLICATIONS

U.S. Appl. No. 13/763,037, filed Feb. 8, 2013.
European Examination Report, Application No. 14154546.7, dated Jul. 27, 2015 (5 pages).
Partial European Search Report, Application No. 09250379.6, dated Jul. 7, 2010 (7 pages).
European Search Report, Application No. 09250379.6, dated Nov. 4, 2010 (12 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

(56) References Cited

OTHER PUBLICATIONS

Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive198 Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 page).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf;
Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
U.S. Appl. No. 12/031,573, filed Feb. 14, 2008.
U.S. Appl. No. 14/633,555, filed Feb. 27, 2015.
U.S. Appl. No. 14/633,562, filed Feb. 27, 2015.
U.S. Appl. No. 14/633,576, filed Feb. 27, 2015.
U.S. Appl. No. 14/633,546, filed Feb. 27, 2015.
U.S. Appl. No. 14/633,560, filed Feb. 27, 2015.
U.S. Appl. No. 14/633,566, filed Feb. 27, 2015.
U.S. Appl. No. 14/633,542, filed Feb. 27, 2015.
U.S. Appl. No. 14/633,548, filed Feb. 27, 2015.
U.S. Appl. No. 14/633,526, filed Feb. 27, 2015.
U.S. Appl. No. 14/633,541, filed Feb. 27, 2015.

* cited by examiner

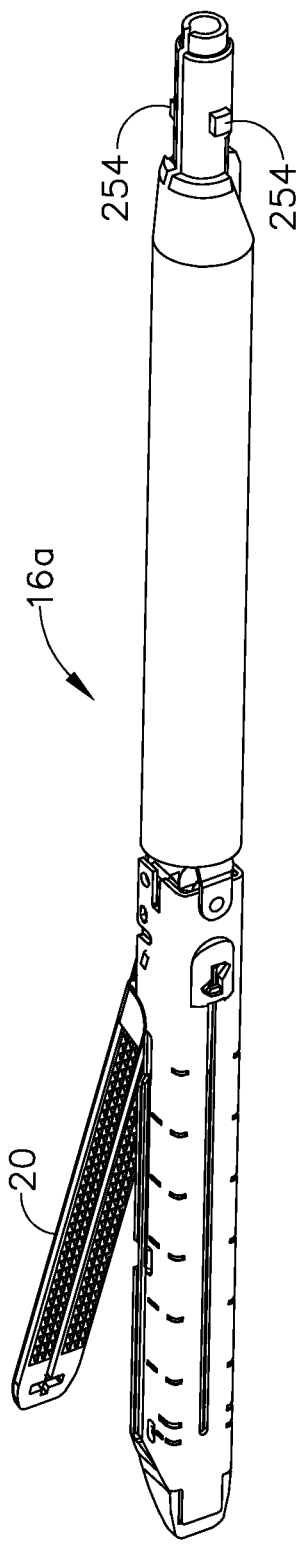
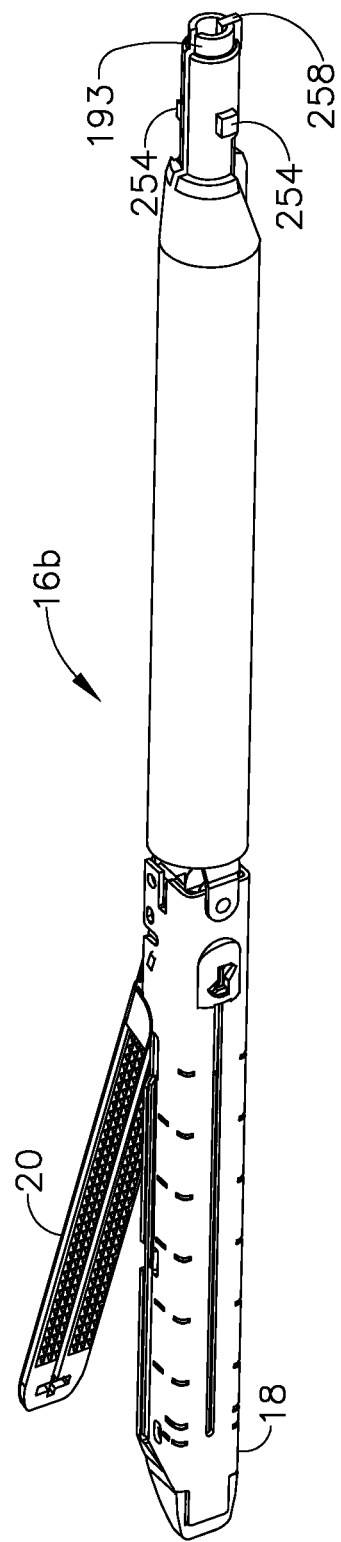

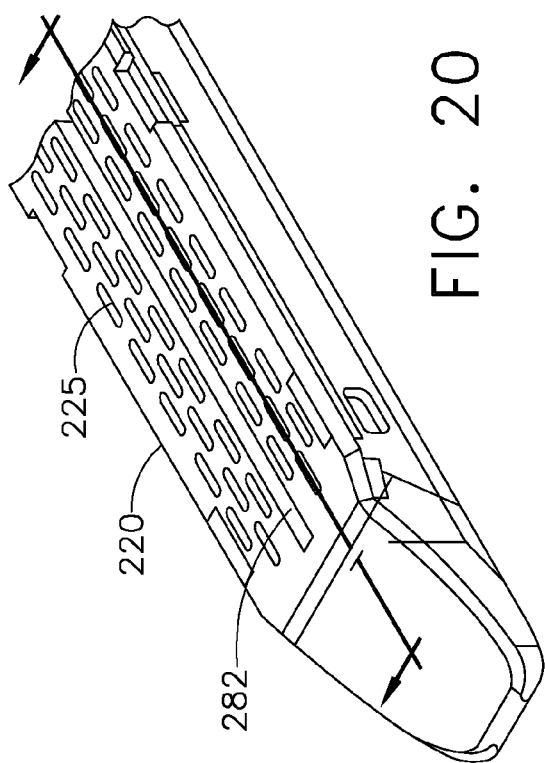
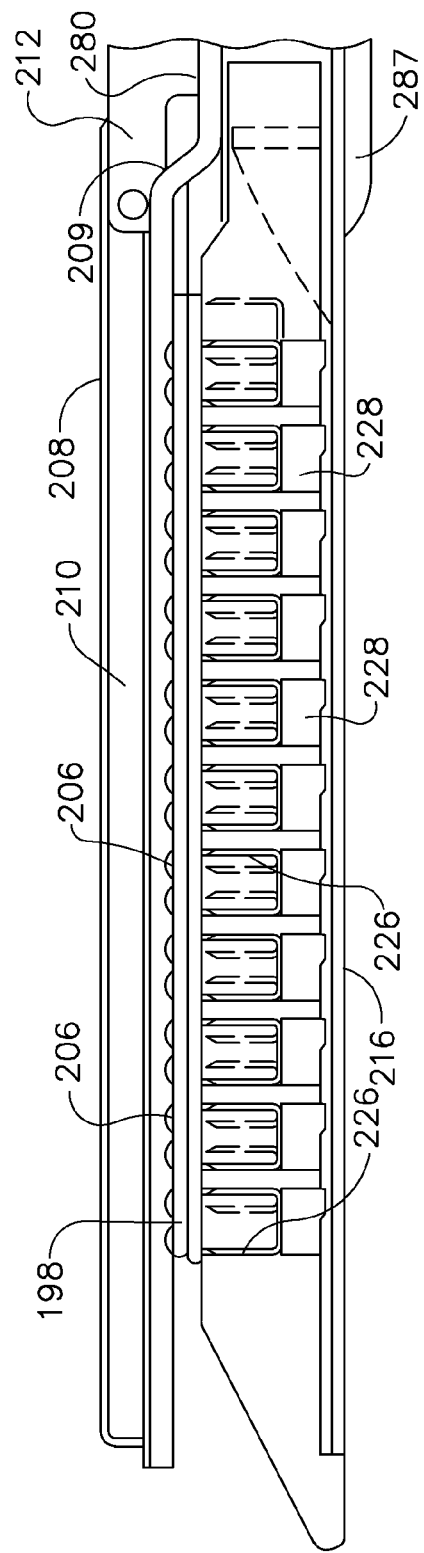
FIG. 20
FIG. 21

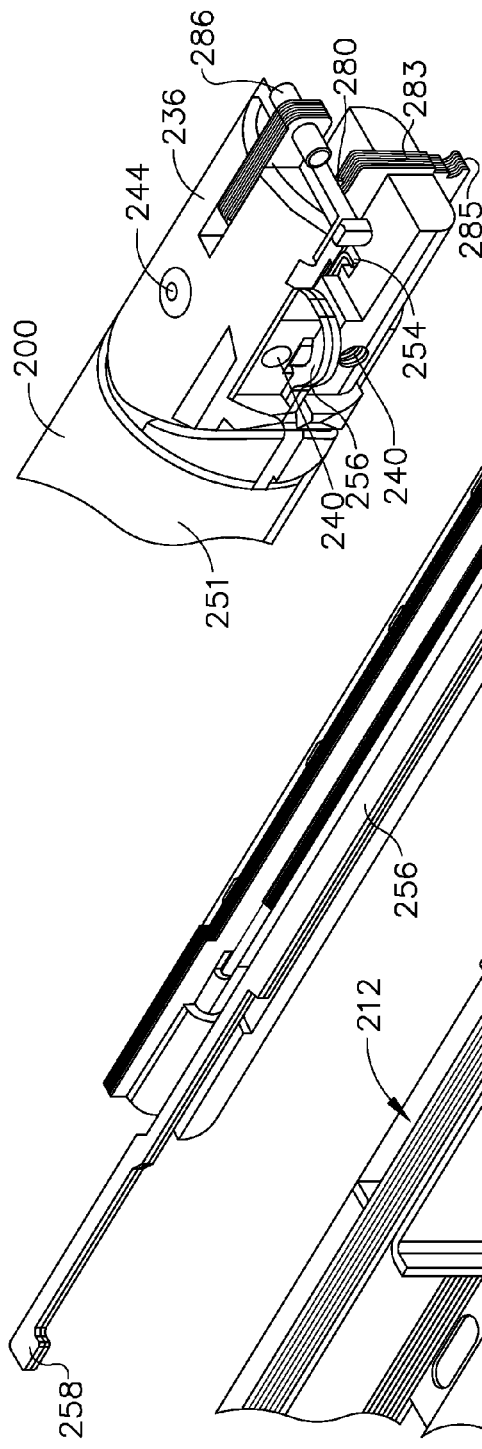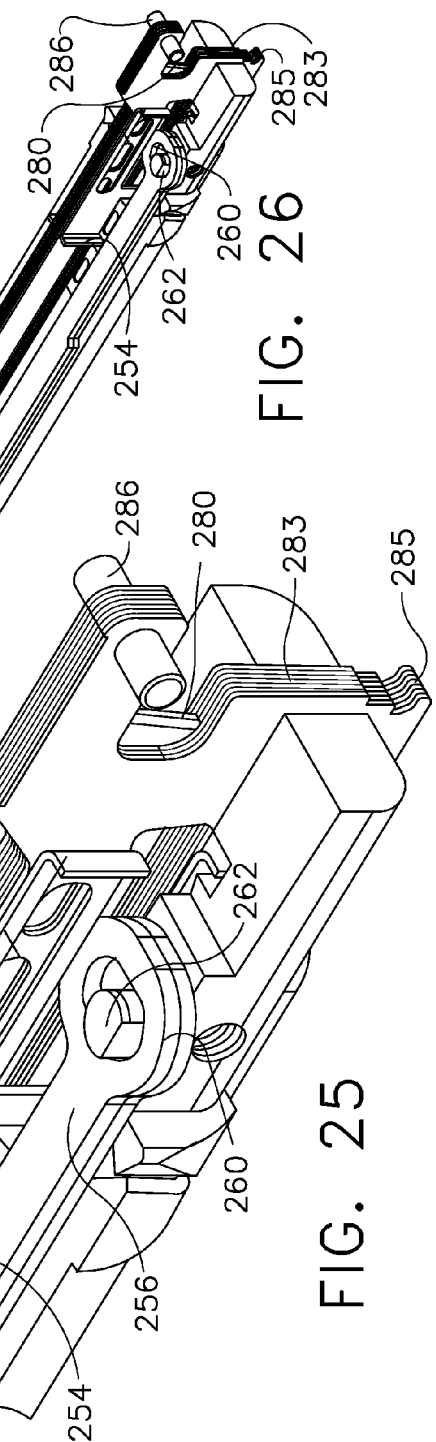

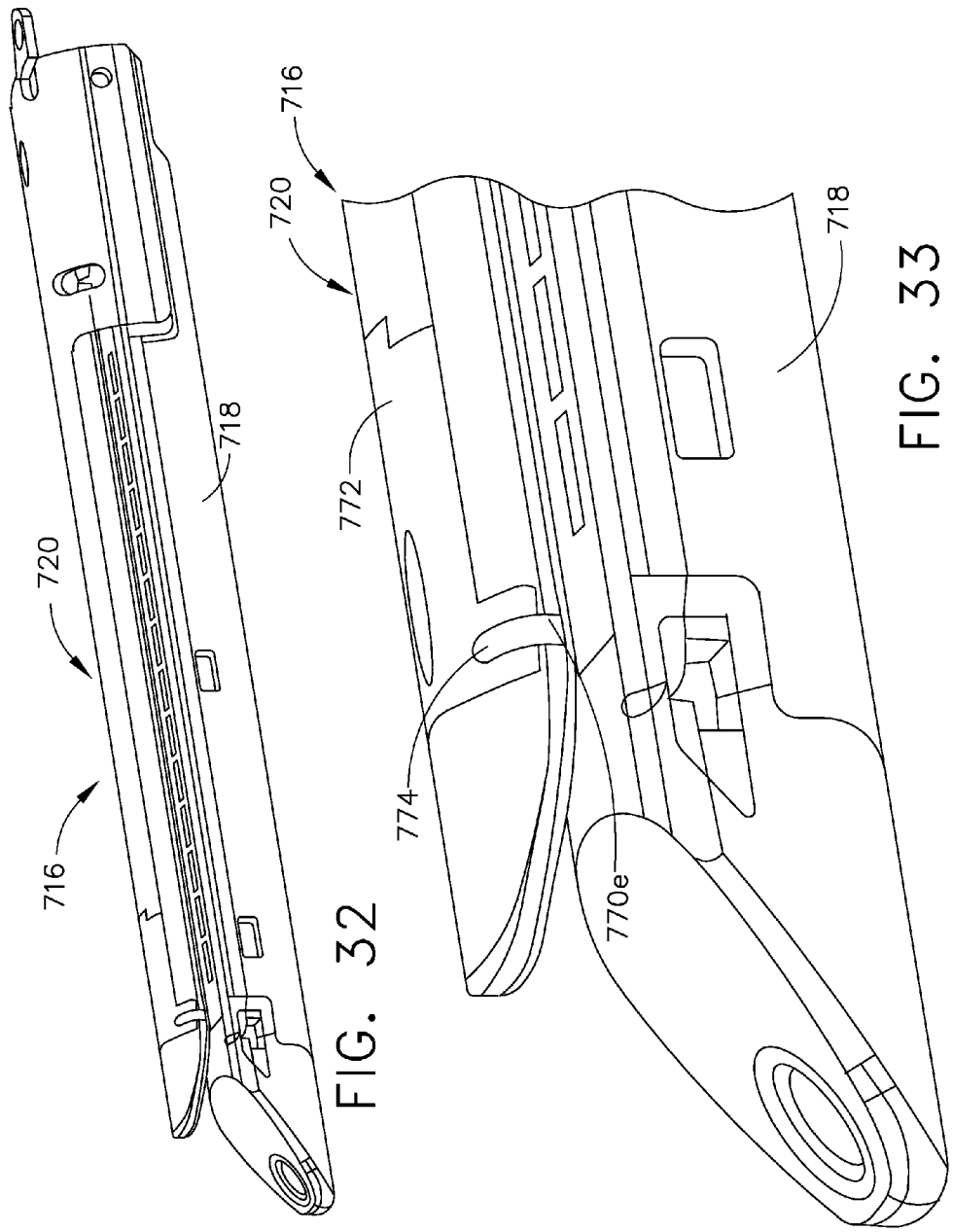

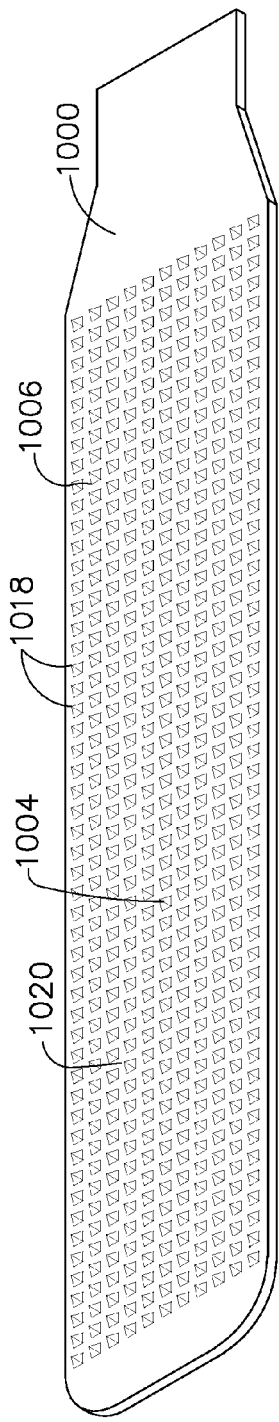
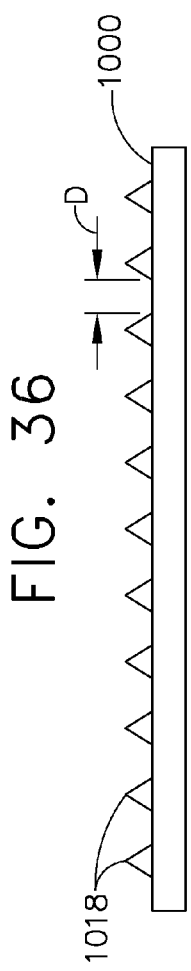
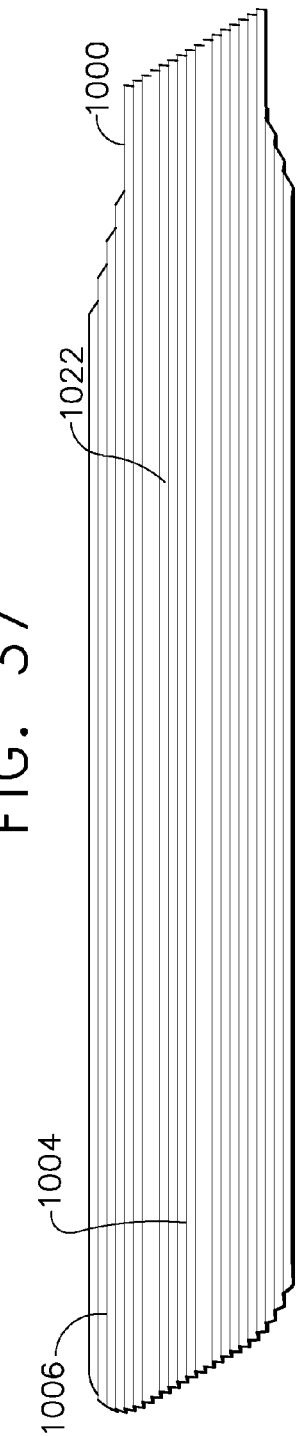
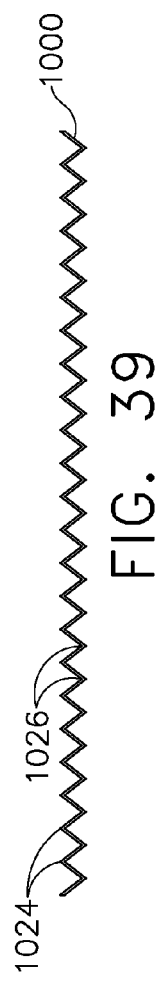
FIG. 36
FIG. 37
FIG. 38
FIG. 39

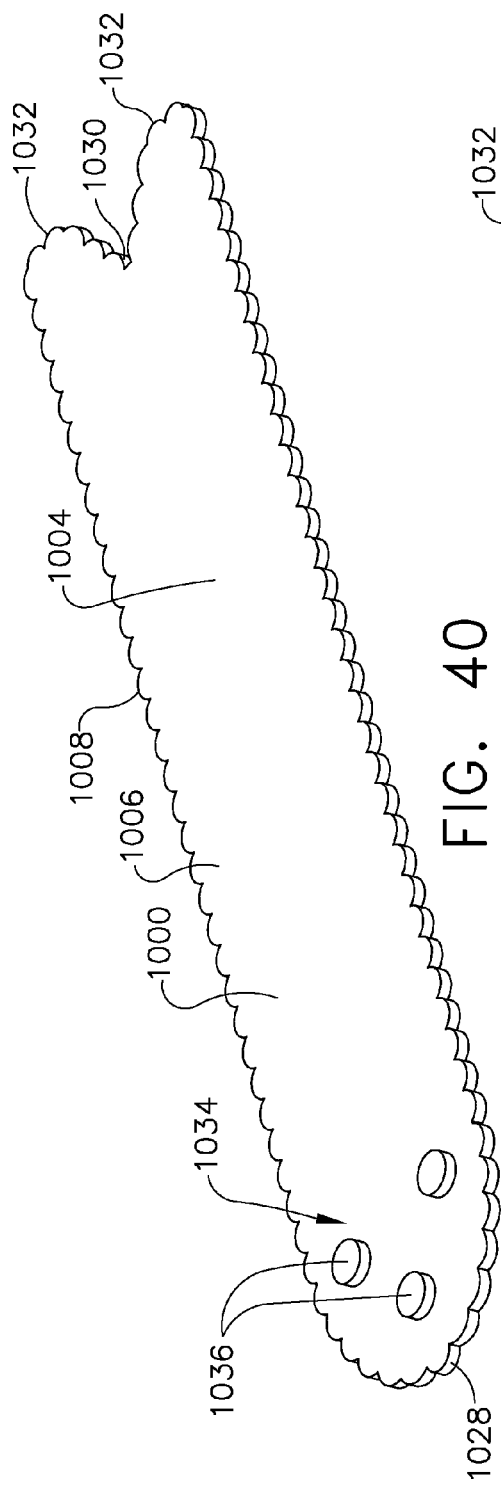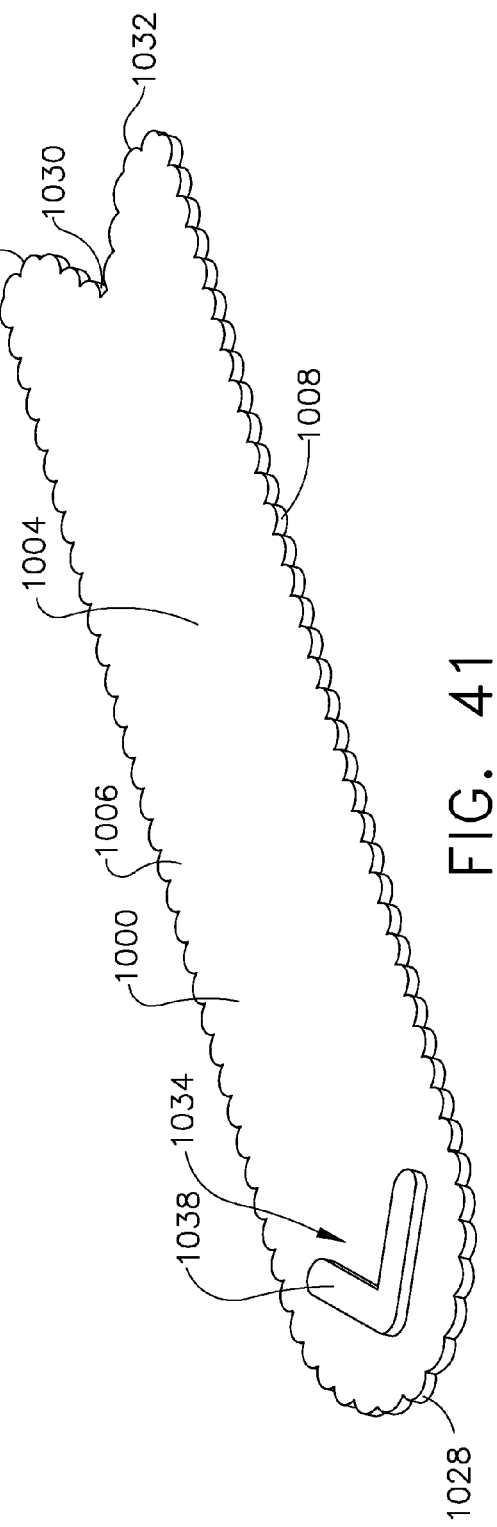

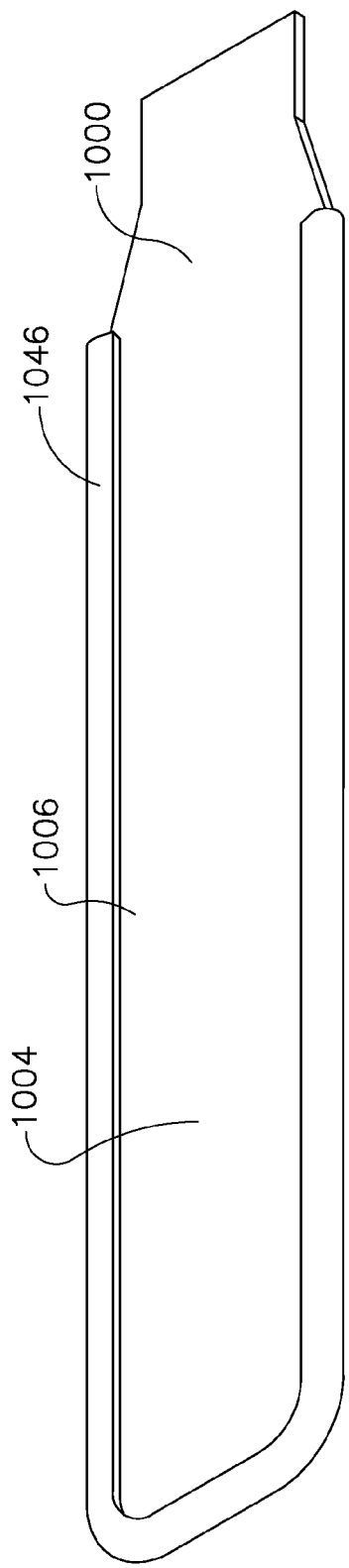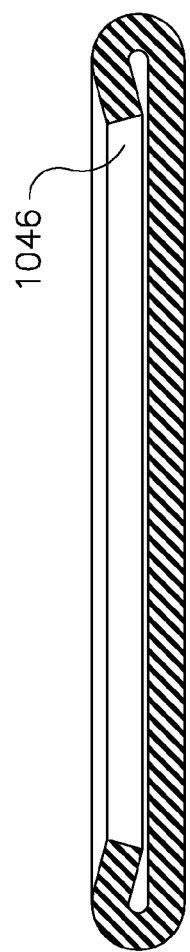
FIG. 45
FIG. 46

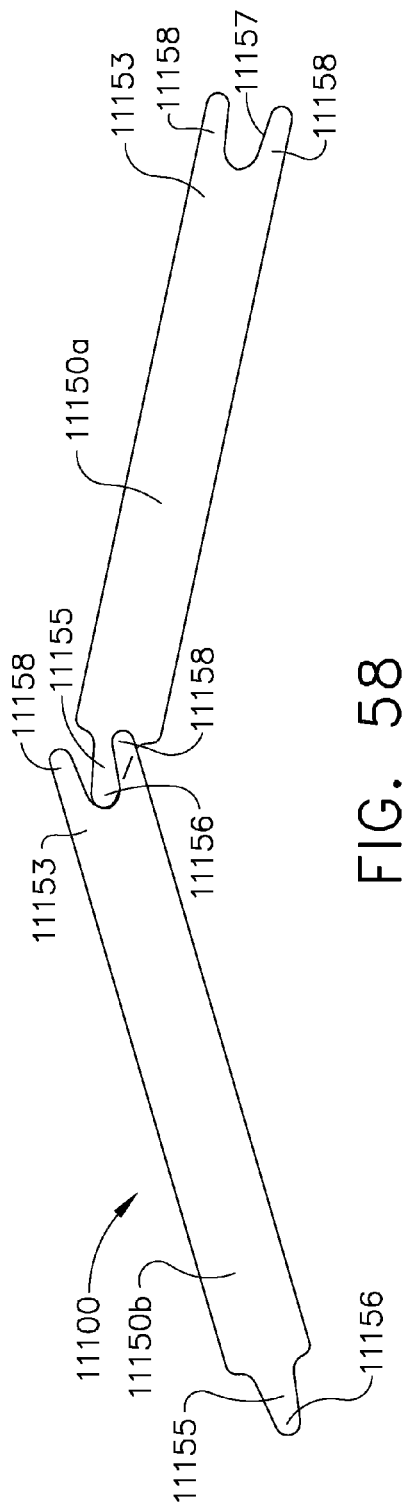
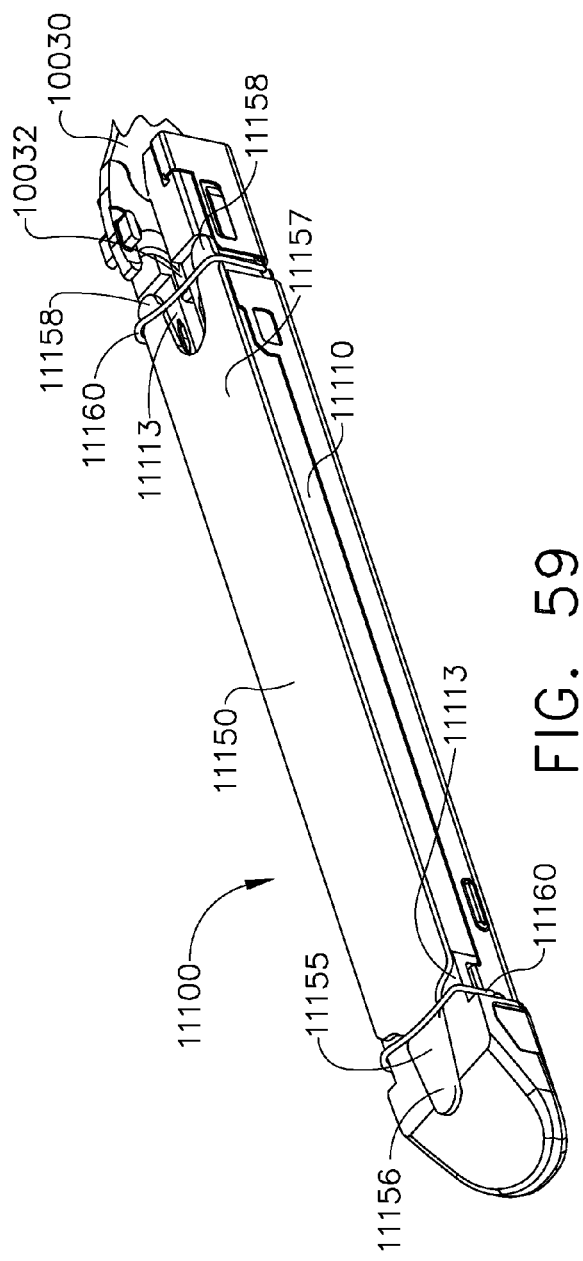
FIG. 58
FIG. 59

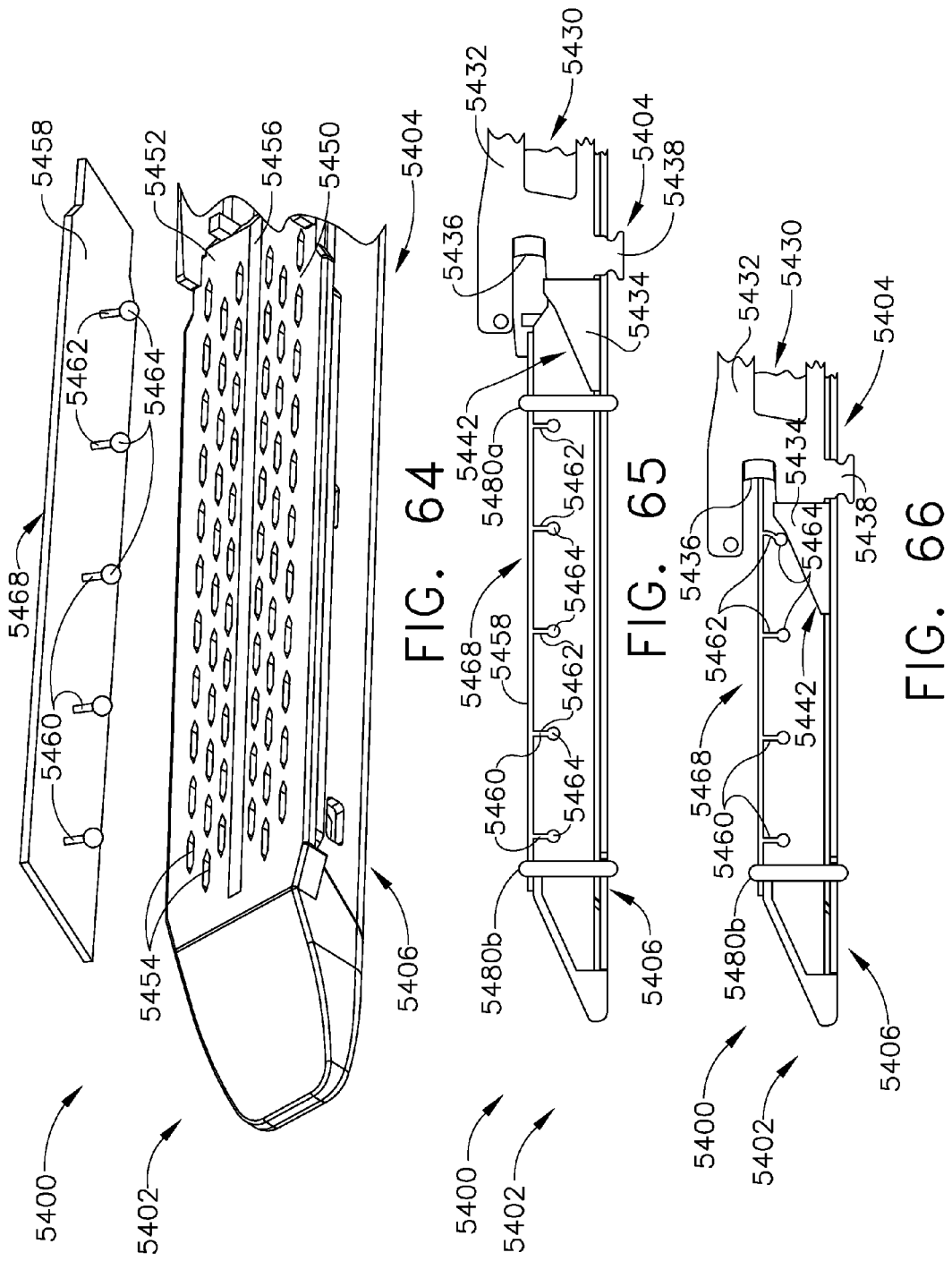

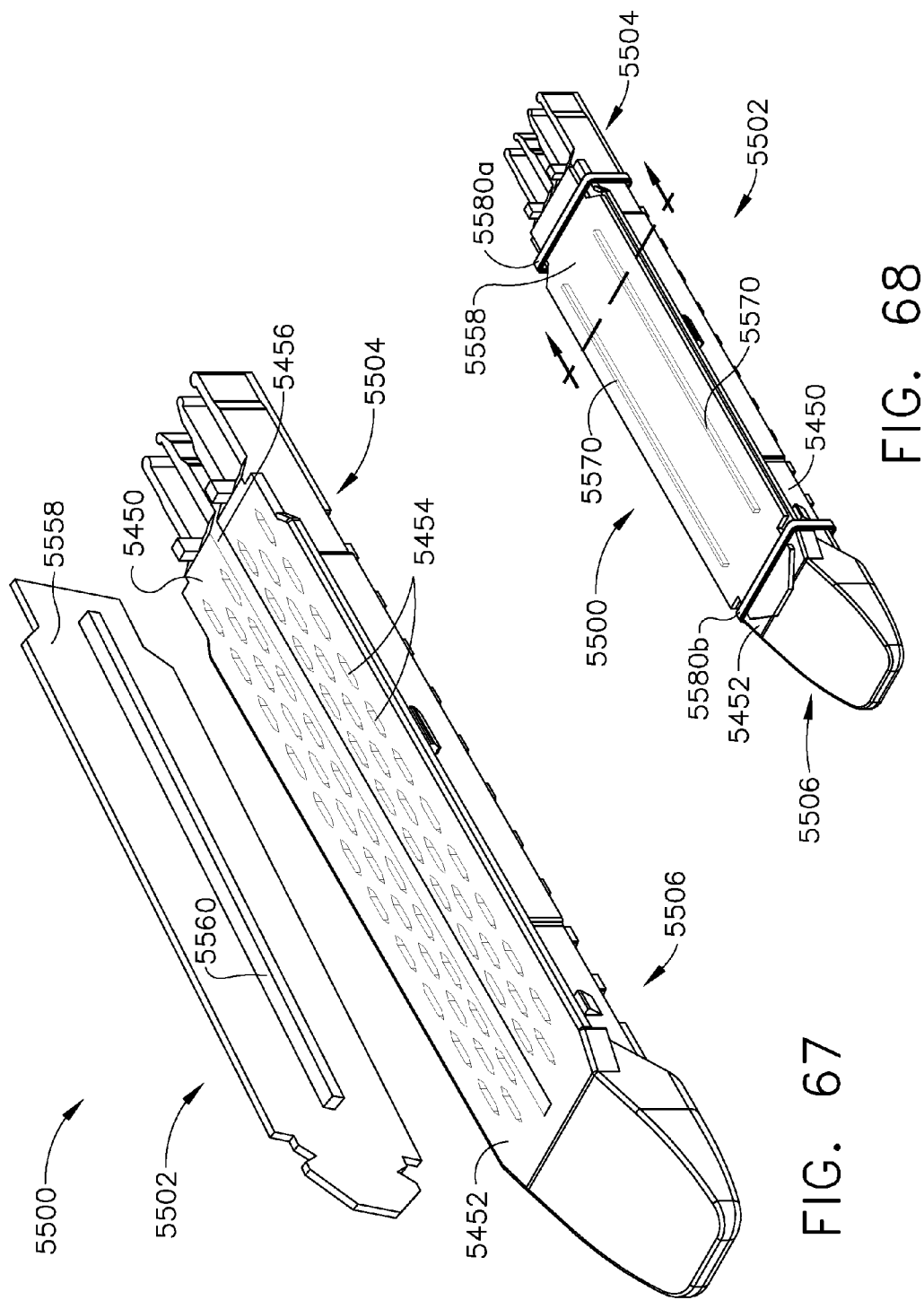

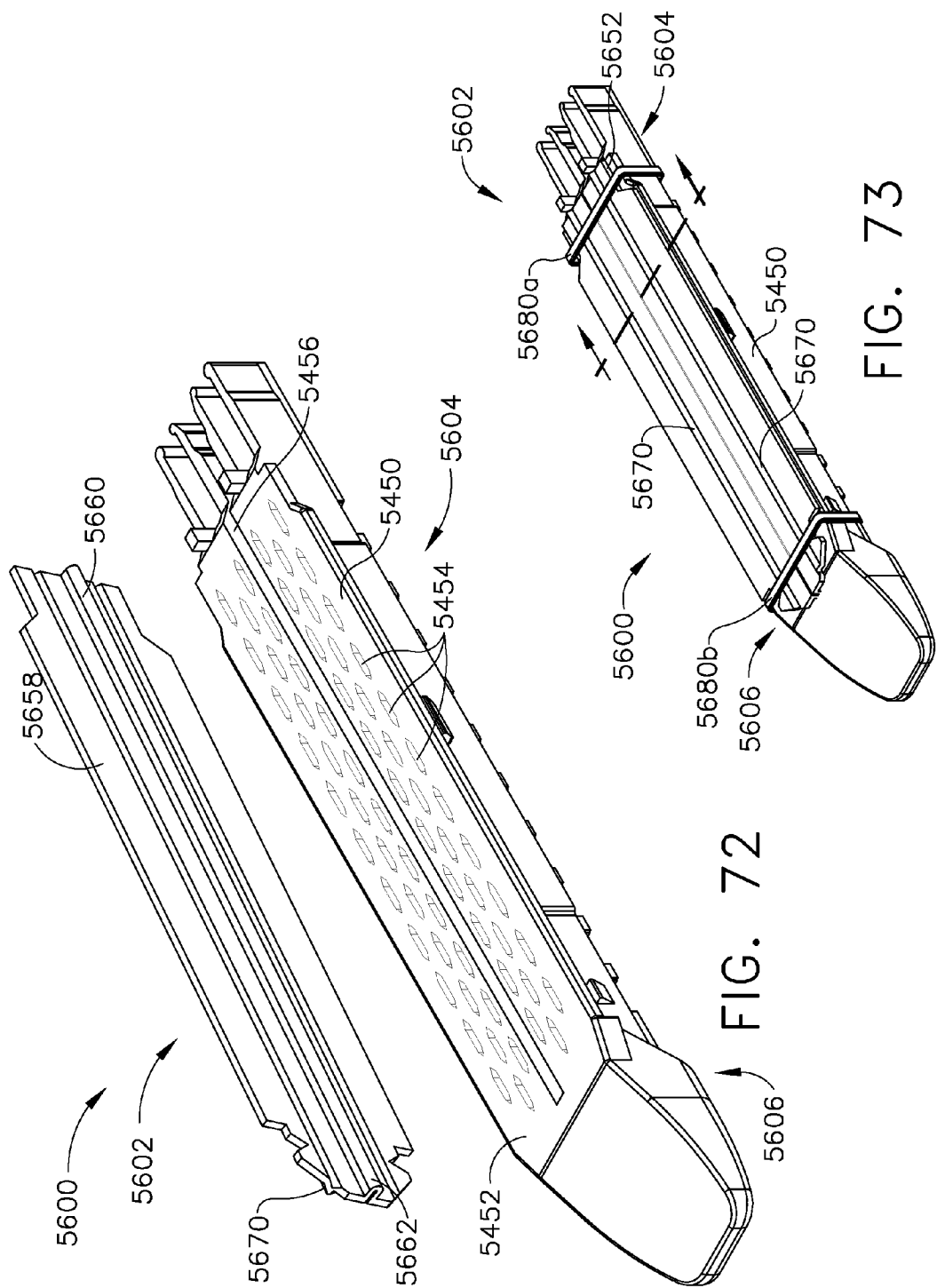

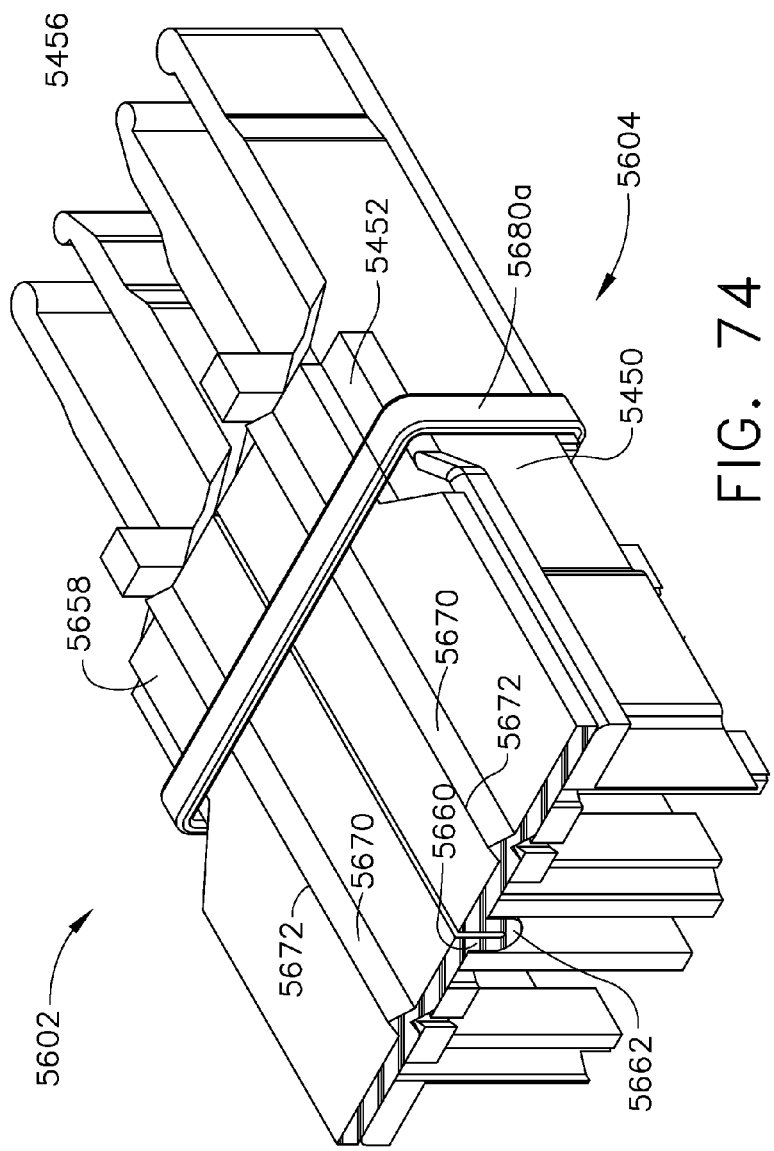
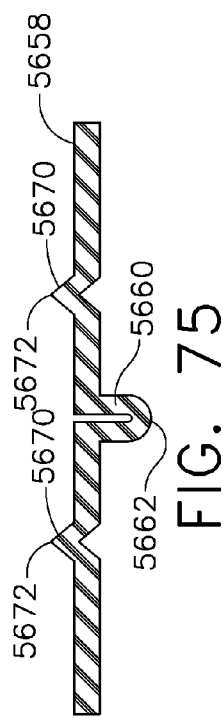

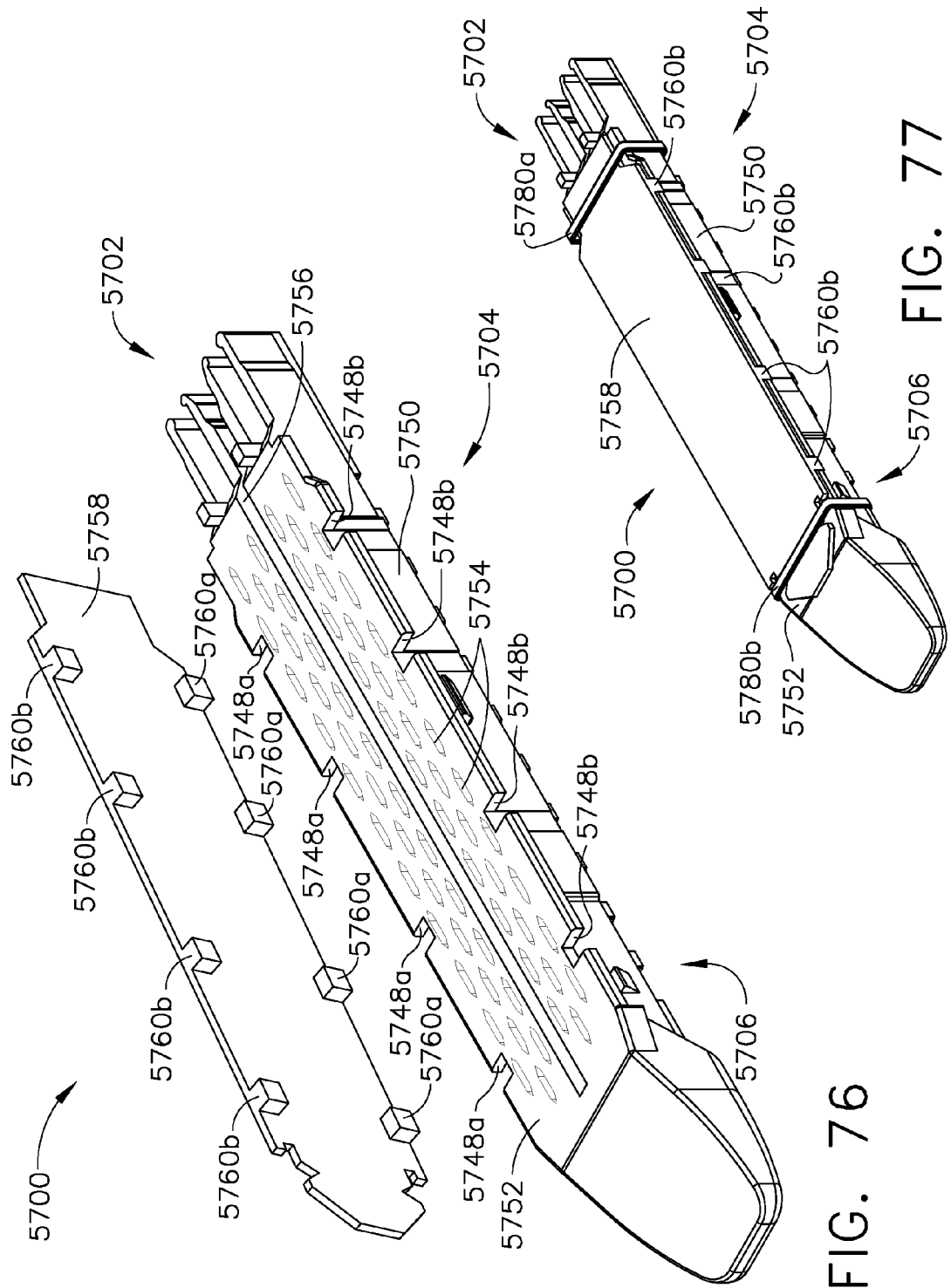

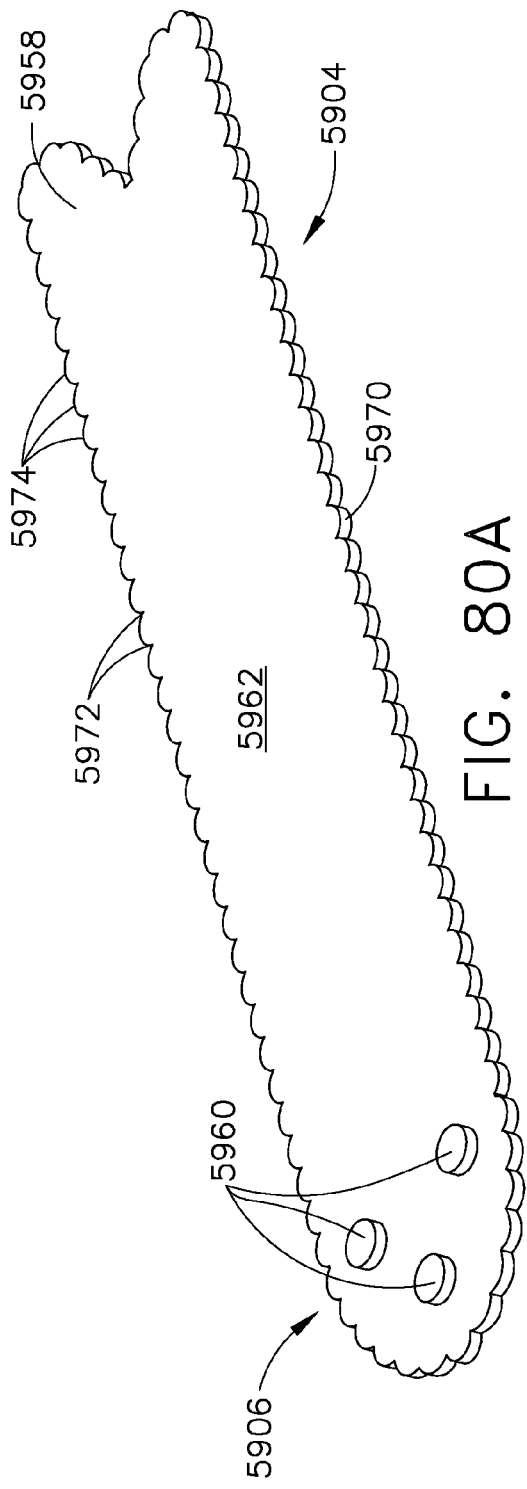
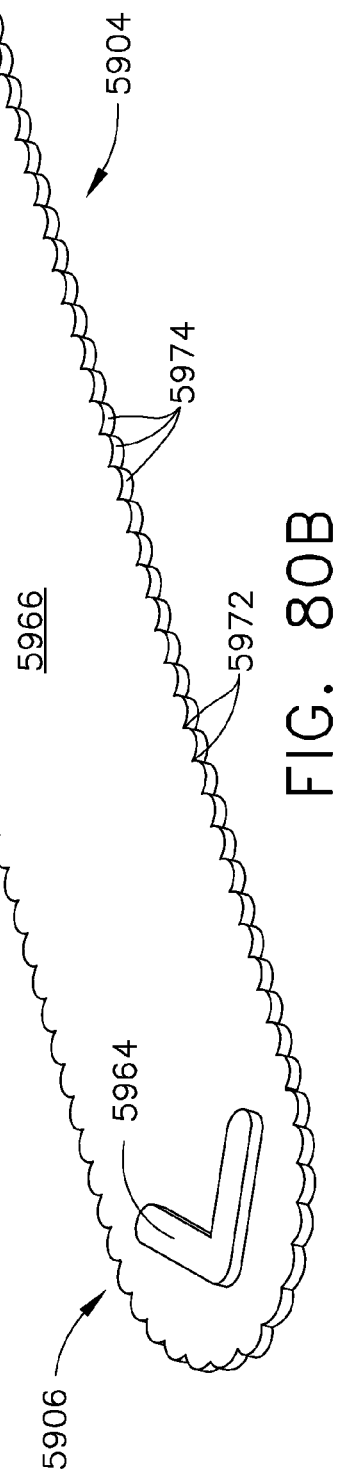
FIG. 80A
FIG. 80B

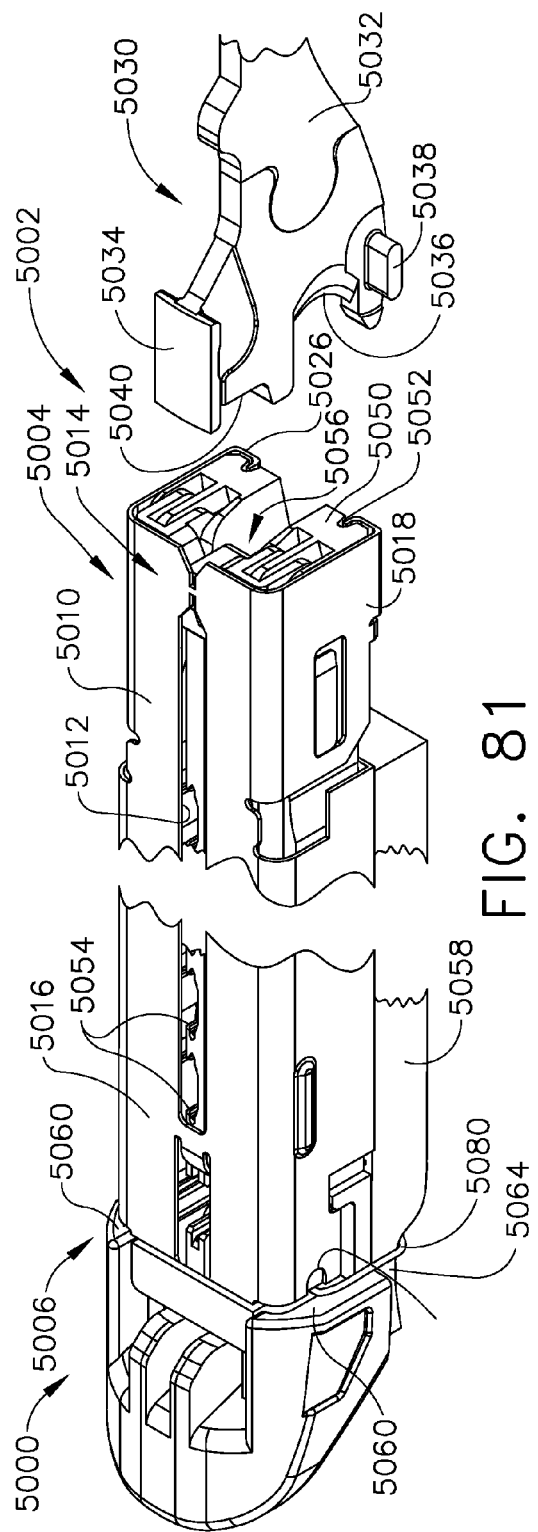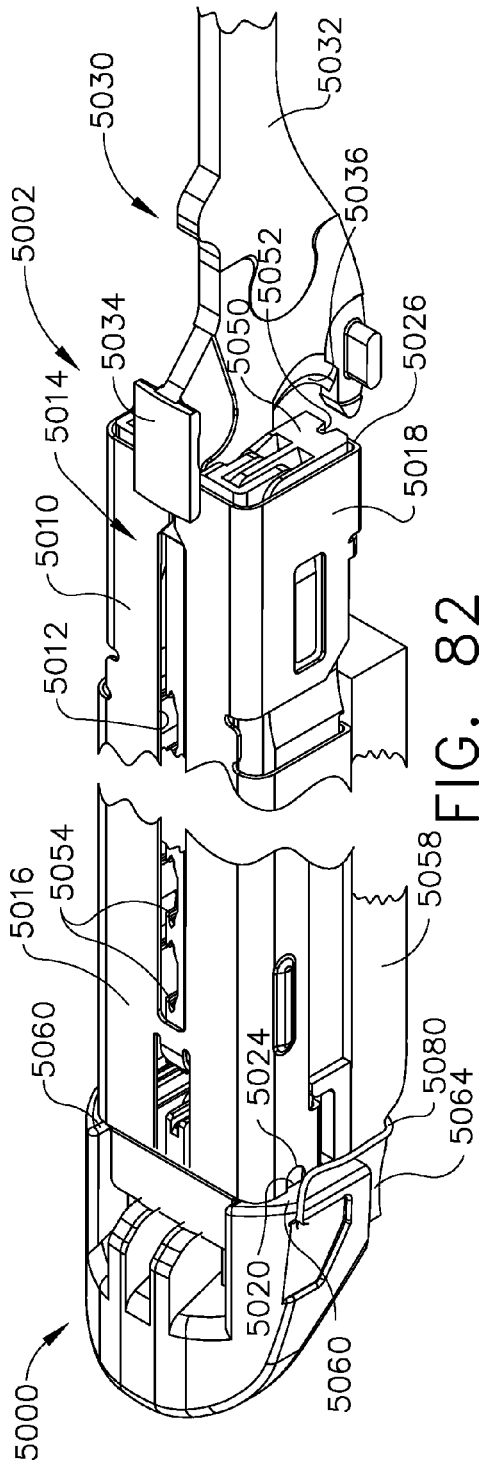

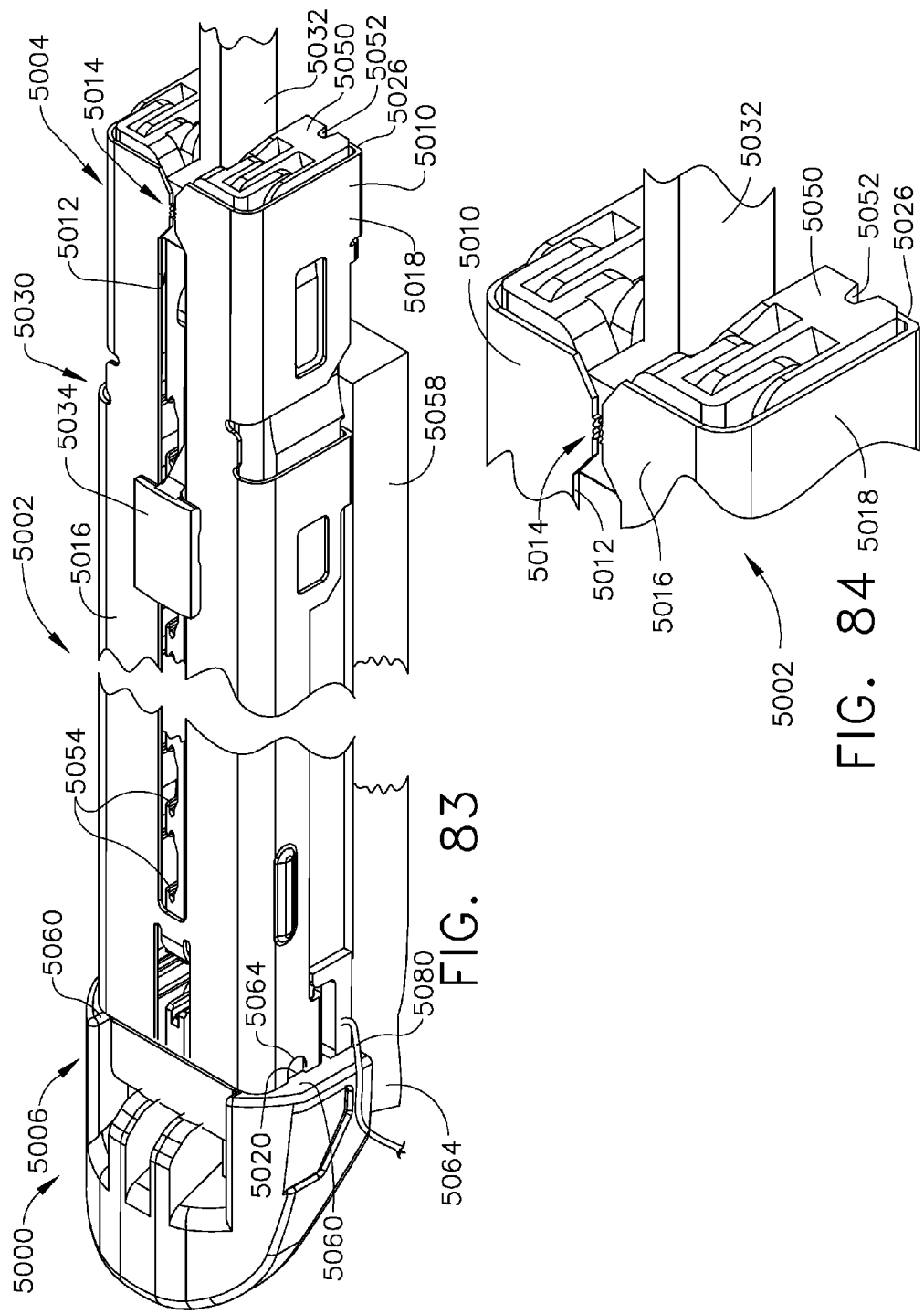

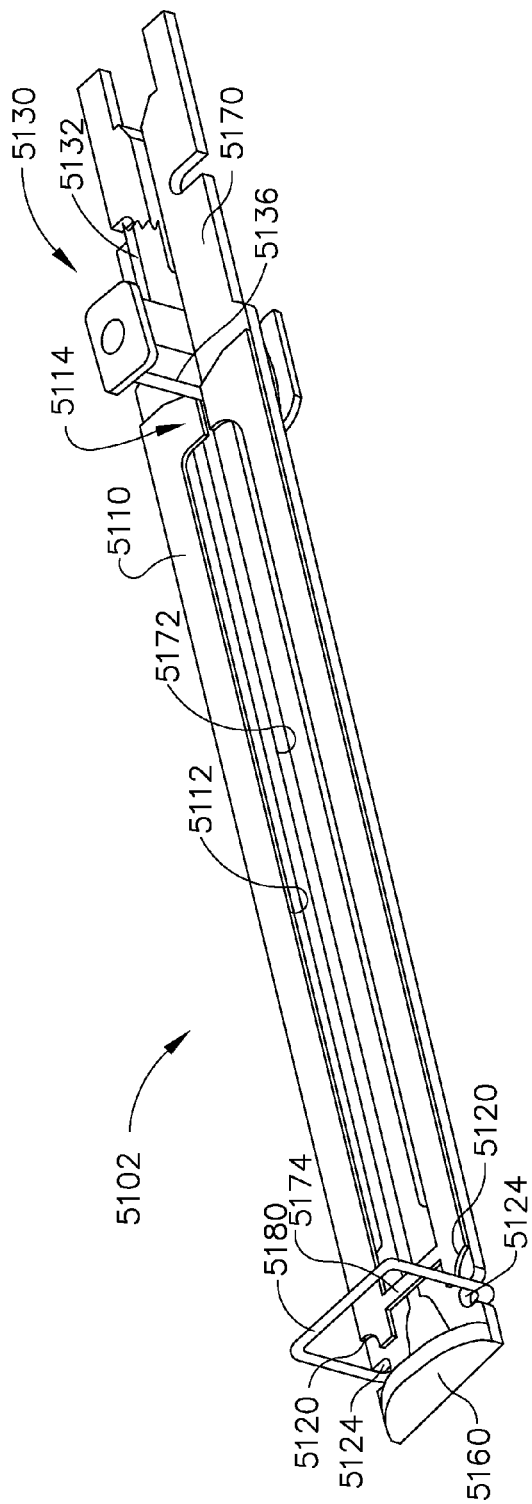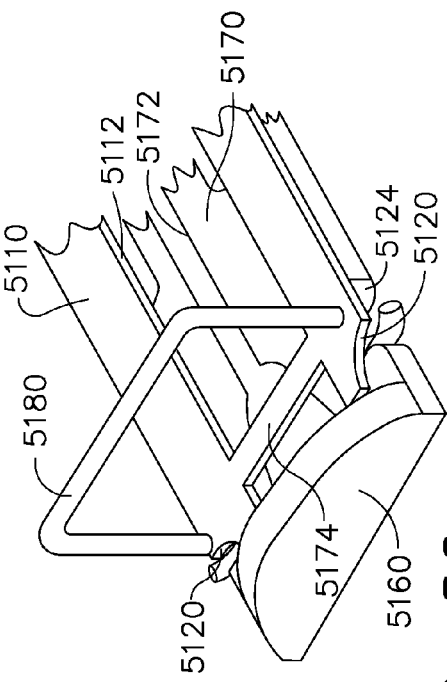
FIG. 85
FIG. 86

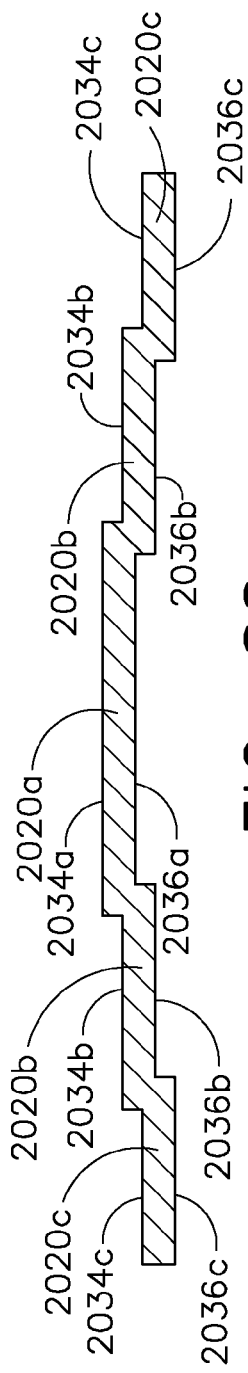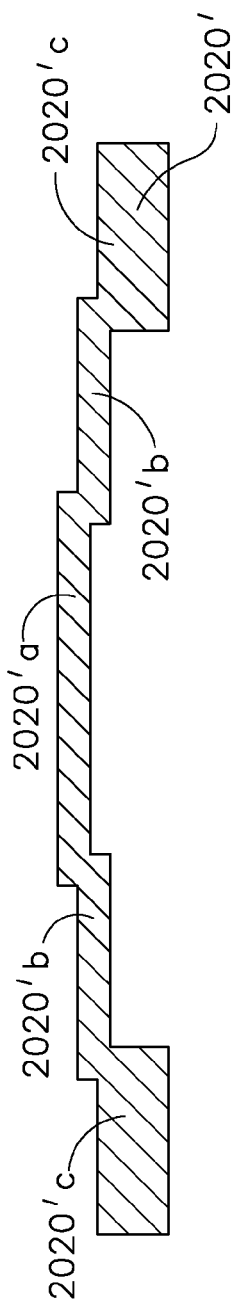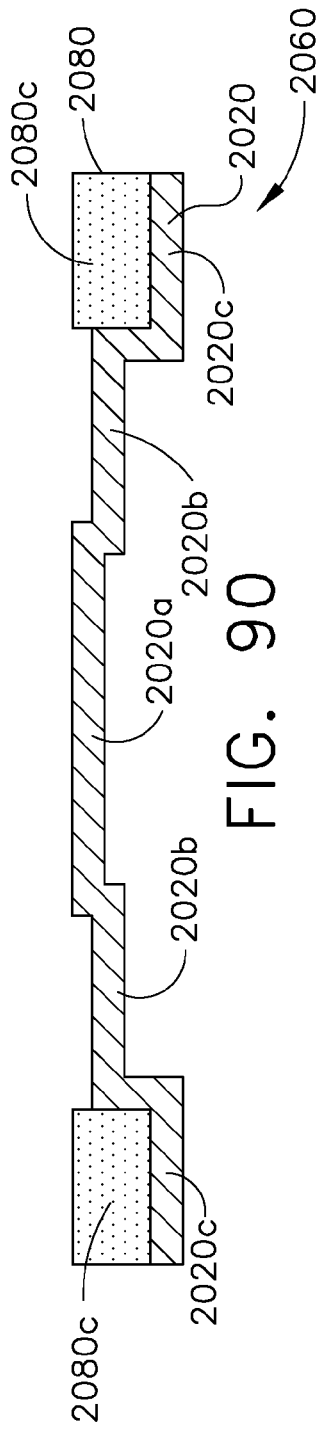

ACTUATOR FOR RELEASING A LAYER OF MATERIAL FROM A SURGICAL END EFFECTOR

CROSS REFERENCE TO RELATED APPLICATION

This non-provisional patent application is a continuation-in-part application under 35 U.S.C. §120 of U.S. patent application Ser. No. 12/032,002, entitled SURGICAL END EFFECTOR HAVING BUTTRESS RETENTION FEATURES, filed on filed Feb. 15, 2008, now U.S. Pat. No. 8,371,491, the entire disclosure of which is hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of exemplary embodiments of the invention taken in conjunction with the accompanying drawings, wherein:

FIG. 15 is a perspective view of a non-articulating disposable loading unit usable with the surgical stapling instrument shown in FIG. 11;

FIG. 16 is a perspective view of an articulating disposable loading unit usable with the surgical stapling instrument shown in FIG. 11;

FIG. 20 is an enlarged perspective view of the distal end of a staple cartridge for use with the surgical stapling instrument shown in FIG. 11;

FIG. 21 is a side cross-sectional view taken along the section line indicated in FIG. 20;

FIG. 24 is an enlarged perspective view of the mounting assembly of the disposable loading unit shown in FIG. 17 mounted to a distal end portion of the proximal housing portion;

FIG. 25 is an enlarged perspective view of the proximal housing portion and the mounting assembly of the disposable loading unit shown in FIG. 17 with the upper housing half removed;

FIG. 26 is a perspective view of the proximal housing portion and the mounting assembly of the disposable loading unit shown in FIG. 17 with the upper housing half removed;

FIG. 32 is a partial perspective view of an end effector for use with the surgical stapling instrument of FIG. 29;

FIG. 33 is a partial detail view of the end effector of FIG. 32;

FIG. 36 is a perspective view of a tissue thickness compensator including pyramid-shaped cleats according to various embodiments;

FIG. 37 is a cross sectional view of the tissue thickness compensator in FIG. 36;

FIG. 38 is a perspective view of a corrugated tissue thickness compensator according to various embodiments;

FIG. 39 is a cross sectional view of the tissue thickness compensator in FIG. 38;

FIG. 40 is a perspective view of a tissue thickness compensator including a scalloped outer edge according to various embodiments;

FIG. 41 is a perspective view of a tissue thickness compensator including a scalloped outer edge according to various embodiments;

FIG. 45 is a perspective view of a tissue thickness compensator including a rolled outer edge according to various embodiments;

FIG. 46 is a partial cross sectional view of the rolled outer edge in FIG. 45;

FIG. 58 is a plan view of two layers at least partially overlapping with each other;

FIG. 59 is a perspective view of a staple cartridge utilizing one of the layers illustrated in FIG. 58;

FIG. 64 is a perspective view of a fastener cartridge assembly for use with an end effector assembly according to various embodiments of the present disclosure, depicting a layer of material released from a cartridge body of the fastener cartridge assembly;

FIG. 65 is an elevation view of the fastener cartridge assembly of FIG. 64 with various elements removed therefrom, depicting the layer of material secured to the cartridge body by a proximal connector and by a distal connector, and further depicting a firing assembly in an unfired position;

FIG. 66 is an elevation view of the fastener cartridge assembly of FIG. 64 with various elements removed therefrom, depicting the layer of material secured to the cartridge body by the distal connector, and further depicting the firing assembly in a partially fired position;

FIG. 67 is a perspective view of a fastener cartridge assembly for use with an end effector assembly according to various embodiments of the present disclosure, depicting a layer of material released from a cartridge body of the fastener cartridge assembly;

FIG. 68 is a perspective view of the fastener cartridge assembly of FIG. 67, depicting the layer of material secured to the cartridge body by a proximal connector and by a distal connector;

FIG. 72 is a perspective view of a fastener cartridge assembly for use with an end effector assembly according to various embodiments of the present disclosure, depicting a layer of material released from a cartridge body of the fastener cartridge assembly;

FIG. 73 is a perspective view of the fastener cartridge assembly of FIG. 72, depicting the layer of material secured to the cartridge body by a first connector and by a second connector;

FIG. 74 is a cross-sectional, perspective view of the fastener cartridge assembly of FIG. 72 taken along the plane indicated in FIG. 73, depicting the layer of material secured to the cartridge body by the proximal connector of FIG. 73;

FIG. 75 is a cross-sectional, elevation view of the layer of material of FIG. 72 taken along the plane indicated in FIG. 73;

FIG. 76 is a perspective view of a fastener cartridge assembly for use with an end effector assembly according to various embodiments of the present disclosure, depicting a layer of material released from a cartridge body of the fastener cartridge assembly;

FIG. 77 is a perspective view of the fastener cartridge assembly of FIG. 76, depicting the layer of material secured to the cartridge body by a proximal connector and by a distal connector;

FIG. 80A is a perspective view of a layer of material for use with an end effector assembly according to various embodiments of the present disclosure;

FIG. 80B is a perspective view of the layer of material of FIG. 80A;

FIG. 81 is a partial, perspective view of a jaw of an end effector assembly according to various embodiments of the present disclosure, depicting a layer of material secured to a cartridge body by a distal connector, and further depicting an actuator in a pre-actuated position;

FIG. 82 is a partial, perspective view of the jaw of FIG. 81, depicting a firing assembly against a release stop of the actuator, depicting the actuator in an actuated position, and further depicting the distal connector broken by the actuator;

FIG. 83 is a partial, perspective view of the jaw of FIG. 81, depicting the release stop of the actuator broken by the firing assembly, and further depicting the foot of the firing assembly distal to the release stop;

FIG. 84 is a detail, perspective view of the release stop of FIG. 83 broken by the firing assembly;

FIG. 85 is a perspective view of a jaw of an end effector assembly according to various embodiments of the present disclosure, the jaw having various elements removed therefrom, depicting an actuator in a pre-actuated position, and further depicting a distal connector;

FIG. 86 is a partial, perspective view of the jaw of FIG. 85, depicting the actuator in an actuated position, and further depicting the distal connector broken by the actuator;

FIG. 88 is a cross-sectional view of a tissue thickness compensator in accordance with at least one embodiment;

FIG. 89 is a cross-sectional view of a tissue thickness compensator in accordance with at least one embodiment; and FIG. 90 is a cross-sectional view of a tissue thickness compensator in accordance with at least one embodiment.

DETAILED DESCRIPTION

Figure 1:
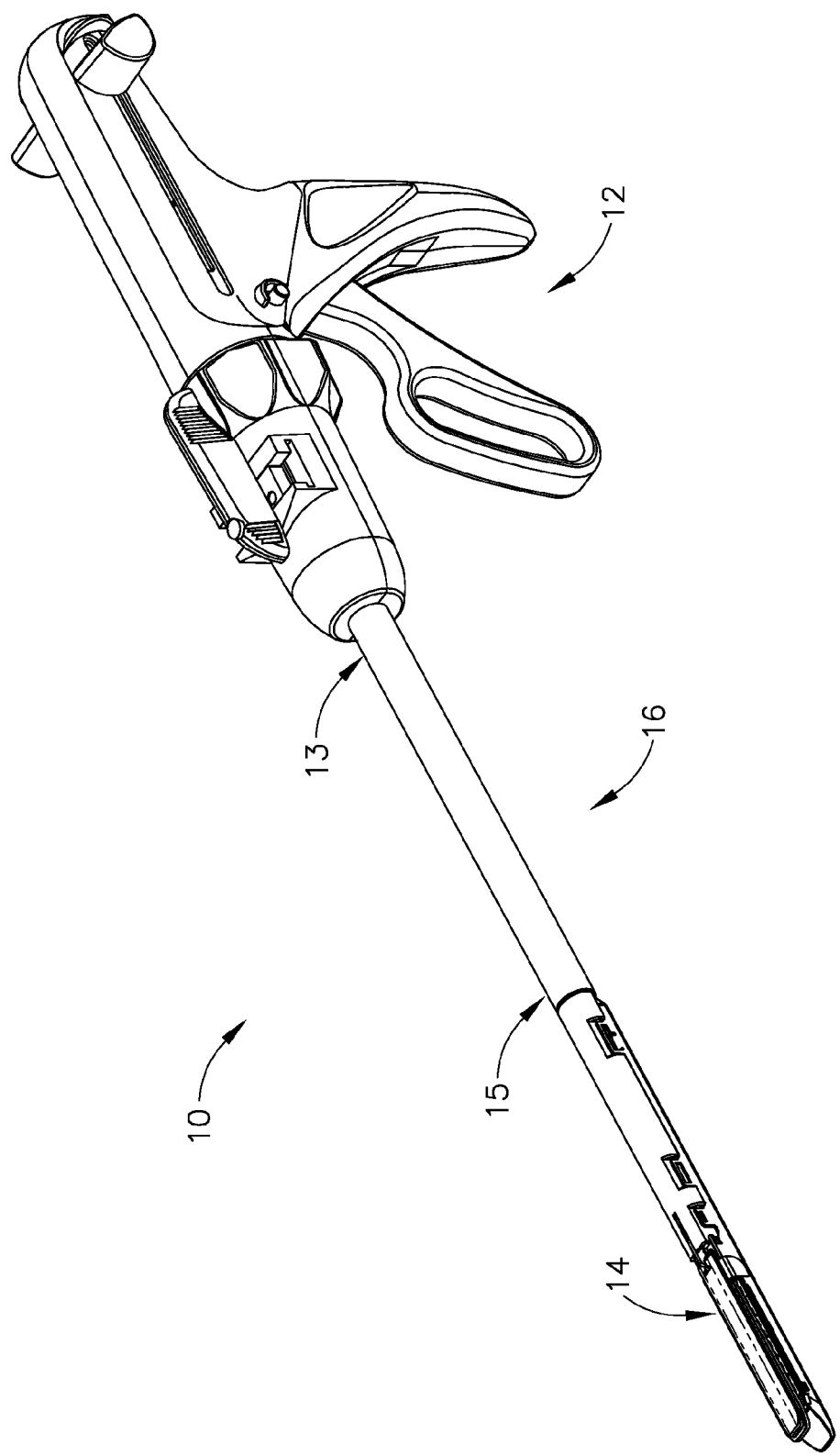
FIG. 1 is a perspective view of an end effector assembly attached to a distal end of a surgical instrument in accordance with one non-limiting embodiment of the present invention.
Figure 2:
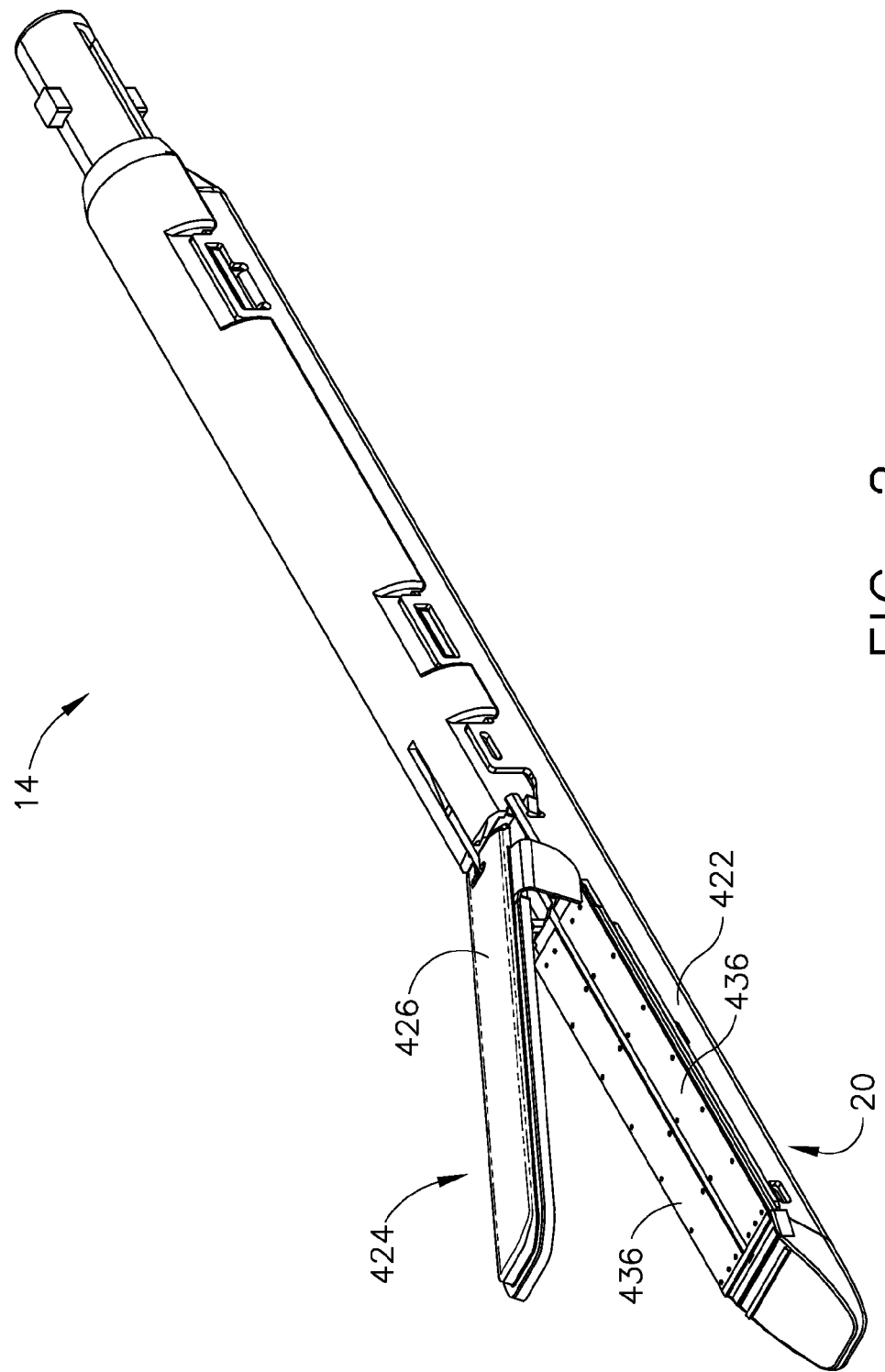
FIG. 2 is a perspective view of an end effector assembly including at least one piece of buttress material, wherein the end effector assembly is in an open configuration in accordance with one non-limiting embodiment of the present invention.
Figure 3:
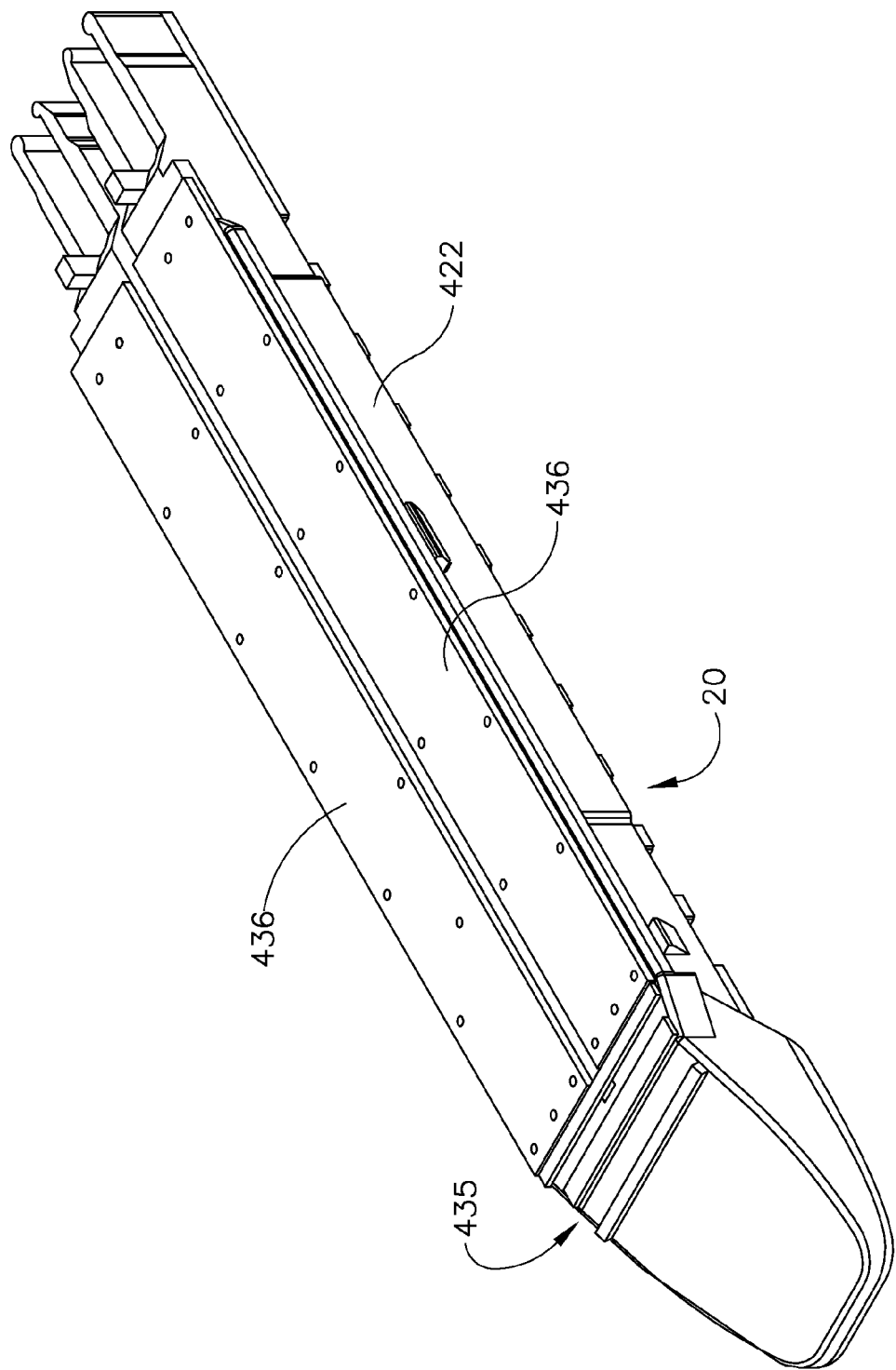
FIG. 3 is a perspective view of a staple cartridge of the end effector assembly of FIG. 2, wherein the buttress material is releasably retained thereto.

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Pat. No. 9,295,464;

U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084;

U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741;

U.S. patent application Ser. No. 13/241,629, entitled SURGICAL INSTRUMENT WITH SELECTIVELY ARTICULATABLE END EFFECTOR, now U.S. Patent Application Publication No. 2012/0074200;

U.S. patent application Ser. No. 13/433,096, entitled TISSUE THICKNESS COMPENSATOR COMPRISING A PLURALITY OF CAPSULES, now U.S. Pat. No. 9,301,752;

U.S. patent application Ser. No. 13/433,103, entitled TISSUE THICKNESS COMPENSATOR COMPRISING A PLURALITY OF LAYERS, now U.S. Patent Application Publication No. 2012/0241498;

U.S. patent application Ser. No. 13/433,098, entitled EXPANDABLE TISSUE THICKNESS COMPENSATOR, now U.S. Pat. No. 9,301,753;

U.S. patent application Ser. No. 13/433,102, entitled TISSUE THICKNESS COMPENSATOR COMPRISING A RESERVOIR, now U.S. Pat. No. 9,232,941;

U.S. patent application Ser. No. 13/433,114, entitled RETAINER ASSEMBLY INCLUDING A TISSUE THICKNESS COMPENSATOR, now U.S. Pat. No. 9,386,988;

U.S. patent application Ser. No. 12/433,136, entitled TISSUE THICKNESS COMPENSATOR COMPRISING AT LEAST ONE MEDICAMENT, now U.S. Pat. No. 8,533,784;

U.S. patent application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;

U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. patent application Ser. No. 13/433,155, entitled TISSUE THICKNESS COMPENSATOR COMPRISING RESILIENT MEMBERS, now U.S. Patent Application Publication No. 2012/0241502;

U.S. patent application Ser. No. 13/433,163, entitled METHODS FOR FORMING TISSUE THICKNESS COM- PENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. patent application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. patent application Ser. No. 13/433,118, entitled TISSUE THICKNESS COMPENSATOR COMPRISED OF A PLURALITY OF MATERIALS, now U.S. Patent Application Publication No. 2013/0256365;

U.S. patent application Ser. No. 13/433,135, entitled MOVABLE MEMBER FOR USE WITH A TISSUE THICKNESS COMPENSATOR, now U.S. Patent Application Publication No. 2013/0256382;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/433,126, entitled TISSUE THICKNESS COMPENSATOR COMPRISING TISSUE INGROWTH FEATURES, now U.S. Pat. No. 9,320,523;

U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373; and U.S. patent application Ser. No. 13/433,129, entitled TISSUE THICKNESS COMPENSATOR COMPRISING A PLURALITY OF MEDICAMENTS, now U.S. Pat. No. 9,211,120.

The Applicant of the present application also owns the U.S. Patent Applications identified below which are each herein incorporated by reference in their respective entirety:

U.S. patent application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. patent application Ser. No. 11/714,049, entitled SURGICAL STAPLING DEVICE WITH ANVIL HAVING STAPLE FORMING POCKETS OF VARYING DEPTHS, now U.S. Patent Application Publication No. 2007/0194082;

U.S. patent application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. patent application Ser. No. 11/711,975, entitled SURGICAL STAPLING DEVICE WITH STAPLE DRIVERS OF DIFFERENT HEIGHT, now U.S. Patent Application Publication No. 2007/0194079;

U.S. patent application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. patent application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. patent application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. patent application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891;

U.S. patent application Ser. No. 13/369,629, entitled ROBOTICALLY-CONTROLLED CABLE-BASED SURGICAL END EFFECTORS, now U.S. Pat. No. 8,800,838;

U.S. patent application Ser. No. 12/695,359, entitled SURGICAL STAPLING DEVICES FOR FORMING STAPLES WITH DIFFERENT FORMED HEIGHTS, now U.S. Pat. No. 8,464,923; and U.S. patent application Ser. No. 13/072,923, entitled STAPLE CARTRIDGES FOR FORMING STAPLES HAVING DIFFERING FORMED STAPLE HEIGHTS, now U.S. Pat. No. 8,567,656.

The Applicant of the present application also owns the U.S. Patent Applications identified below which were filed on even date herewith and which are each herein incorporated by reference in their respective entirety:

U.S. patent application Ser. No. 13/763,112, entitled SURGICAL STAPLING CARTRIDGE WITH LAYER RETENTION FEATURES, now U.S. Patent Application Publication No. 2013/0256379;

U.S. patent application Ser. No. 13/763,028, entitled ADHESIVE FILM LAMINATE, now U.S. Pat. No. 9,282,962;

U.S. patent application Ser. No. 13/763,035, entitled ACTUATOR FOR RELEASING A TISSUE THICKNESS COMPENSATOR FROM A FASTENER CARTRIDGE, now U.S. Patent Application Publication No. 2013/0214030;

U.S. patent application Ser. No. 13/763,042, entitled RELEASABLE TISSUE THICKNESS COMPENSATOR AND FASTENER CARTRIDGE HAVING THE SAME, now U.S. Patent Application Publication No. 2013/0221063;

U.S. patent application Ser. No. 13/763,048, entitled FASTENER CARTRIDGE COMPRISING A RELEASABLE TISSUE THICKNESS COMPENSATOR, now U.S. Patent Application Publication No. 2013/0221064;

U.S. patent application Ser. No. 13/763,054, entitled FASTENER CARTRIDGE COMPRISING A CUTTING MEMBER FOR RELEASING A TISSUE THICKNESS COMPENSATOR, now U.S. Pat. No. 9,272,406;

U.S. patent application Ser. No. 13/763,065, entitled FASTENER CARTRIDGE COMPRISING A RELEASABLY ATTACHED TISSUE THICKNESS COMPENSATOR, now U.S. Patent Application Publication No. 2013/0221065;

U.S. patent application Ser. No. 13/763,021, entitled STAPLE CARTRIDGE COMPRISING A RELEASABLE COVER, now U.S. Pat. No. 9,386,984;

U.S. patent application Ser. No. 13/763,078, entitled ANVIL LAYER ATTACHED TO A PROXIMAL END OF AN END EFFECTOR, now U.S. Patent Application Publication No. 2013/0256383;

U.S. patent application Ser. No. 13/763,094, entitled LAYER COMPRISING DEPLOYABLE ATTACHMENT MEMBERS, now U.S. Patent Application Publication No. 2013/0256377;

U.S. patent application Ser. No. 13/763,106, entitled END EFFECTOR COMPRISING A DISTAL TISSUE ABUTMENT MEMBER, now U.S. Patent Application Publication No. 2013/0256378;

U.S. patent application Ser. No. 13/763,095, entitled LAYER ARRANGEMENTS FOR SURGICAL STAPLE CARTRIDGES, now U.S. Patent Application Publication No. 2013/0161374;

U.S. patent application Ser. No. 13/763,147, entitled IMPLANTABLE ARRANGEMENTS FOR SURGICAL STAPLE CARTRIDGES, now U.S. Patent Application Publication No. 2013/0153636;

U.S. patent application Ser. No. 13/763,192, entitled MULTIPLE THICKNESS IMPLANTABLE LAYERS FOR SURGICAL STAPLING DEVICES, now U.S. Patent Application Publication No. 2013/0146642;

U.S. patent application Ser. No. 13/763,161, entitled RELEASABLE LAYER OF MATERIAL AND SURGICAL END EFFECTOR HAVING THE SAME, now U.S. Patent Application Publication No. 2013/0153641; and U.S. patent application Ser. No. 13/763,037, entitled STAPLE CARTRIDGE COMPRISING A COMPRESSIBLE PORTION, now U.S. Patent Application Publication No. 2014/0224857.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

In various embodiments, a surgical stapling instrument, such as instrument 10, for example, can comprise a handle, a shaft extending from the handle, and an end effector extending from the shaft which can be configured to treat the tissue of a patient. Referring to FIG. 1, handle assembly 12 of instrument 10 can be attached to a first, or proximal, end 13 of an instrument shaft 16 and, additionally, an end effector assembly 14 can be configured to be attached to a second, or distal, end 15 of instrument shaft 16. In various embodiments, end effector assembly 14 and at least a portion of instrument shaft 16 can be configured to be positioned within, and inserted at least partially through, a cannula, or trocar, in a patient's body during a minimally invasive surgical procedure. Various surgical instruments are described in further detail in U.S. patent application Ser. No. 11/329,020, entitled SURGICAL INSTRUMENT HAVING AN ARTICULATING END EFFECTOR, which was filed on Jan. 10, 2006, now U.S. Pat. No. 7,670,334; U.S. patent application Ser. No. 11/343,321, entitled SURGICAL CUTTING AND FASTENING INSTRUMENT WITH CLOSURE TRIGGER LOCKING MECHANISM, which was filed on Jan. 31, 2006, now U.S. Patent Application Publication No. 2007/0175955; and U.S. patent application Ser. No. 11/529,935, entitled SURGICAL STAPLES HAVING ATTACHED DRIVERS AND STAPLING INSTRUMENTS FOR DEPLOYING THE SAME, which was filed on Sep. 29, 2006, now U.S. Pat. No. 8,485,412, the entire disclosures of which are hereby incorporated by reference herein.

In various embodiments, further to the above, the end effector assembly 14 can include a first jaw member 20 and a second jaw member 424 wherein at least one of the first and second jaw members can be configured to be moved relative to the other jaw member such that the tissue of a patient can be clamped therebetween. Referring to FIGS. 1-3 and 5, first jaw member 20 can include staple cartridge 422 and, additionally, second jaw member 424 can include anvil 426. In at least one embodiment, staple cartridge 422 can include a deck having a plurality of staple cavities defined therein. Anvil 426 can include an anvil cover 427 and an anvil face, wherein the anvil face can have a plurality of anvil pockets defined therein. In various embodiments, each staple cavity can be configured to removably store a staple therein and each anvil pocket can be configured to deform at least a portion of the staple as the staple is deployed. In various embodiments, at least one of the staple cartridge and the anvil can comprise one or more gripping features, or ridges, 435 which can be configured to hold the tissue within the end effector.

Further to the above, end effector assembly 14 can include at least one piece of buttress material 436 and/or 436' which can be configured to be positioned intermediate the first and second jaw members and can be releasably retained to one of the cartridge deck and/or the anvil face, for example. In at least one embodiment, a surface on the piece of buttress material can be configured to contact tissue as the tissue is clamped between the first and second jaw members. In such an embodiment, the buttress material surface can be used to distribute the compressive clamping force over the tissue, remove excess fluid from the tissue, and/or improve the purchase of the staples. In various embodiments, one or more pieces of buttress material can be positioned within the end effector assembly. In at least one embodiment, one piece of buttress material 436 can be attached to staple cartridge 422 and one piece of buttress material 436' can be attached to anvil 426. In at least one other embodiment, two pieces of buttress material 436 can be positioned on the cartridge deck and one piece of buttress material 436' can be positioned on the anvil face, for example. In other various embodiments, any suitable number of pieces of buttress material can be situated within an end effector assembly. In any event, in various embodiments, the piece(s) of buttress material can be comprised of a material such as, a bioabsorbable material, a biofragmentable material, and/or a dissolvable material, for example, such that the buttress material can be absorbed, fragmented, and/or dissolved during the healing process. In at least one embodiment, the piece(s) of buttress material can be at least partially comprised of a therapeutic drug which can be configured to be released over time to aid the tissue in healing, for example. In further various embodiments, the piece(s) of buttress material can include a non-absorbable and/or non-dissolvable material, for example.

In various embodiments, an end effector assembly can include at least one connection member or fastener, such as connection members 38, for example, which can be utilized to releasably retain a piece of buttress material to at least one of an anvil and a staple cartridge, for example. In various embodiments, connection members can be configured to be released from an end effector and deployed along with a piece of buttress material. In at least one embodiment, head portions of the connection members can be configured to be separated from body portions of the connection members such that the head portions can be deployed with the piece of buttress material while the body portions remain attached to the end effector. In other various embodiments, the entirety of the connection members can remain engaged with the end effector when the piece of buttress material is detached from the end effector. In any event, in at least one embodiment, the connection members can be at least partially comprised of at least one of a bioabsorbable material, a biofragmentable material, and a dissolvable material such that the connection members can be absorbed, fragmented, and/or dissolved within the body. In various embodiments, the connection members comprised of a therapeutic drug which can be configured to be released over time to aid the tissue in healing, for example. In further various embodiments, the connection members can include a non-absorbable and/or non-dissolvable material, for example, such as a plastic.

In various embodiments, the connection members can be arranged in any suitable pattern or configuration. In at least one embodiment, the connection members can be situated around the outer perimeter of piece of buttress material 436, for example. In at least one embodiment, the connection members can be positioned proximate to one or more sides and/or ends of the piece of buttress material, for example, to prevent, or at least assist in preventing, the buttress material from peeling away from the staple cartridge deck and/or the anvil face when the end effector is inserted through a trocar or engaged with tissue. In various embodiments, the connection members can be used in conjunction with any suitable adhesive, such as cyanoacrilate, for example, to releasably retain the piece of buttress material, or at least a portion of the buttress material, to the end effector. In at least one embodiment, the adhesive can be applied to connection members prior to the connection members being engaged with the apertures in the piece of buttress material, staple cartridge, and/or anvil.

Figure 4:
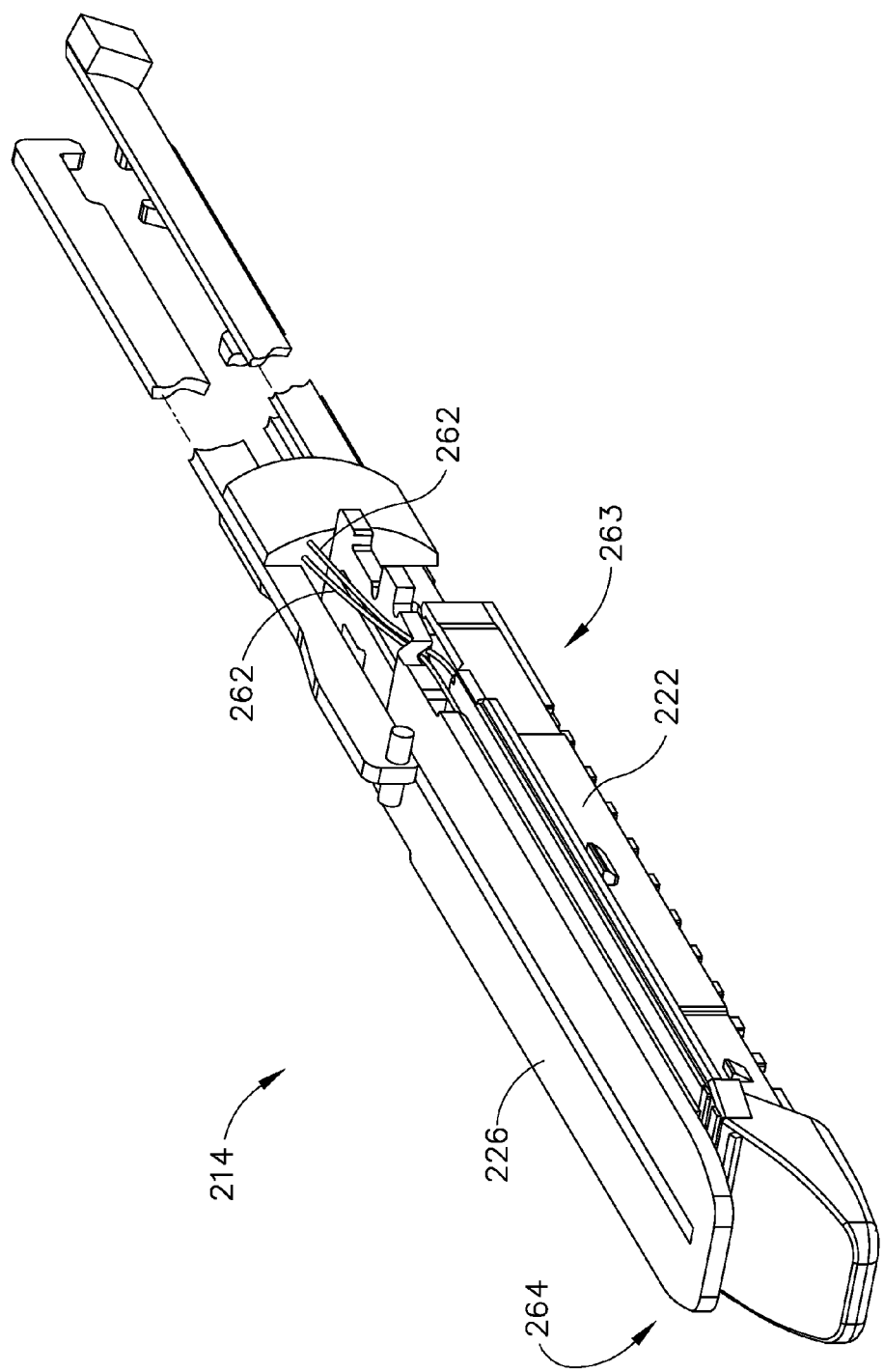
FIG. 4 is a partial perspective view of an end effector assembly with some components removed, wherein the end effector assembly includes a retractable member configured to releasably retain at least one piece of buttress material.
Figure 5:
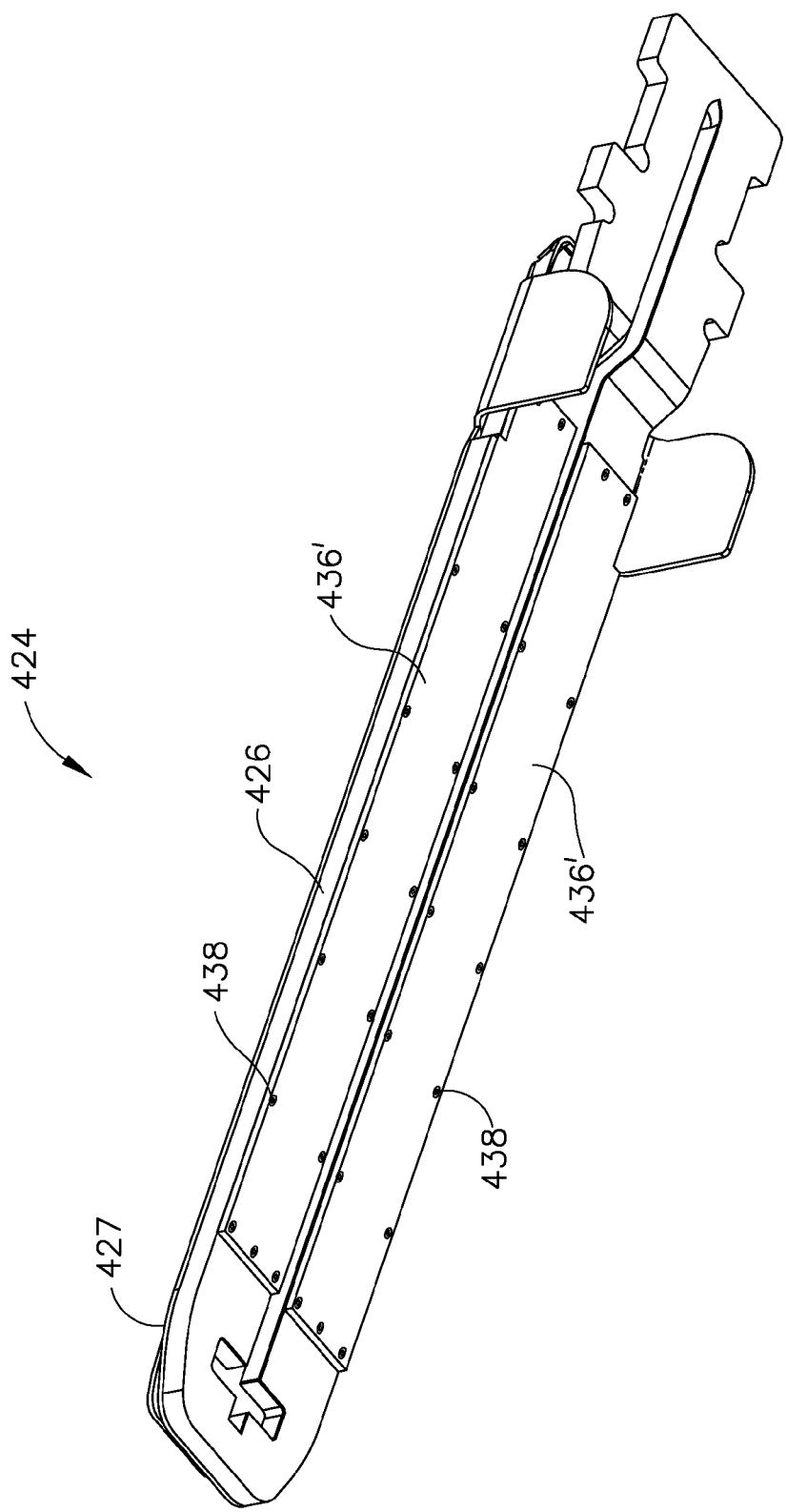
FIG. 5 is a perspective view of an anvil of the end effector assembly of FIG. 2, wherein the anvil has at least one piece of buttress material releasably retained thereto.

Referring to FIG. 4, a retention member can be configured to be moved within an end effector between a first position and a second position to releasably retain a tissue thickness compensator to the end effector. An end effector assembly 214 can include a first jaw including staple cartridge 222 and a second jaw including anvil 226 wherein retention member 262 can be moved relative to staple cartridge 222 and anvil 226. For example, retention member 262 can be moved between a first, or extended, position near distal end 264 to a second, or retracted, position near proximal end 263. In its extended position, retention member 262 can hold a tissue thickness compensator such as, for example, tissue thickness compensator 436 (see e.g. FIG. 3) in position as end effector 214 is inserted into a surgical site. Thereafter, end effector 214 can be closed onto tissue, for example, and staples can be deployed through the compensator 436 into the tissue. Retention member 262 can be moved into its retracted position such that retention member 262 can be operably disengaged from compensator 436. Alternatively, retention member 262 can be retracted prior to the staples being deployed. In any event, as a result of the above, end effector 214 can be opened and withdrawn from the surgical site leaving behind the stapled compensator 436 and tissue.

Figure 6:
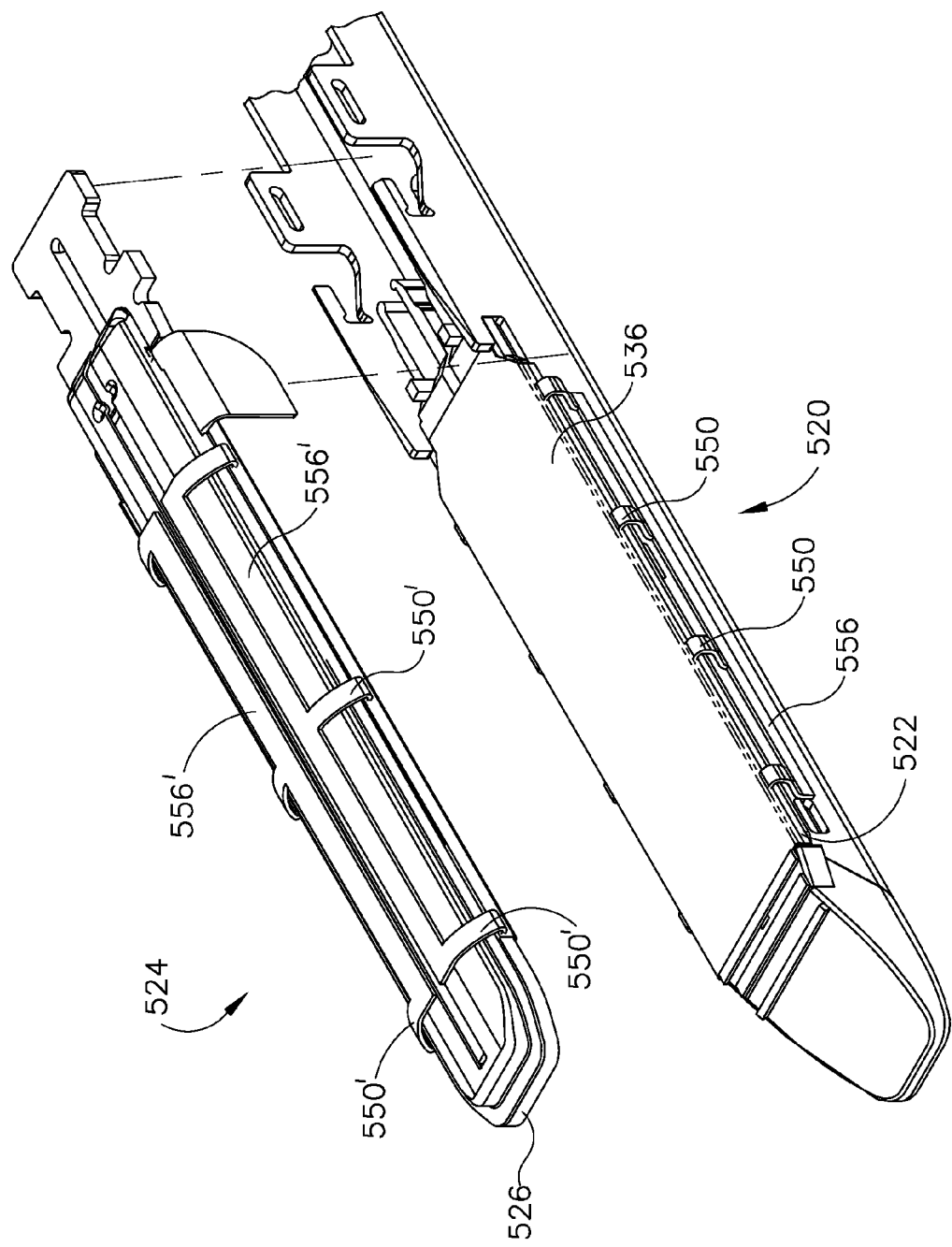
FIG. 6 is an exploded view of an end effector assembly including a staple cartridge and an anvil in accordance with one non-limiting embodiment of the present invention.
Figure 7:
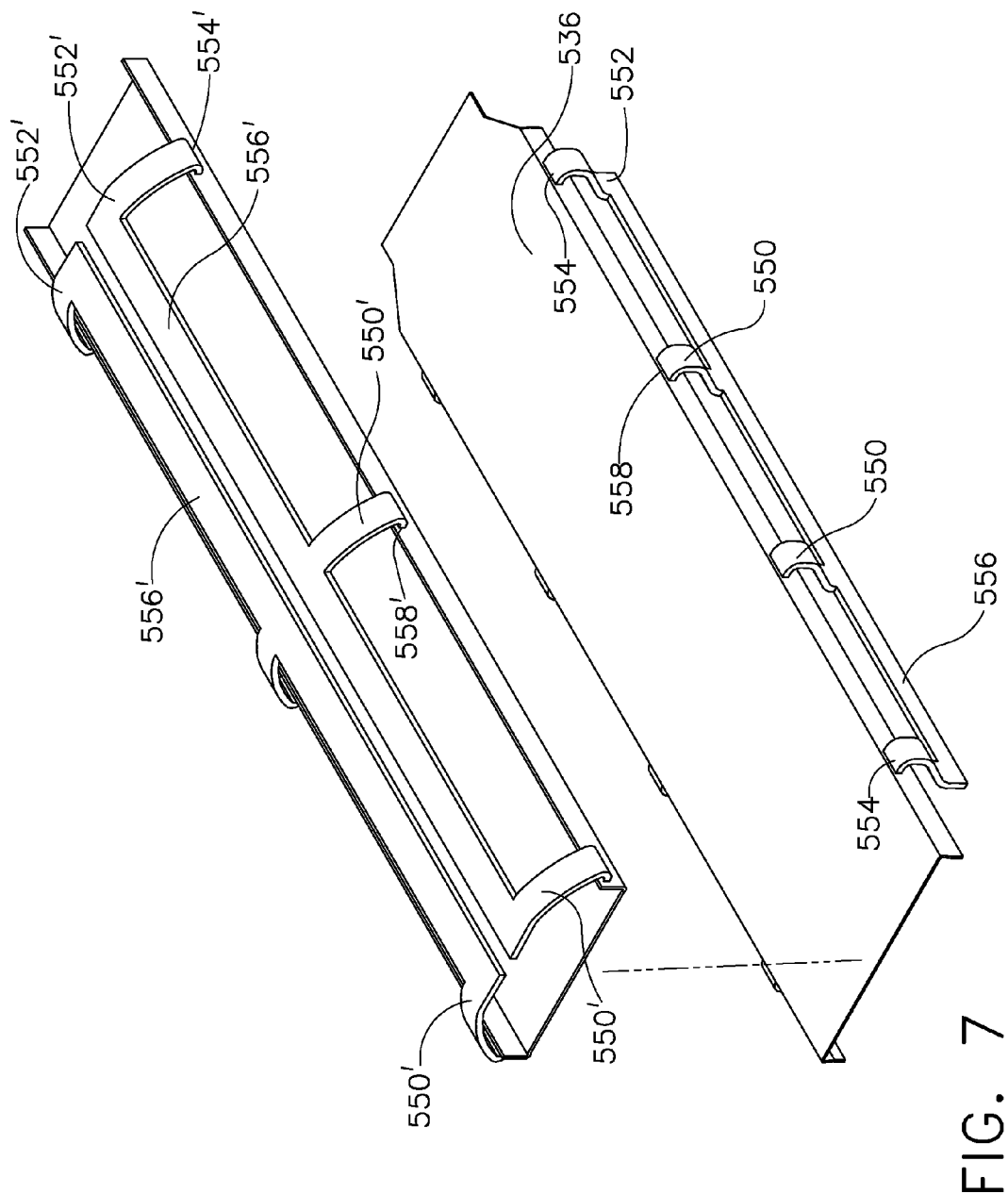
FIG. 7 is an exploded view of the end effector assembly of FIG. 6 with some components removed.

In various embodiments, referring to FIGS. 6 and 7, at least one resilient member can be utilized to releasably retain a piece of buttress material to a staple cartridge and/or anvil of an end effector. Similar to the above, a first jaw 520 of the end effector can comprise a staple cartridge 522 and a second jaw 524 can comprise an anvil 526. In at least one embodiment, at least one resilient member, such as resilient members 550 or 550', for example, can include a first end, such as first ends 552 or 552', configured to be attached to, or integrally formed with, at least one of first and second jaw members 520 and 524. In at least one embodiment, each resilient member 550 can include a second end, such as second ends 554 or 554', for example, configured to contact and releasably retain a piece of buttress material, such as piece of buttress material 536, for example, to at least one of the first and second jaw members. In various embodiments, second end 554 can include tip 558 which can be configured to grip at least a portion of piece of buttress material 536, for example. In various embodiments, tip 558 can be contoured and/or configured to include a rough or ribbed surface, for example, in order to frictionally engage the piece of buttress material. Similarly, each second end 554' can comprise a tip 558' configured to engage and hold a piece of buttress material to the anvil.

In various embodiments, referring again to FIGS. 6 and 7, a plurality of resilient members can be provided on at least two sides of a jaw member to retain side portions of the piece of buttress material to the jaw member. In at least one embodiment, first ends 552 of each individual resilient member 550 can be attached to one another by a connecting member, such as connecting member, or bar, 556 or 556', for example. In various embodiments, connecting member 556 can be attached to second jaw member 524 such that connection member 556 can provide support to resilient members 550. In other various embodiments, a plurality of resilient members 550 can be attached to at least one of the first and second jaw members without the use of a connecting member. In such an embodiment, the first ends of the resilient members can be attached directly to one of the first and second jaw members, for example. In at least one embodiment, resilient members 550, for example, can be configured to release buttress material 536 after staples have been deployed through the buttress material and/or when the buttress material is disengaged from the end effector. In at least one embodiment, the resilient members can be comprised of an elastic material such as metal or plastic, for example.

As outlined above, an end effector assembly can include a staple cartridge, an anvil, and at least one piece of buttress material positioned intermediate the staple cartridge and the anvil. In at least one embodiment, referring to FIG. 8, a piece of buttress material, such as buttress material 336, can be configured to be snap-fit to at least one of staple cartridge 322 and/or an anvil to releasably retain the piece of buttress material within the end effector. The staple cartridge 322 can include first side wall 302 and a second side wall opposite the first side wall 302, wherein at least one of the first and second side walls can include a lip 306 extending outwardly therefrom. In various embodiments, buttress material 336 can include first edge, or side, 308, second edge, or side, 310, and at least one lip 312 extending at least partially along the length of edges 308 and 310. In at least one embodiment, lips 312 can be configured to engage lips 306 in a snap-fit fashion in order to releasably retain buttress material 336 to staple cartridge 322.

Further to the above, buttress material 336 can include surface 316 which can be configured to be positioned adjacent to or against deck 328 of staple cartridge 322. In at least one embodiment, side edges 308 and 310 can comprise sidewalls which can extend in a perpendicular or transverse direction relative to surface 316. In such embodiments, lips 312 can extend from these sidewalls such that lips 312 can be interlocked behind lips 306 of staple cartridge 322. In various embodiments, lips 312 of buttress material 336 can be disengaged from lips 306 of staple cartridge 322 when the staples are deployed from staple cartridge 322. More particularly, when the staples are deployed, the staples can contact buttress material 336, apply an upward force to buttress material 336, and dislodge buttress material 336 from staple cartridge 322. Advantageously, as a result, buttress material 336 may be automatically disengaged from staple cartridge 322 when the staples are deployed therefrom and/or when the end effector is opened as described above.

In various embodiments, a piece of buttress material can include at least one member extending therefrom which can be configured to releasably retain the buttress material to one of a staple cartridge and/or an anvil. In at least one embodiment, one or more members 318 can extend from buttress material 336 in a direction which is perpendicular or transverse to surface 316. In various embodiments, each member 318 can be engaged with a staple cavity 320 defined in the deck 328 in a friction-fit or press-fit manner to releasably retain the piece of buttress material 336 to the staple cartridge. In certain embodiments, a piece of buttress material can comprise members which engage pockets in the anvil. Similar to the above, in various embodiments, staples deployed from staple cavities 320 can apply an upward force to buttress material 336 and disengage members 318 from staple cavities 320. In various embodiments, the staples can pierce projections 318 and/or buttress material 336 to secure the buttress material to the tissue as outlined above.

Figure 8:
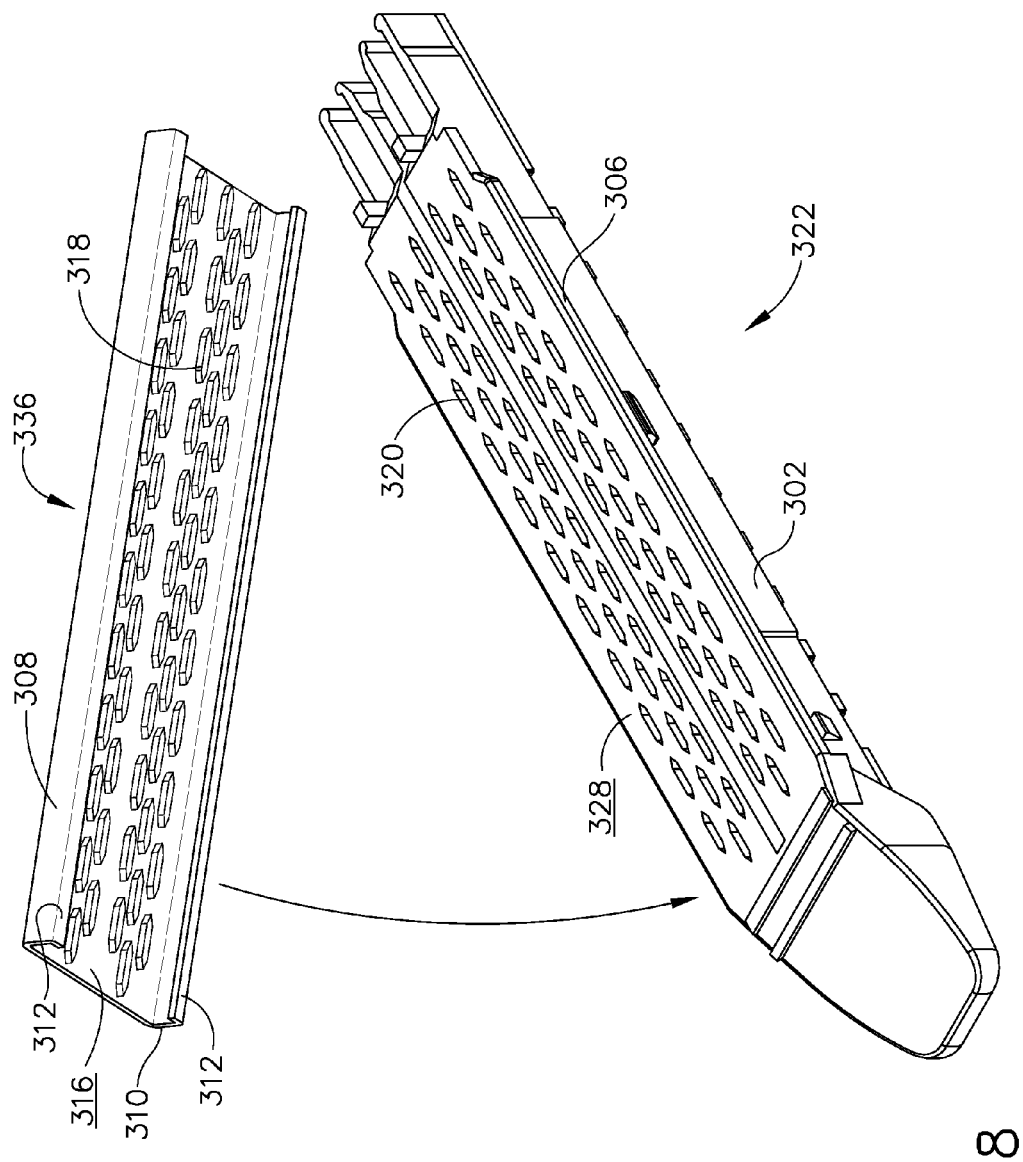
FIG. 8 is an exploded perspective view of a staple cartridge and a piece of buttress material, wherein the piece of buttress material includes a plurality of members extending therefrom.
Figure 9:
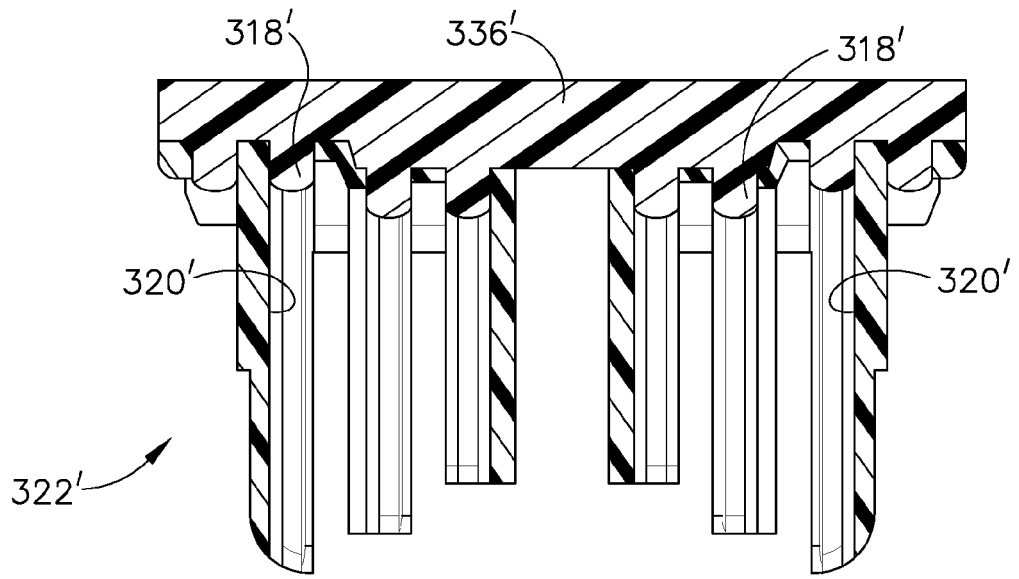
FIG. 9 is a cross-sectional view of a piece of buttress material including members engaged with staple cavities of a staple cartridge in accordance with one non-limiting embodiment of the present invention.
Figure 10:
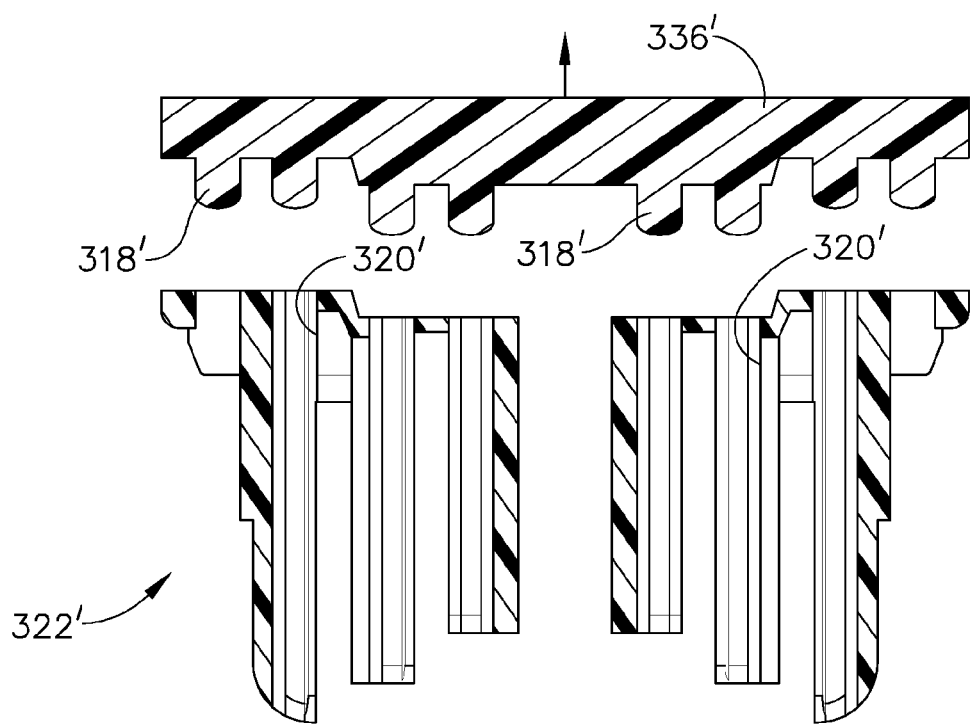
FIG. 10 is an exploded view of FIG. 9 illustrating the members separated from the staple cavities of the staple cartridge in accordance with one non-limiting embodiment of the present invention.

As illustrated in FIG. 8, a piece of buttress material can include more than one member, or projection, extending therefrom to retain a piece of buttress material to one of a staple cartridge and an anvil. In various embodiments, referring to FIGS. 9 and 10, more than one member 318' can extend from piece of buttress material 336', for example. In at least one embodiment, members 318' can be can press-fit into staple cavities 320' of staple cartridge 322', and/or into anvil pockets of an anvil (not illustrated), such that the members can frictionally retain the piece of buttress material to the staple cartridge and/or the anvil as outlined above. In various embodiments, a staple cartridge can include slots or apertures therein in addition to the staple cavities defined in the staple cartridge which can be configured to frictionally receive the members 318'. Likewise, in various embodiments, an anvil can include slots or apertures therein in addition to the staple forming pockets defined therein which can be configured to frictionally receive the members 318'.

Figure 11:
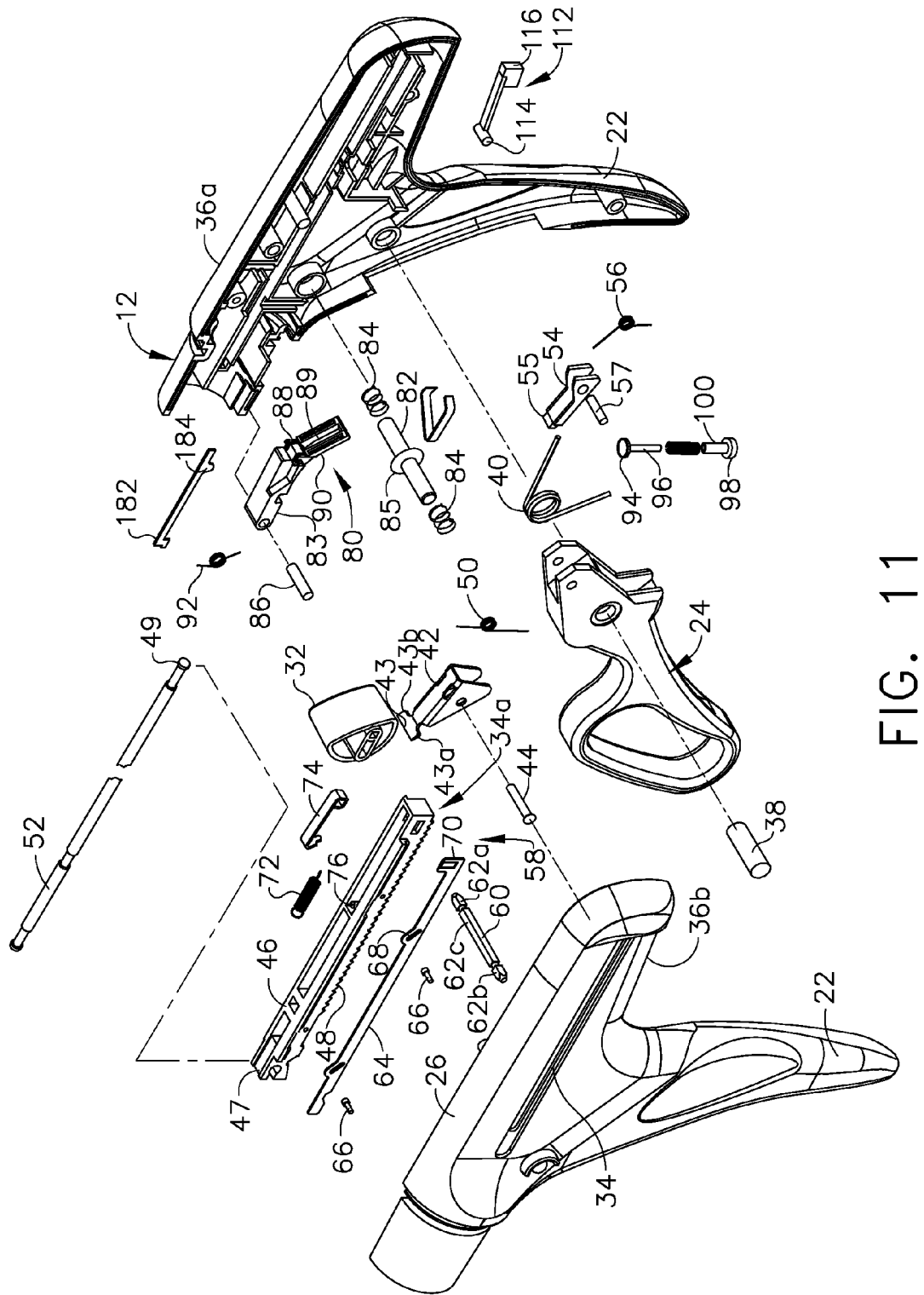
FIG. 11 is an exploded perspective view of a handle assembly of a surgical stapling instrument.
Figure 28:
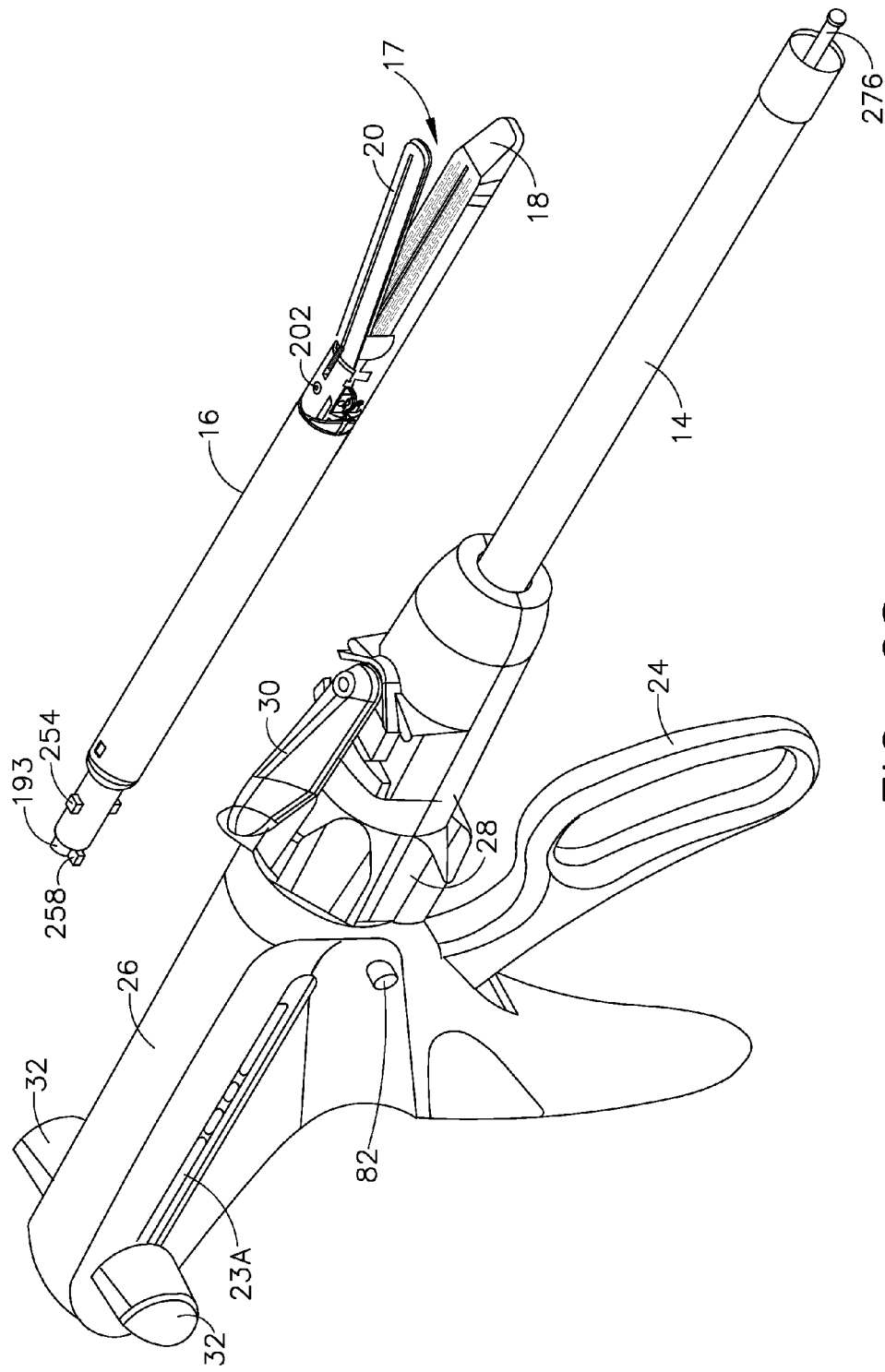
FIG. 28 is a perspective view of the surgical stapling apparatus shown in FIG. 11 with the disposable loading unit of FIG. 17 detached therefrom.
Figure 29:
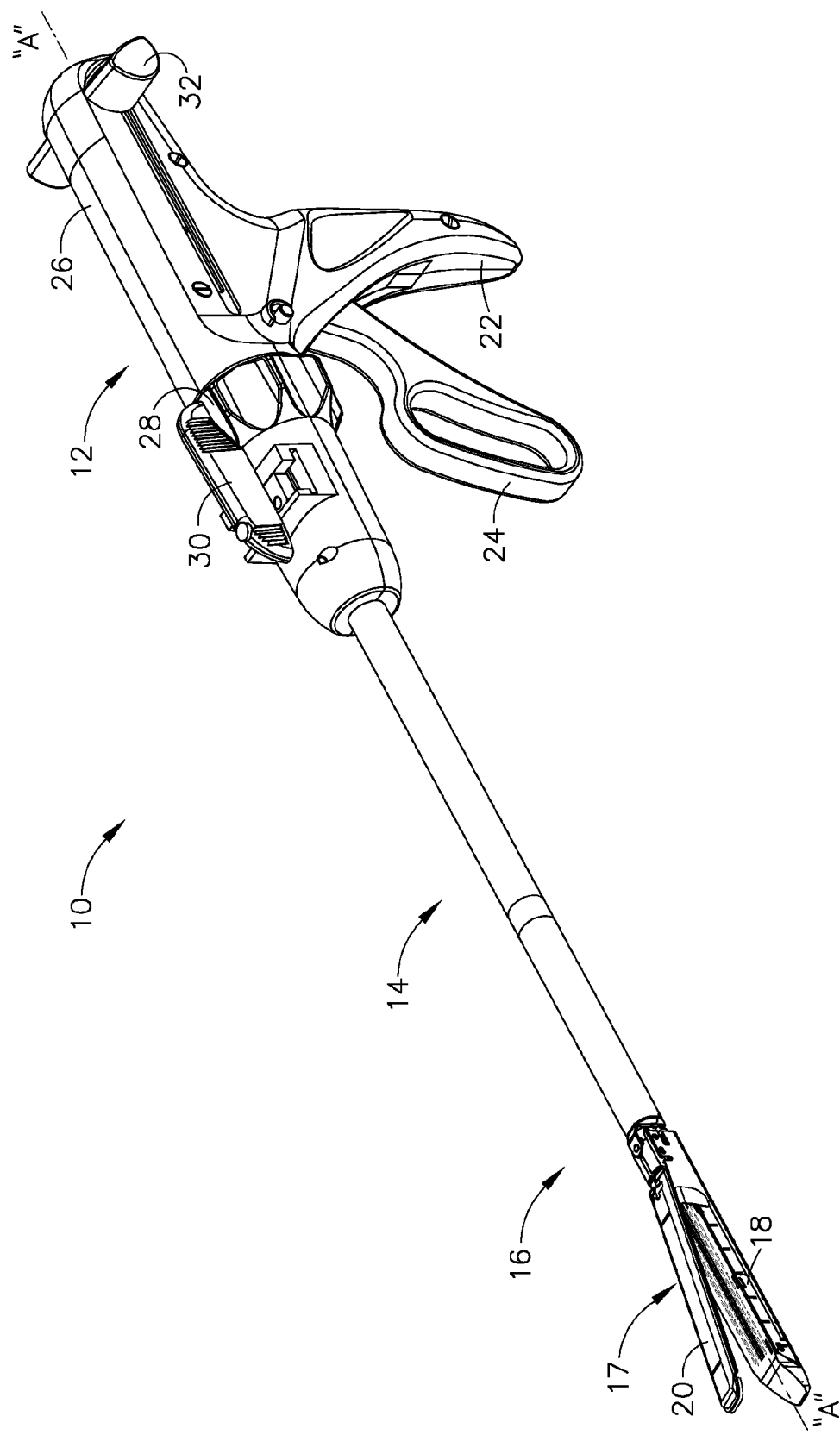
FIG. 29 is another perspective view of the surgical stapling instrument of FIG. 1.

FIGS. 11 and 28 illustrate one embodiment of a surgical stapling instrument. Briefly, the surgical stapling instrument includes a handle assembly 12 and an elongated shaft 14. A disposable loading unit or DLU 16 is releasably secured to a distal end of the shaft 14. Disposable loading unit 16 includes a tool assembly 17 having a cartridge assembly 18 housing, a plurality of surgical staples, and an anvil assembly 20 movably secured in relation to cartridge assembly 18. Disposable loading unit 16 is configured to apply linear rows of staples measuring from about 30 mm to about 60 mm in length. Disposable loading units having linear rows of staples of other lengths are also envisioned, e.g., 45 mm. Handle assembly 12 includes a stationary handle member 22, a movable handle member 24, and a barrel portion 26. A rotatable member 28 is mounted on the forward end of barrel portion 26 to facilitate rotation of elongated body 14 with respect to handle assembly 12. An articulation lever 30 is also mounted on the forward end of barrel portion 26 adjacent rotatable knob 28 to facilitate the articulation of tool assembly 17. A pair of retraction knobs 32 are movably positioned along barrel portion 26 to return surgical stapling apparatus 10 to a retracted position, as will be described in detail below.

Handle assembly 12 includes a housing which is formed from molded housing half-sections 36a and 36b, which forms stationary handle member 22 and barrel portion 26 of handle assembly 12 (See FIG. 1). Movable handle member 24 is pivotably supported between housing half-sections 36a and 36b about pivot pin 38. A biasing member 40, which is a torsion spring, biases movable handle 24 away from stationary handle 22. An actuation shaft 46 is supported within barrel portion 26 of housing 36 and includes a toothed rack 48. A driving pawl 42 having a rack engagement finger 43 with laterally extending wings 43a and 43b is pivotably mounted to one end of movable handle 24 about a pivot pin 44. A biasing member 50, which is also a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end 49 of a control rod 52 such that linear advancement of actuation shaft 46 causes corresponding linear advancement of control rod 52. A locking pawl 54 having a rack engagement member 55 is pivotably mounted within housing 36 about pivot pin 57 and is biased towards toothed rack 48 by biasing member 56, which is also a torsion spring. Engagement member 55 of locking pawl 54 is movable into engagement with toothed rack 48 to retain actuation shaft 46 in a longitudinally fixed position.

A retraction mechanism 58, which includes a pair of retractor knobs 32, is connected to the proximal end of actuation shaft 46 by a coupling rod 60. Coupling rod 60 includes right and left engagement portions 62a and 62b for receiving retractor knobs 32 and a central portion 62c which is dimensioned and configured to translate within a pair of longitudinal slots 34a formed in actuation shaft 46 adjacent the proximal end thereof. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion 62c of coupling rod 60, and elongated slots 34 (See FIG. 1) are defined in the barrel section 26 of handle assembly 12 to accommodate the longitudinal translation of coupling rod 60 as retraction knobs 32 are pulled rearwardly to retract actuation shaft 46 and thus retract control rod 52 rearwardly. Actuation shaft 46 is biased proximally by spring 72 which is secured at one end to coupling rod portion 62 via connector 74 and at the other end to post 76 on actuation shaft 46.

Further to the above, handle assembly 12 includes a firing lockout assembly 80 which includes a plunger 82 and a pivotable locking member 83. Plunger 82 is biased to a central position by biasing springs 84 and includes annular tapered camming surfaces 85. Each end of plunger 82 extends through housing 36 adjacent an upper end of stationary handle 22. Pivotable locking member 83 is pivotably attached at its distal end between housing half-sections 36a and 36b about pivot pin 86 and includes a locking surface 88 and proximal extension 90 having a slot 89 formed therein. Locking member 83 is biased by spring 92 counter-clockwise (as viewed in FIG. 11) to move locking surface 88 to a position to abut the distal end of actuation shaft 46 to prevent advancement of shaft 46 and subsequent firing of the stapling apparatus. Annular tapered camming surface 85 is positioned to extend into tapered slot 89 in proximal extension 90. Lateral movement of plunger 82 in either direction against the bias of either spring 84 moves tapered camming surface 85 into engagement with the sidewalls of tapered slot 89 to pivot locking member 83 clockwise about pivot pin 86, as viewed in FIG. 11, to move blocking surface 88 to a position to permit advancement of actuation shaft 46 and thus firing of stapling apparatus 10. Blocking surface 88 is retained in this position by recesses which receive the tapered tip of camming surface 85 to lock locking member 83 in a counter-clockwise position. Operation of firing lockout assembly 80 will be further illustrated below.

Further to the above, handle mechanism 12 also includes an anti-reverse clutch mechanism which includes a first gear 94 rotatably mounted on a first shaft 96, and second gear 98 mounted on a second shaft 100, and a slide plate (not illustrated) slidably mounted within housing 36. The slide plate includes an elongated slot dimensioned and configured to be slidably positioned about locking pawl pivot pin 57, a gear plate configured to mesh with the teeth of second gear 98, and a cam surface. In the retracted position, the cam surface of the slide plate engages locking pawl 54 to prevent locking pawl 54 from engaging toothed rack 48. Actuation shaft 46 includes a distal set of gear teeth spaced from the proximal set of gear teeth positioned to engage first gear 94 of actuation shaft 46 during movement of actuation shaft 46. When actuation shaft 46 is advanced by pivoting movable handle 24 about pivot pin 38, the distal gear teeth on actuation shaft 46 mesh with and rotate first gear 94 and first shaft 96. First shaft 96 is connected to second shaft 100 by spring clutch assembly such that rotation of first shaft 96 will cause corresponding rotation of second shaft 100. Rotation of second shaft 100 causes corresponding rotation of second gear 98 which is engaged with the gear plate on the slide plate to cause linear advancement of the slide plate. Linear advancement of the slide plate is limited to the length of elongated slot. When the slide plate has been advanced the length of the slot, the cam surface releases locking pawl 54 such that it is moved into engagement with toothed rack 48. Continued advancement of actuation shaft 46 eventually moves the distal gear teeth into engagement with the gear plate. However, since the slide plate is longitudinally fixed in position, the spring clutch is forced to release, such that continued distal advancement of actuation shaft 46 is permitted.

When actuation shaft 46 is returned to the retracted position (by pulling retraction knobs 34 proximally, as discussed above) the distal gear teeth engage first gear 94 to rotate second gear 98 in the reverse direction to retract the slide member proximally within housing 36. Proximal movement of the slide member advances the cam surface into locking pawl 54 prior to engagement between locking pawl 54 and toothed rack 48 to urge locking pawl 54 to a position to permit retraction of actuation shaft 46.

Referring again to FIG. 11, handle assembly 12 includes an emergency return button 112 pivotally mounted within housing 36 about a pivot member 114 supported between housing half-sections 36a and 36b. Return button 112 includes an externally positioned member 116 positioned on the proximal end of barrel portion 26. Member 116 is movable about pivot member 114 into engagement with the proximal end of locking pawl 54 to urge rack engagement member 55 out of engagement with toothed rack 48 to permit retraction of actuation shaft 46 during the firing stroke of the stapling apparatus 10.

Figure 12:
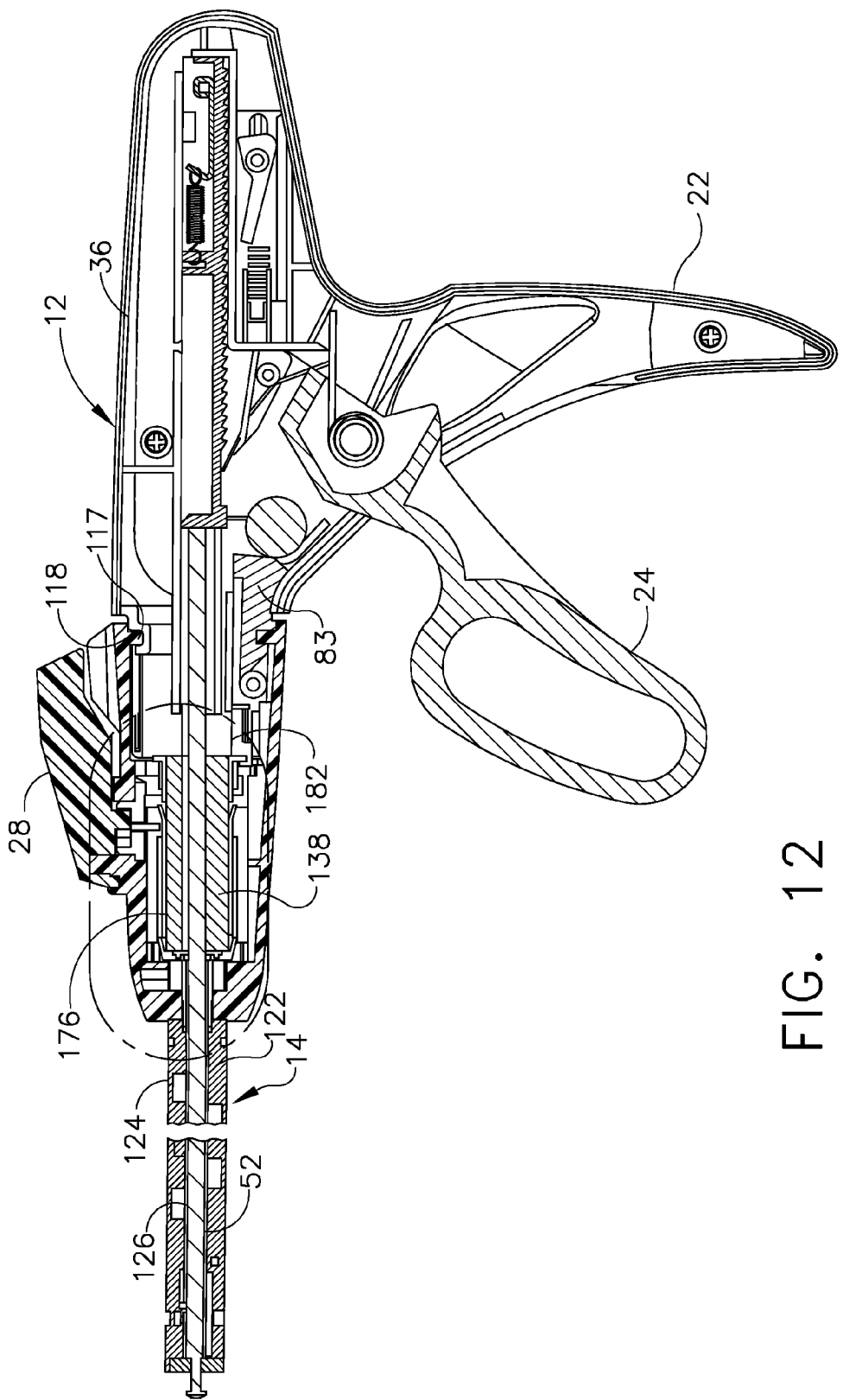
FIG. 12 is a side cross-sectional view of the surgical stapling instrument shown in FIG. 11 illustrating the handle assembly in a non-actuated position.
Figure 13:
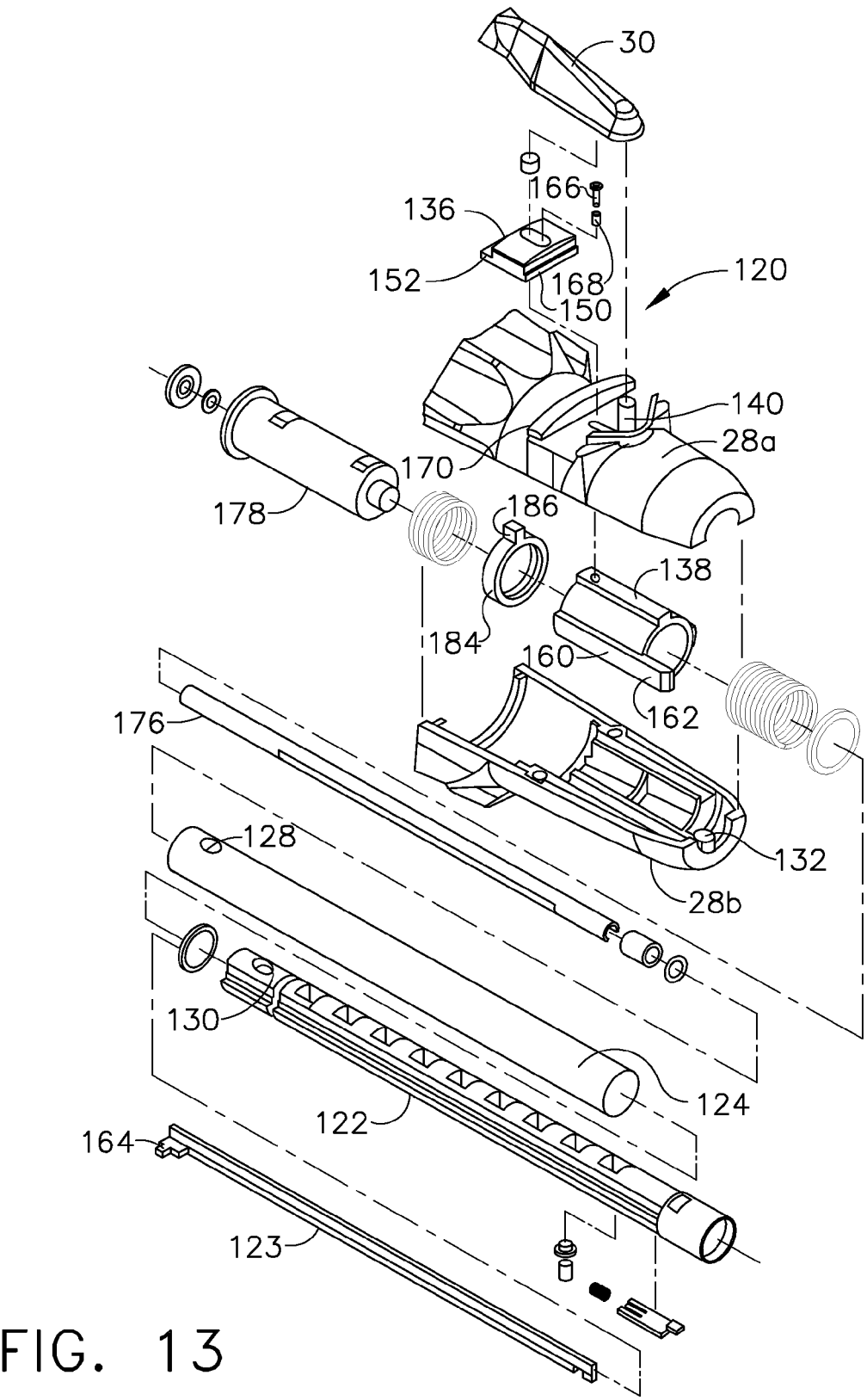
FIG. 13 is an exploded perspective view of a portion of the surgical stapling instrument shown in FIG. 11.
Figure 14:
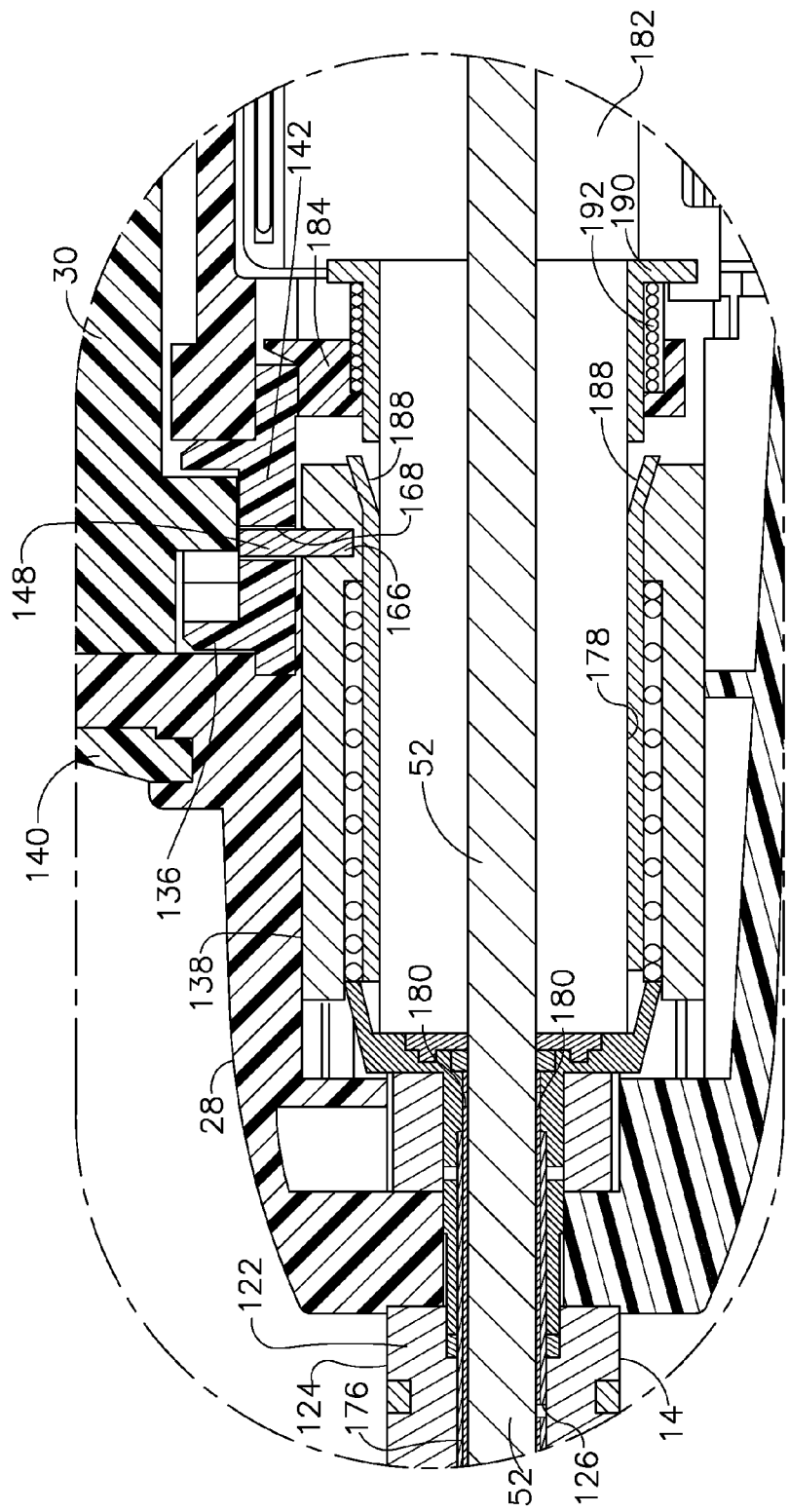
FIG. 14 is an enlarged view of the indicated area of detail shown in FIG. 12.
Figure 17:
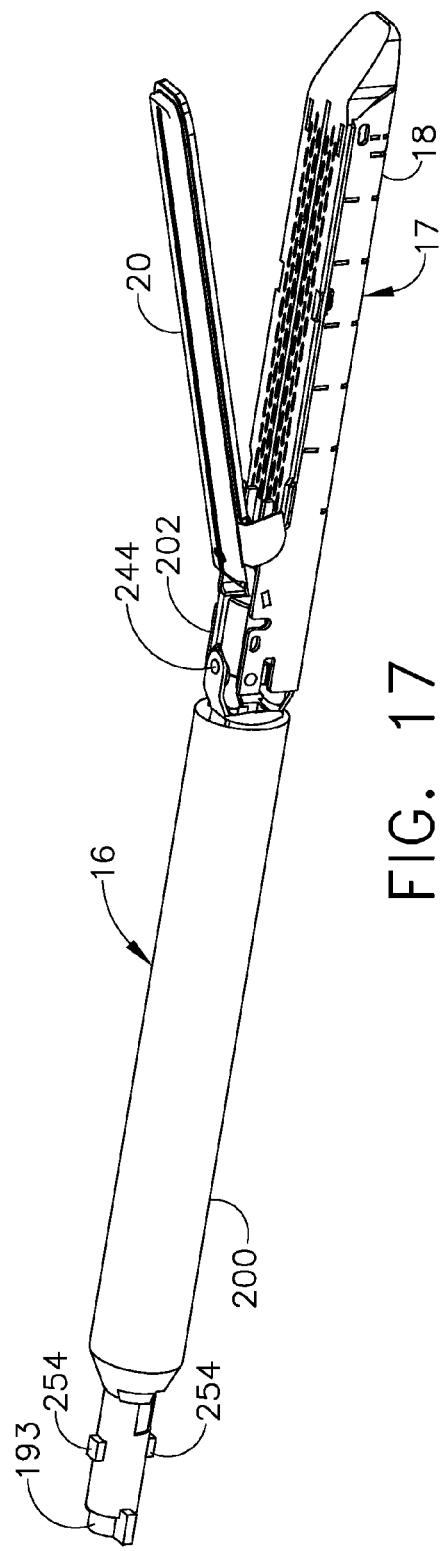
FIG. 17 is a perspective view of a disposable loading unit usable with the surgical stapling instrument of FIG. 11.
Figure 18:
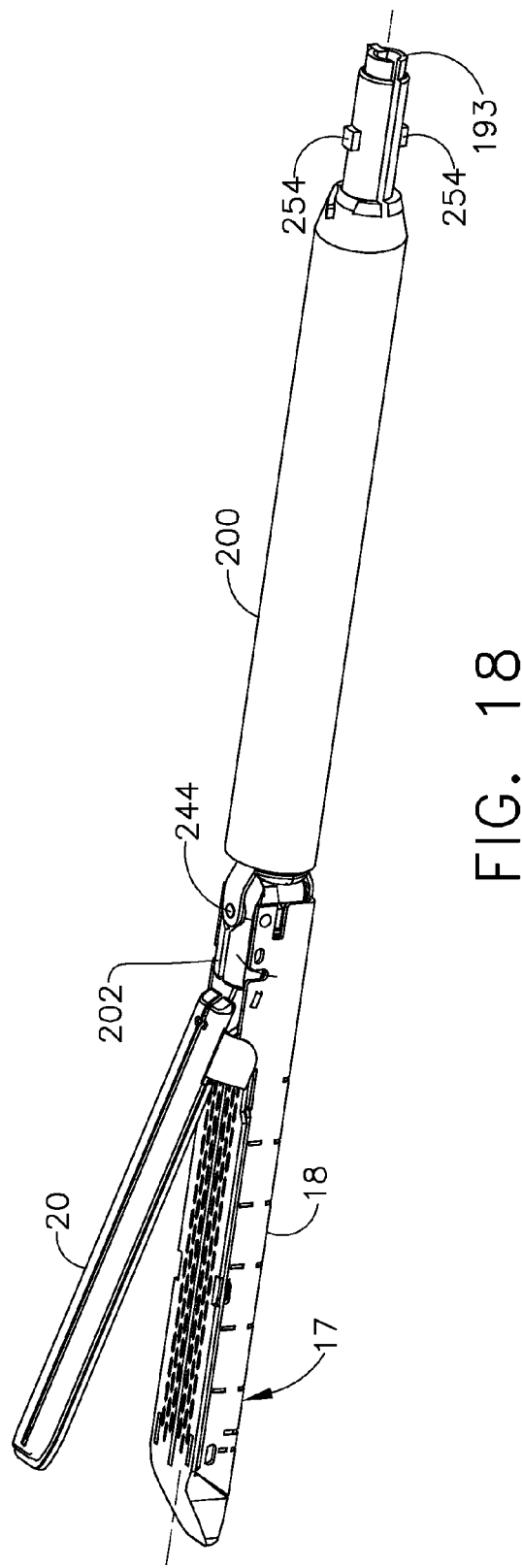
FIG. 18 is another perspective view of a disposable loading unit usable with the surgical stapling instrument of FIG. 11.
Figure 19:
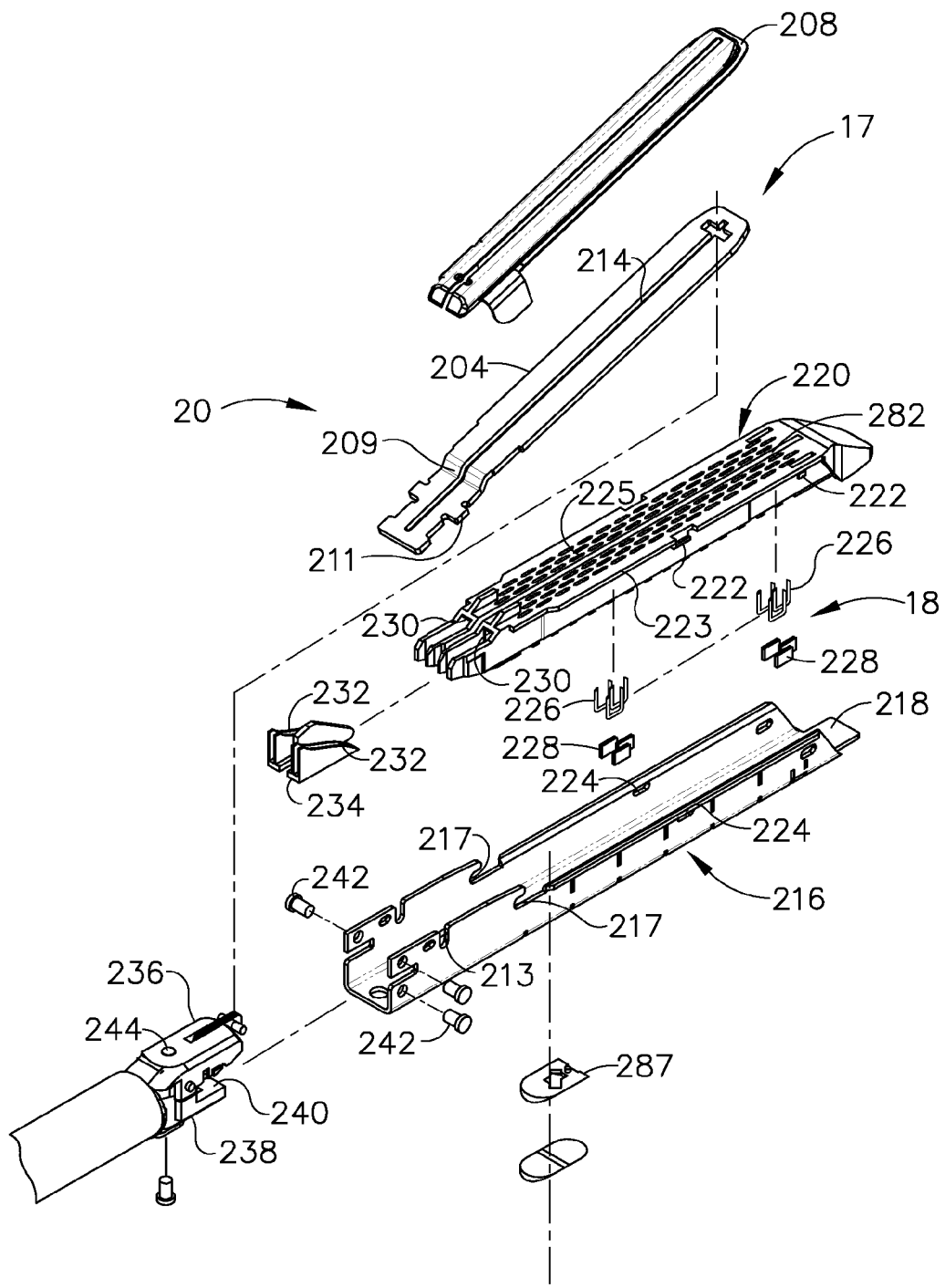
FIG. 19 is an exploded perspective view of an end effector for use with the surgical stapling instrument of FIG. 11.
Figure 22:
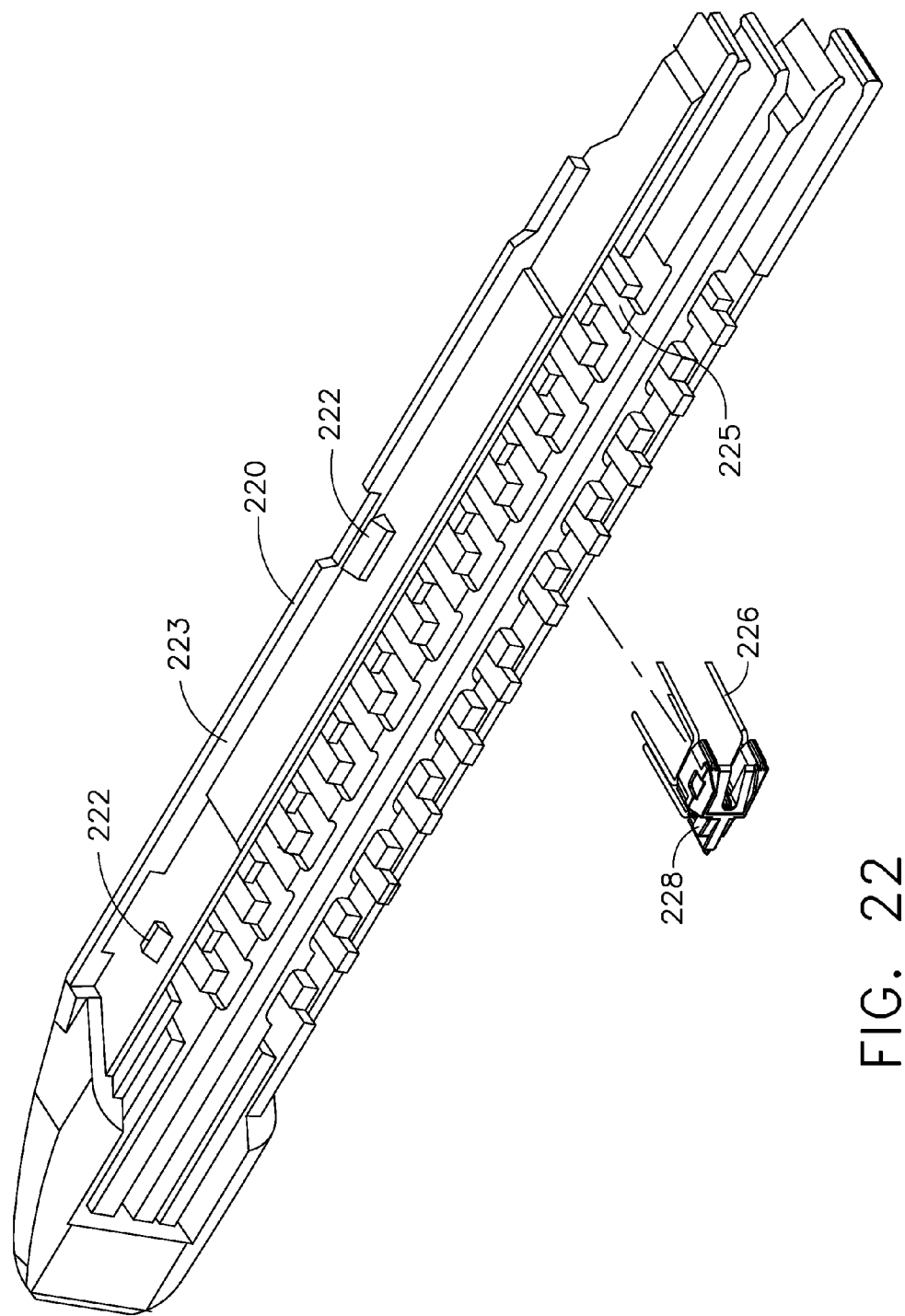
FIG. 22 is a bottom perspective view of the staple cartridge shown in FIG. 20.
Figure 23:
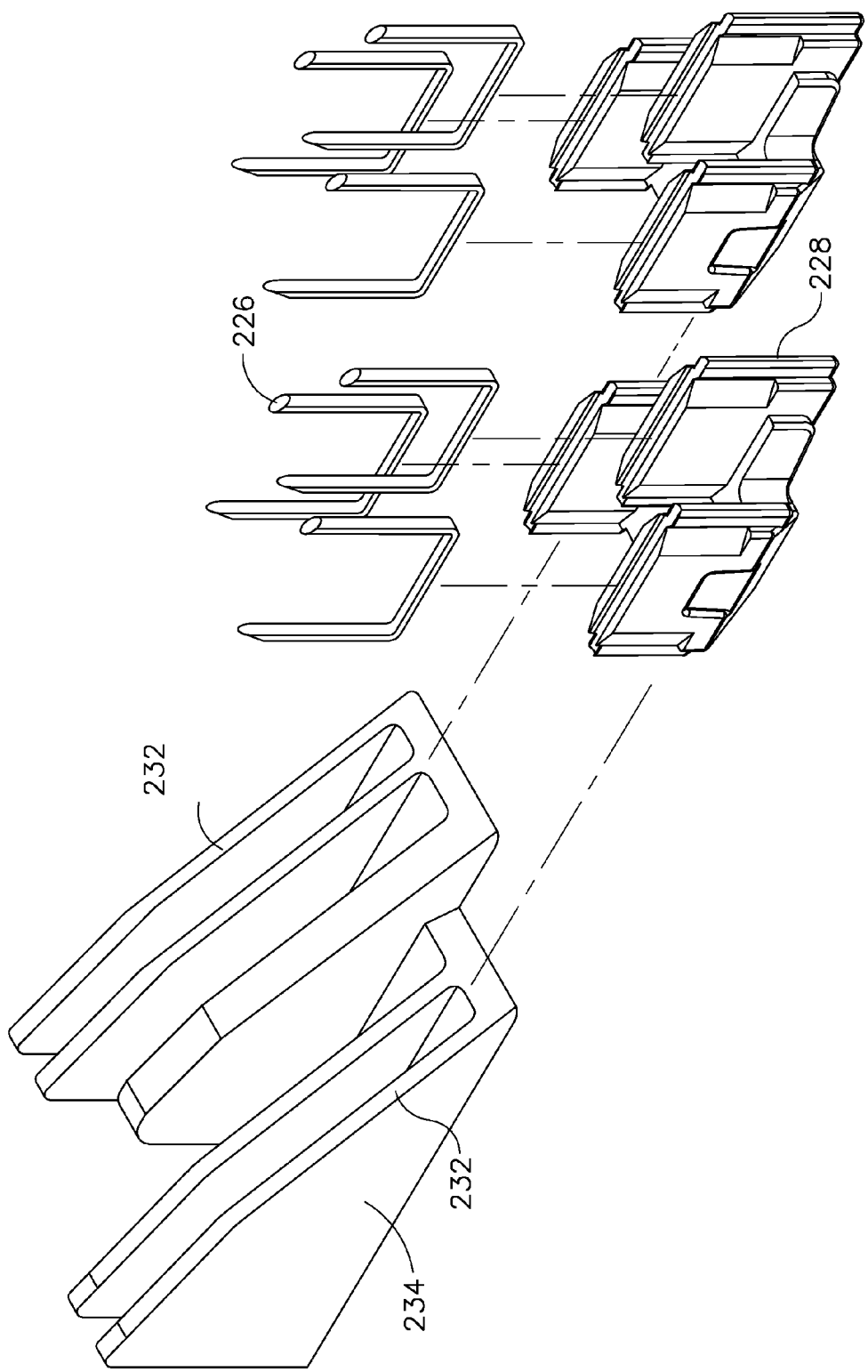
FIG. 23 is an enlarged perspective view of the actuation sled, the pushers and the fasteners shown in FIG. 21.
Figure 27:
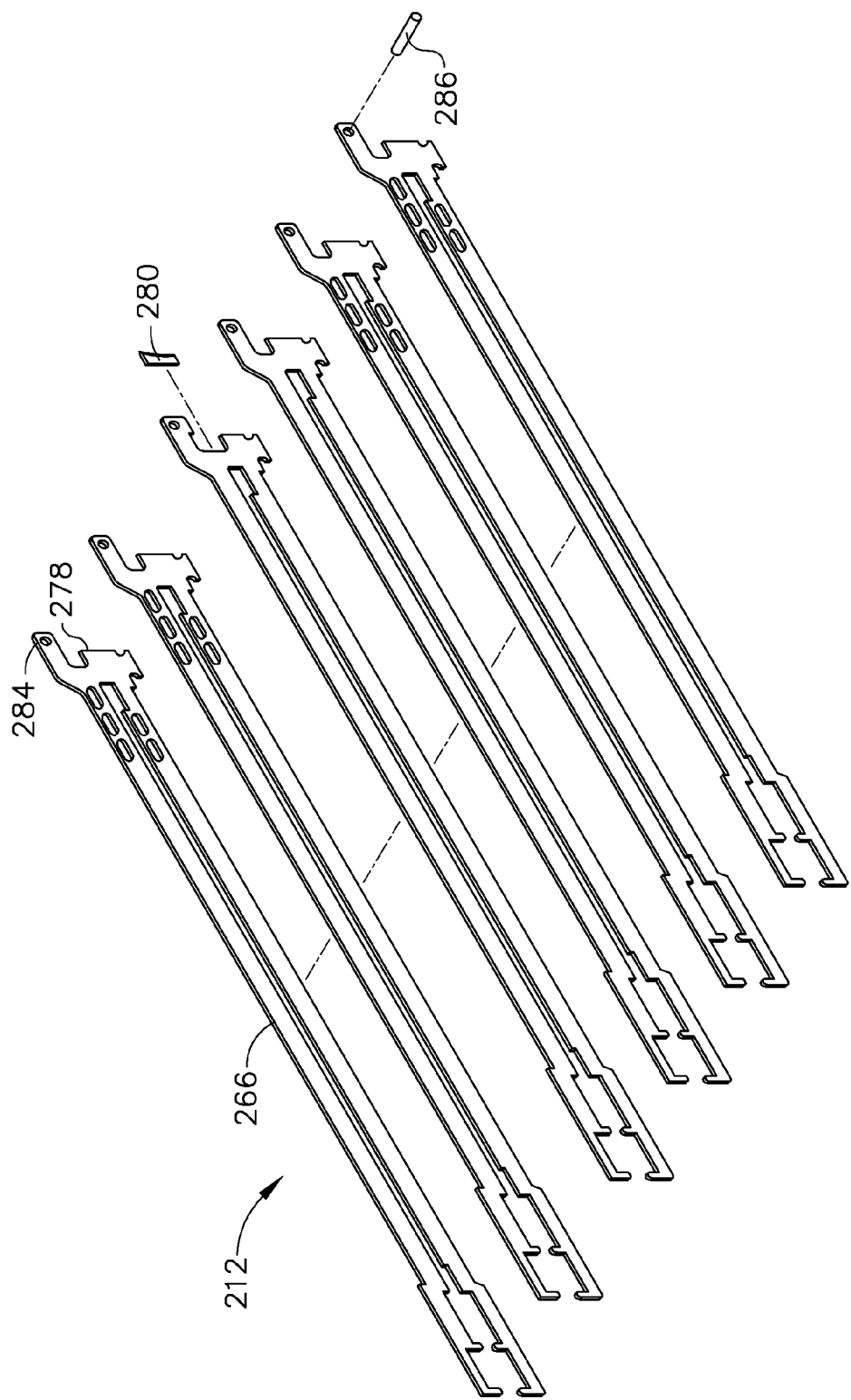
FIG. 27 is a perspective view with parts separated of an axial drive assembly.

As discussed above, during the clamping portion of advancement of actuation shaft 46, the slide plate disengages pawl 54 from rack 48 and thus actuation of return button 112 is not necessary to retract the actuation shaft 46. FIGS. 12-14 illustrate the interconnection of elongated body 14 and handle assembly 12. Housing 36 includes an annular channel 117 configured to receive an annular rib 118 formed on the proximal end of rotation member 28, which is formed from molded half-sections 28a and 28b. Annular channel 117 and rib 118 permit relative rotation between rotation member 28 and housing 36. Elongated body 14 includes inner housing 122 and an outer casing 124. Inner housing 122 is dimensioned to be received within outer casing 124 and includes an internal bore 126 which extends therethrough and is dimensioned to slidably receive a first articulation link 123 and control rod 52. The proximal end of housing 122 and casing 124 each include a pair of diametrically opposed openings 130 and 128, respectively, which are dimensioned to receive radial projections 132 formed on the distal end of rotation member 28. Projections 132 and openings 128 and 130 fixedly secure rotation member 28 and elongated body 14 in relation to each other, both longitudinally and rotatably. Rotation of rotation knob 28 with respect to handle assembly 12 thus results in corresponding rotation of elongated body 14 with respect to handle assembly 12.

An articulation mechanism 120 is supported on rotatable member 28 and includes articulation lever 30, a cam member 136, a translation member 138, and the first articulation link 123. Articulation lever 30 is pivotably mounted about pivot member 140 which extends outwardly from rotation member 28 and is formed integrally therewith. A projection 142 extends downwardly from articulation lever 30 for engagement with cam member 136. The distal end of translation member 138 includes arm 160 which includes an opening 162 configured to receive a finger 164 extending from the proximal end of articulation link 123. A pin 166 having a housing 168 constructed from a non-abrasive material, e.g., Teflon, is secured to translation member 138 and dimensioned to be received within a stepped camming surface. In an assembled condition, proximal and distal stepped portions 150 and 152 of cam member 136 are positioned beneath flanges, such as flange 170, formed on rotation member 28 to restrict cam member 136 to transverse movement with respect to the longitudinal axis of stapling apparatus 10. When articulation lever 30 is pivoted about pivot member 140, cam member 136 is moved transversely on rotation member 28 to move stepped camming surface 148 transversely relative to pin 166, forcing pin 166 to move proximally or distally along stepped cam surface 148. Since pin 166 is fixedly attached to translation member 138, translation member 138 is moved proximally or distally to effect corresponding proximal or distal movement of first actuation link 123.

A disposable loading unit sensing mechanism extends within the stapling instrument from elongated body 14 into handle assembly 12. The sensing mechanism includes a sensor tube 176 which is slidably supported within bore 26 of elongated body 14. The distal end of sensor tube 176 is positioned towards the distal end of elongated body 14 and the proximal end of sensor tube 176 is secured within the distal end of a sensor cylinder 178 via a pair of nubs 180. The distal end of a sensor link 182 is secured to the proximal end of sensor cylinder 178. Sensor link 182 has a bulbous end 184 which engages a camming surface on pivotable locking member 83. When a disposable loading unit is inserted in the distal end of elongated body 14, the disposable loading unit engages the distal end of sensor tube 176 to drive sensor tube 176 proximally, and thereby drive sensor cylinder 178 and sensor link 182 proximally. Movement of sensor link 182 proximally causes bulbous end 184 of sensor link 182 to move distally of the camming surface to allow locking member 83 to pivot under the bias of spring 92 from a position permitting firing of stapling apparatus 10 to a blocking position, wherein blocking member 83 is positioned to engage actuation shaft 46 and prevent firing of stapling apparatus 10. Sensor link 182 and locking member 83 function to prevent firing of surgical stapling apparatus 10 after a disposable loading unit has been secured to elongated body 14, without first operating firing lockout assembly 80.

Further to the above, cam member 136 can include a recess defined in the bottom portion thereof. A locking ring 184 having a nub portion 186 configured to be received within this recess can be positioned about sensor cylinder 178 between a control tab portion 188 and a proximal flange portion 190. A spring 192 positioned between flange portion 190 and locking ring 184 urges locking ring distally about sensor cylinder 178. When an articulating disposable loading unit having an extended insertion tip 193 (FIG. 16) is inserted into the distal end of elongated body 14 of stapling apparatus 10, insertion tip 193 causes tab portion 188 to move proximally into engagement with locking ring 184 to urge locking ring 184 and nub 186 proximally of recess 154 in cam member 136. With nub 186 positioned proximally of the recess in cam member 136, the cam member 136 is free to move transversely to effect articulation of stapling apparatus 10. A non-articulating disposable loading unit may not have an extended insertion tip. As such, when a non-articulating disposable loading unit is inserted in elongated body 14, sensor cylinder 178 is not retracted proximally a sufficient distance to move nub 186 from recess 154. Thus, cam member 136 is prevented from moving transversely by nub 186 of locking ring 184 which is positioned in the recess defined in the cam member 136 and articulation lever 30 is locked in its central position.

Referring to FIGS. 15-18, a disposable loading unit, such as disposable loading unit 16a and/or 16b, for example, includes a proximal housing portion 200 adapted to releasably engage the distal end of body portion 14. A mounting assembly 202 is pivotally secured to the distal end of housing portion 200, and is configured to receive the proximal end of tool assembly 17 such that pivotal movement of mounting assembly 202 about an axis perpendicular to the longitudinal axis of housing portion 200 effects articulation of tool assembly 17 about pivot pin 244. Housing portion 200 of disposable loading unit 16 can include, one, engagement nubs 254 for releasably engaging elongated shaft 14 and, two, an insertion tip 193. Nubs 254 form a bayonet type coupling with the distal end of shaft 14. A second articulation link is dimensioned to be slidably positioned within a slot 258 formed between housing halves of housing portion 200.

Referring to FIGS. 19-27, tool assembly 17 includes anvil assembly 20 and cartridge assembly 18. Anvil assembly 20 includes anvil portion 204 having a plurality of staple deforming concavities 206 and a cover plate 208 secured to a top surface of anvil portion 204 to define a cavity 210 therebetween. Cover plate 208 is provided to prevent pinching of tissue during clamping and firing of the surgical stapling apparatus. Cavity 210 is dimensioned to receive a distal end of an axial drive assembly 212. A longitudinal slot 214 extends through anvil portion 204 to facilitate passage of retention flange 284 of axial drive assembly 212 into the anvil cavity 210. A camming surface 209 formed on anvil portion 204 is positioned to engage axial drive assembly 212 to facilitate clamping of tissue 198. A pair of pivot members 211 formed on anvil portion 204 are positioned within slots 213 formed in carrier 216 to guide the anvil portion between the open and clamped positions. A pair of stabilizing members can engage a respective shoulder 217 formed on carrier 216 to prevent anvil portion 204 from sliding axially relative to staple cartridge 220 as camming surface 209 is deformed.

Cartridge assembly 18 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 are positioned to rest on side walls of carrier 216 to further stabilize staple cartridge 220 within support channel 218. Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280. During operation of the surgical stapler, actuation sled 234 translates through longitudinal slots 230 of staple cartridge 220 to advance cam wedges 232 into sequential contact with pushers 228, to cause pushers 228 to translate vertically within slots 225 and urge fasteners 226 from slots 225 into the staple deforming cavities 206 of anvil assembly 20.

Further to the above, the shaft of the surgical stapling instrument can include upper and lower mounting portions 236 and 238. Each mounting portion includes a threaded bore 240 on each side thereof dimensioned to receive threaded bolts 242 for securing the proximal end of carrier 216 thereto. A pair of centrally located pivot members 244 extends between upper and lower mounting portions via a pair of coupling members which engage the distal end of housing portion 200. Housing portion 200 of the disposable loading unit can include upper and lower housing halves contained within an outer casing 251. A second articulation link 256 is dimensioned to be slidably positioned within a slot formed between the housing halves. A pair of blow out plates 254 are positioned adjacent the distal end of housing portion 200 adjacent the distal end of axial drive assembly 212 to prevent outward bulging of drive assembly 212 during articulation of tool assembly 17. The second articulation link 256 includes at least one elongated metallic plate. Preferably, two or more metallic plates are stacked to form link 256. The proximal end of articulation link 256 includes a hook portion 258 configured to engage first articulation link 123 and the distal end includes a loop 260 dimensioned to engage a projection 262 formed on mounting assembly 202. Projection 262 is laterally offset from pivot pin 244 such that linear movement of second articulation link 256 causes mounting assembly 202 to pivot about pivot pins 244 to articulate tool assembly 17.

The distal end of drive beam 266 is defined by a vertical support strut 278 which supports a knife blade 280, and an abutment surface 283 which engages the central portion of actuation sled 234 during a stapling procedure. Surface 285 at the base of surface 283 is configured to receive a support member 287 slidably positioned along the bottom of the staple cartridge 220. Knife blade 280 is positioned to translate slightly behind actuation sled 234 through a central longitudinal slot 282 in staple cartridge 220 to form an incision between rows of stapled body tissue. A retention flange projects distally from the vertical strut and supports a cylindrical cam roller 286 at its distal end. Cam roller 286 is dimensioned and configured to engage cam surface 209 on anvil body 204 to clamp anvil portion 204 against body tissue.

Figure 30:
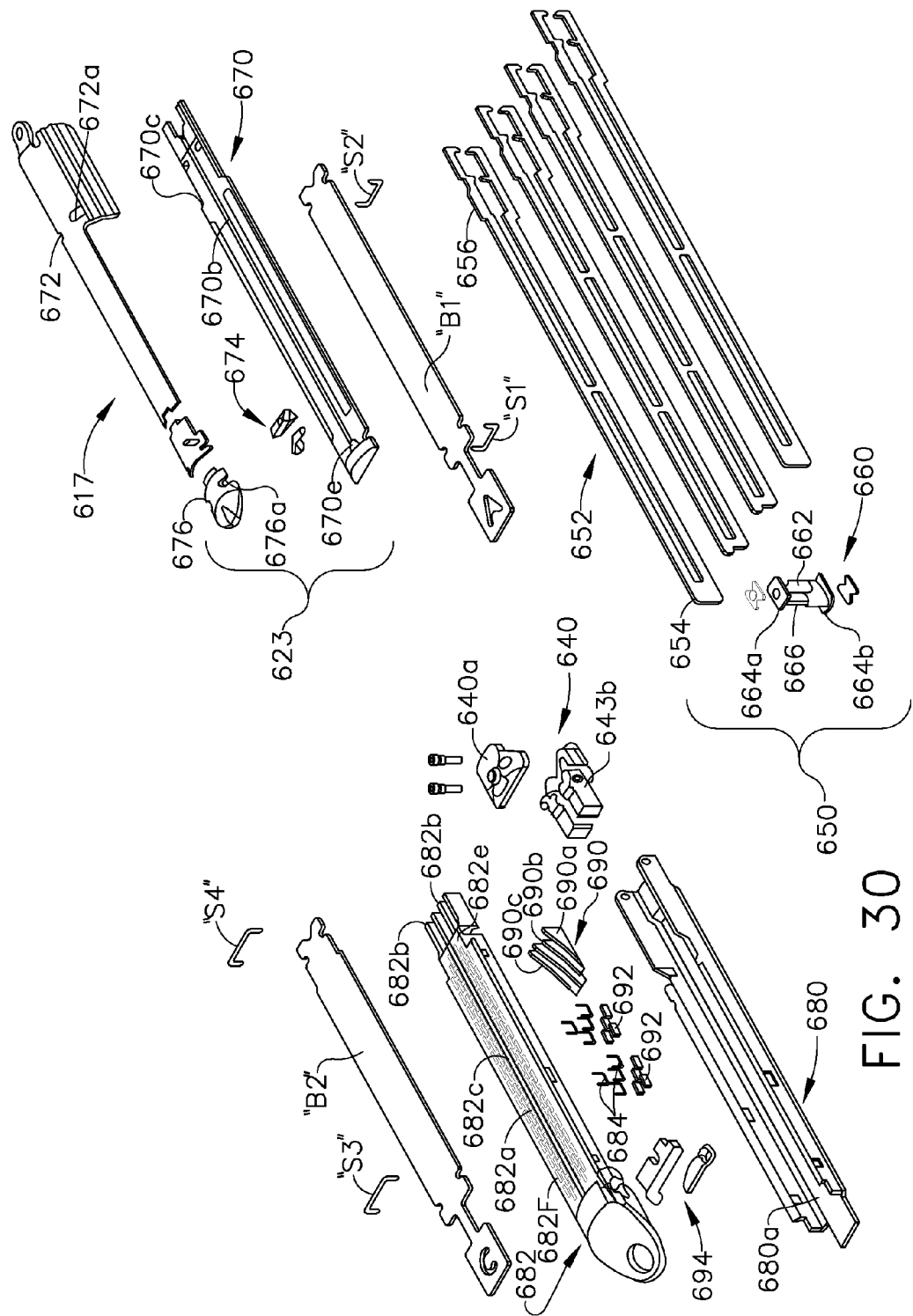
FIG. 30 is an exploded view of an end effector assembly for use with the surgical stapling instrument of FIG. 29.
Figure 31:
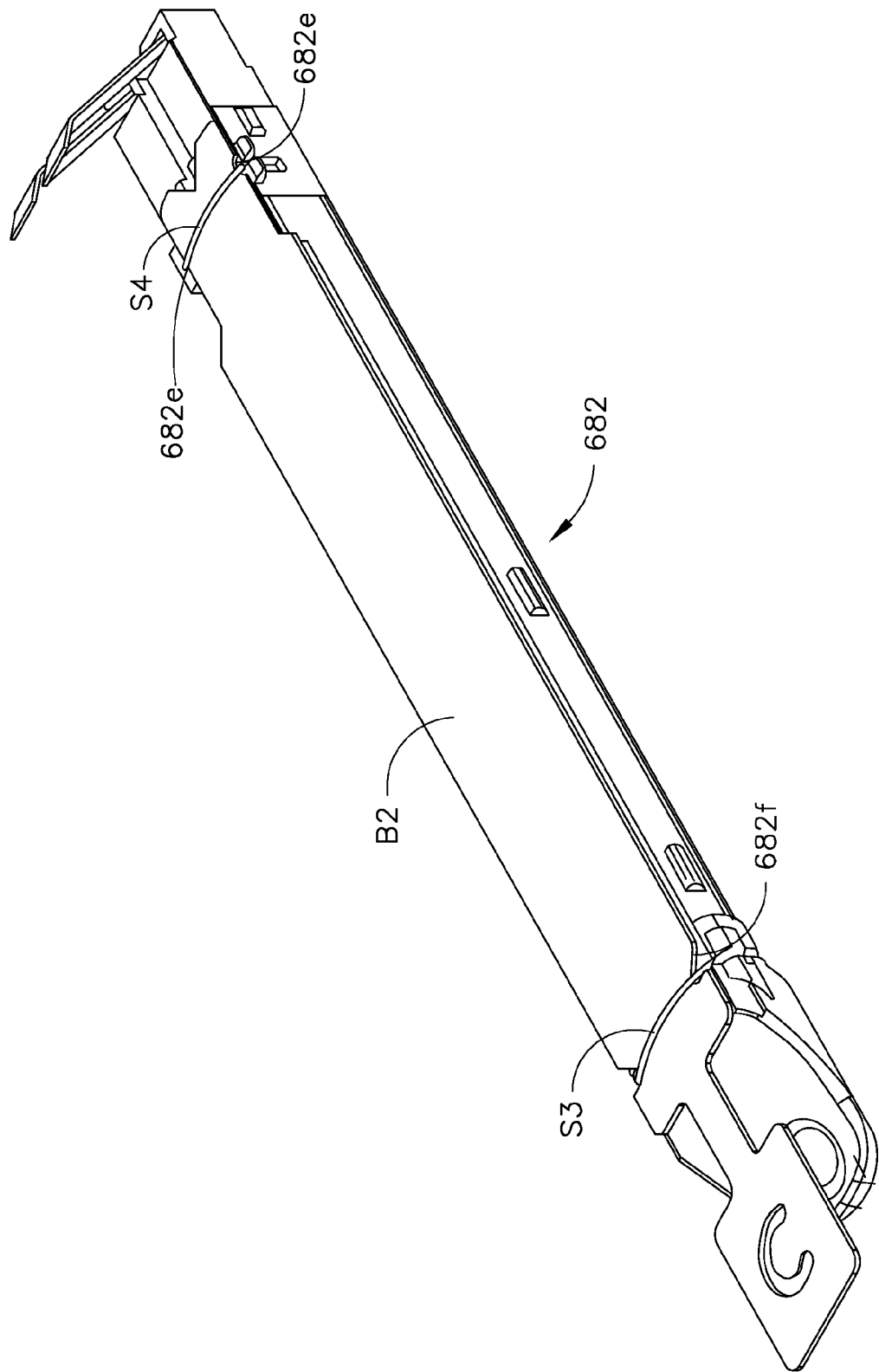
FIG. 31 is a perspective view of a staple cartridge portion of the end effector assembly of FIG. 30.

In various embodiments, referring now to FIGS. 30 and 31, an end effector of a surgical stapling instrument can comprise a first jaw 680 including a staple cartridge assembly and a second jaw 670. The first jaw 680 can include a pan 680a, a cartridge body 682 positionable in the pan 680a, and a sled 690 which is movable through the cartridge body 682 to lift drivers 692 toward deck 682a of cartridge body 682 and eject the staples 684 removably stored in staple cavities defined therein. The cartridge body 682 can further comprise a plurality of slots 682b which can each be configured to receive a cam of the sled 690, such as cams 690a-690c, for example, which can be configured to engage and lift the drivers 692. The staple cartridge assembly can further comprise a layer B2 which can be attached to the cartridge body 682 utilizing connectors S3 and S4. In various embodiments, each connector S3 and S4 can comprise a suture which ties the layer B2 to the cartridge body 682. For instance, the connector S3 can mount the distal end of the layer B2 to the distal end 682f of the cartridge body 682 while the connector S4 can mount the proximal end of the layer B2 to the proximal end 682e of the cartridge body 682. In use, a cutting member, such as cutting member 660, for example, can be advanced through the cartridge body 682 and incise, or otherwise deactivate, the connectors S3 and S4. For instance, the cutting member 660 can comprise a body 662, flanges 664a and 664b which are configured to engage the second jaw 670 and the first jaw 680, respectively, and a cutting member 66 which is configured to traverse a longitudinal slot 682c defined in the cartridge body 682a. The cutting member 660 can be advanced distally through the cartridge body 682 by a firing member assembly 650. The firing member assembly 650 can comprise a shaft 652 comprised of a plurality of layers including a distal end 654 engaged within the cutting member body 662 and a proximal end 656 configured to receive a firing force applied thereto.

When the firing force is applied to the firing member 650, further to the above, the flange 664a can engage the second jaw 670 and pivot the second jaw 670 downwardly toward the first jaw 680. The second jaw 670 can comprise an anvil assembly 623 which can include a frame 672 and an anvil plate including a plurality of anvil pockets defined therein. As the firing member 650 is being advanced distally, the cutting member 660 can pass through a longitudinal slot 670b defined in the anvil plate. Similar to the above, the second jaw 670 can further comprise a layer B1 attached thereto by one or more connectors, such as connectors S1 and S2, for example. Also similar to the above, the connectors S1 and S2 can each comprise a suture, wherein the connector S1 can be configured to releasably hold the distal end of the layer B1 to the distal end 670e of the anvil assembly 623 and wherein the connector S2 can be configured to releasably hold the distal end of the layer B2 to the proximal end 670c of the anvil assembly 623. In various embodiments, the anvil assembly 623 can comprise a distal nose 676 assembled to the frame 672 and can include a slot 676a defined therein which is configured to receive the connector S1. Similarly, the proximal end of the frame 672 can include a slot 672a defined therein which is configured to receive the connector S2. In either event, in various embodiments, the connectors S1 and S2 can extend around the entirety of the anvil frame 672 while, in other embodiments, the connectors S1 and S2 can engage the sides of the anvil assembly 623. When the cutting member 660 is advanced distally through the anvil assembly 623, the cutting member 660 can transect, or otherwise deactivate, the connectors S1 and S2 to release the layer B1 from the anvil assembly 623. More particularly, in various embodiments, the layer B1 can be positioned on one side of the patient tissue and the layer B2 can be positioned on the opposite side of the patient tissue, wherein the staples 684 can then be fired through the layer B2, the patient tissue, and the layer B1 when the firing member 650 is advanced distally. As the firing member 650 is advanced distally, the cutting member 660 can progressively transect the connectors S1-S4 as the layers B1 and B2 are progressively transected by the cutting member 660. For instance, the cutting member 660 can transect connectors S2 and S4 at the beginning of the stroke and connectors S1 and S3 at the end of the stroke. In various embodiments, referring now to FIGS. 32 and 33, an end effector 716 can comprise a first jaw 718 and a second jaw 720 wherein a connector 774 can be embedded within a slot 770e defined in an anvil 772 of the second jaw 720.

Figure 33A:
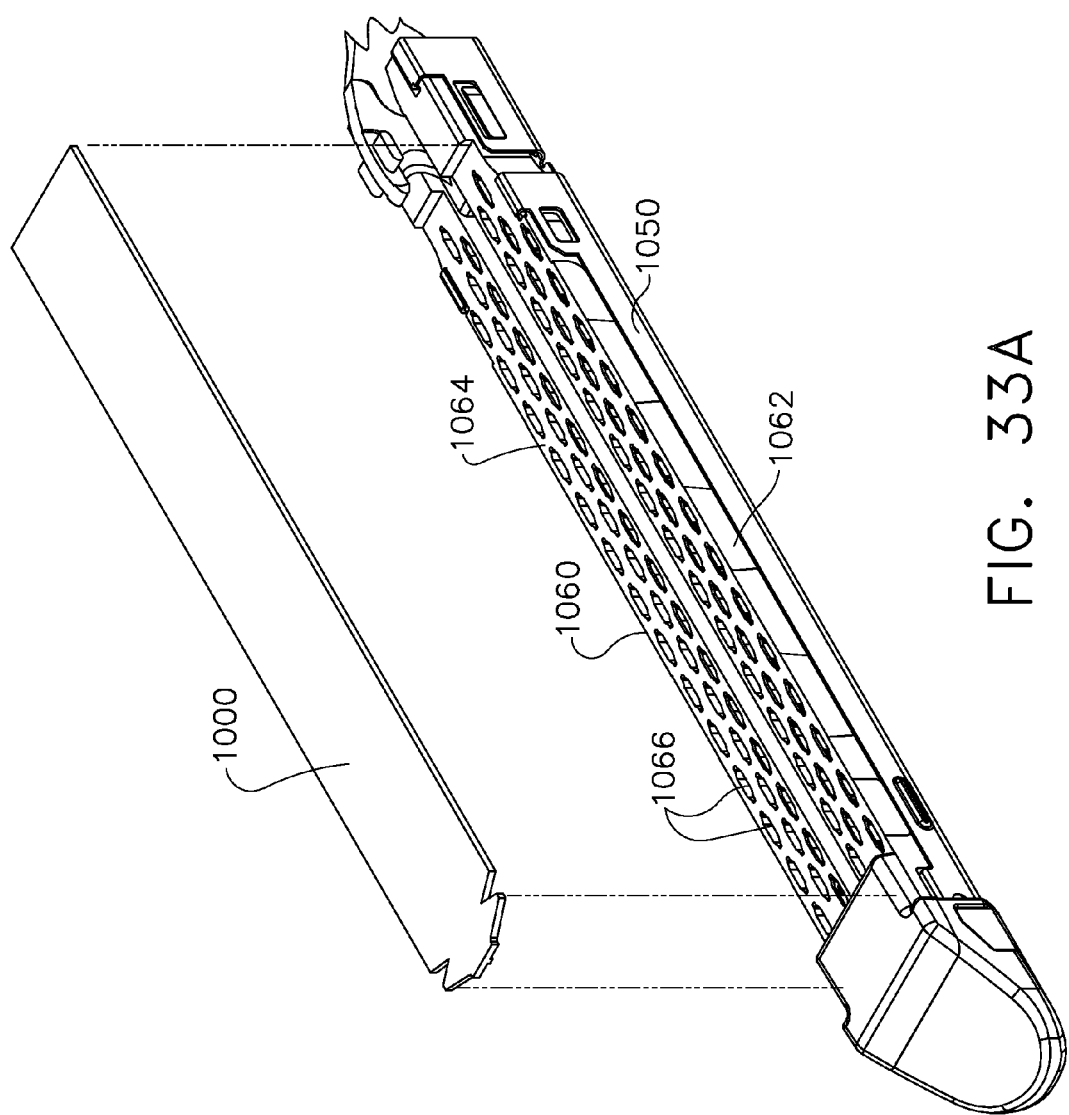
FIG. 33A is an exploded perspective view of an end effector of a stapling instrument comprising a staple cartridge and a tissue thickness compensator according to various embodiments.

Referring to FIG. 33A, an end effector of a surgical stapling instrument can comprise a first jaw and a second jaw, wherein at least one of the first jaw and the second jaw can be configured to be moved relative to the other. The end effector can comprise a first jaw including a staple cartridge channel 1050 and a second jaw including an anvil, wherein the anvil can be pivoted toward and/or away from the staple cartridge channel 1050, for example. In various alternative embodiments, the first jaw including a staple cartridge thereto can be pivoted toward and/or away from the second jaw including the anvil. In either event, the staple cartridge channel 1050 can be configured to receive a staple cartridge 1060, for example, which can be removably retained within the staple cartridge channel 1050. The staple cartridge 1060 can comprise a cartridge body 1062, a cartridge deck 1064, and a tissue thickness compensator 1000 wherein, as illustrated in FIG. 33A, tissue thickness compensator 1000 may be removably positioned against or adjacent cartridge deck 1064. Similar to other embodiments described herein, referring now to FIGS. 33A and 34, the cartridge body 1062 can comprise a plurality of staple cavities 1066 and a staple 1002 positioned within each staple cavity 1066. Also similar to other embodiments described herein, the staples 1002 can be supported by staple drivers positioned within the cartridge body 1062 wherein a sled and/or firing member, for example, can be advanced through the staple cartridge 1060 to lift the staple drivers upwardly within the staple cavities 1066 and eject the staples 1002 from the staple cavities 1066.

Figure 34:
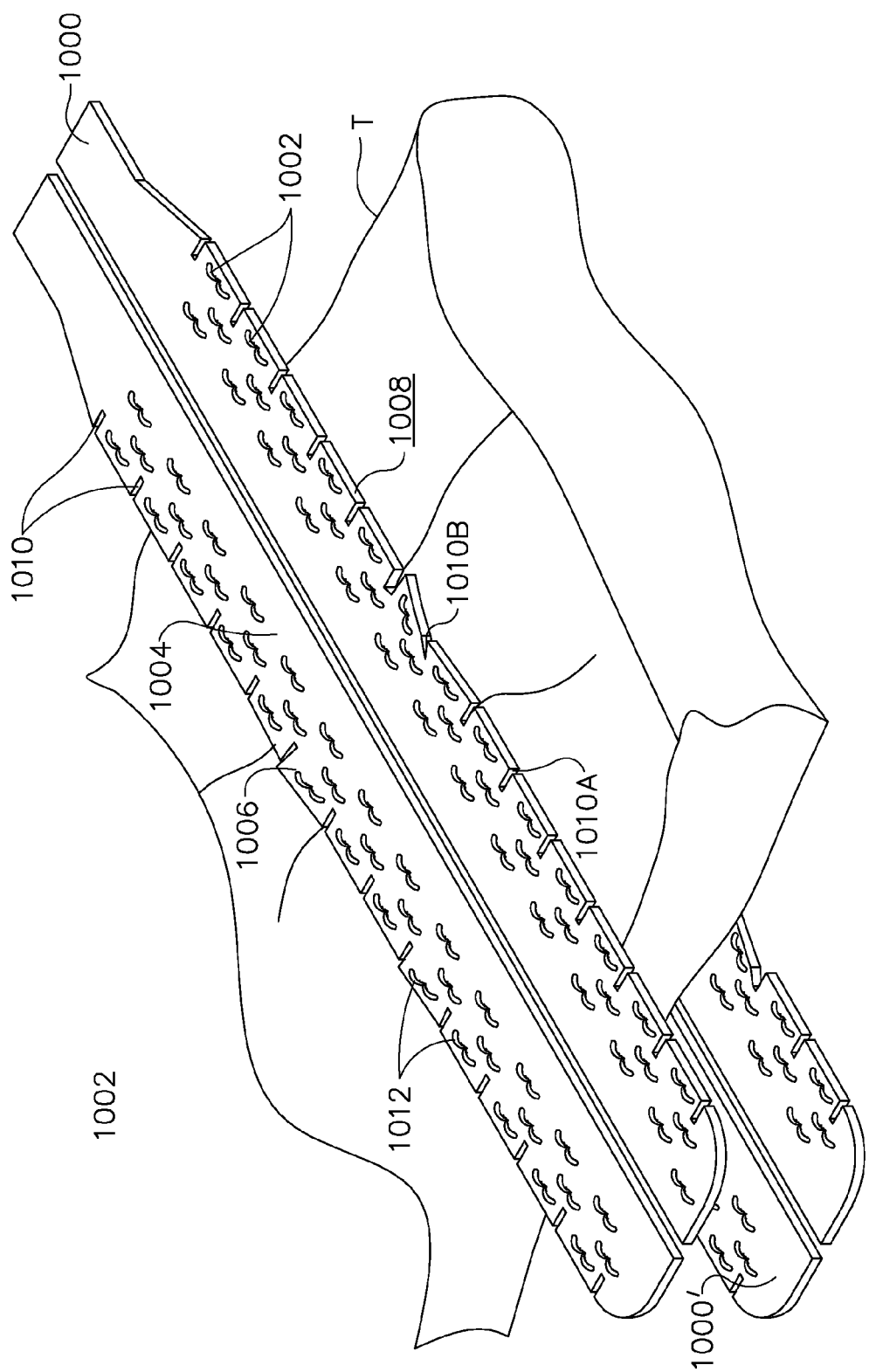
FIG. 34 is a perspective view of tissue thickness compensators fastened to tissue according to various embodiments.

Referring to FIG. 34, tissue thickness compensators, such as tissue thickness compensators 1000 and 1000', can be fastened to tissue T in order, for example, to provide support for fastened tissue T. As illustrated in FIG. 34, tissue thickness compensators 1000 and 1000' can be fastened to opposite sides of tissue T. A tissue thickness compensator such as, for example, tissue thickness compensator 1000, may comprise an inner portion 1004 and an outer portion 1006 which may form an outer perimeter at least partially surrounding the inner portion 1004. The outer portion 1006 may be more flexible than the inner portion 1004. In various circumstances, the outer portion 1006 may comprise sufficient flexibility to provide an atraumatic tissue contacting surface for tissue T, and the inner portion may comprise sufficient rigidity to provide adequate support for fastened tissue T.

Referring again to FIG. 34, the outer portion 1006 of tissue thickness compensator 1000 may include an outer edge 1008. To improve its flexibility, the outer portion 1006 may include multiple slits 1010. In addition, pieces of the outer edge 1008 and the outer portion 1006 can be cut or removed to improve the flexibility of the outer portion 1006. As illustrated in FIG. 34, slits 1010 can begin at the outer edge 1008 and can follow various paths terminating within the outer portion 1006. For example, a slit, such as slit 1010A, may begin at the outer edge 1008 then follow a path substantially perpendicular to the outer edge 1008 terminating within the outer portion 1006. In another example, a slit, such as slit 10108, may also begin at the outer edge 1008 then follow a path at an acute angle with the outer edge 1008, also terminating within the outer portion 1006. Tissue thickness compensator 1000 can be manufactured with slits 1010 in the outer portion 1006. Alternatively, tissue thickness compensator 1000 can be manufactured without the slits 1010, which can be incorporated into the outer portion 1006 prior to the implantation thereof, for example.

As described above, and as illustrated in FIG. 34, staples 1002 can be configured to at least partially capture tissue thickness compensator 1000 when the staples 1002 are moved from their unfired positions to their fired positions. Furthermore, staples 1002 can be fired in rows and each row may include multiple staples 1002. A row of staples 1002, for example row 1012, can be fastened onto the outer portion 1006 of tissue thickness compensator 1000 such that slits 1010 may be positioned between the staples 1002 of row 1012 to allow for sufficient support for the staples 1002 while maintaining an adequate flexibility within the outer portion 1006. Alternatively, under certain circumstances, slits 1010 can be positioned within the staples 1002, for example, to provide flexibility within the staples 1002.

Figure 35:
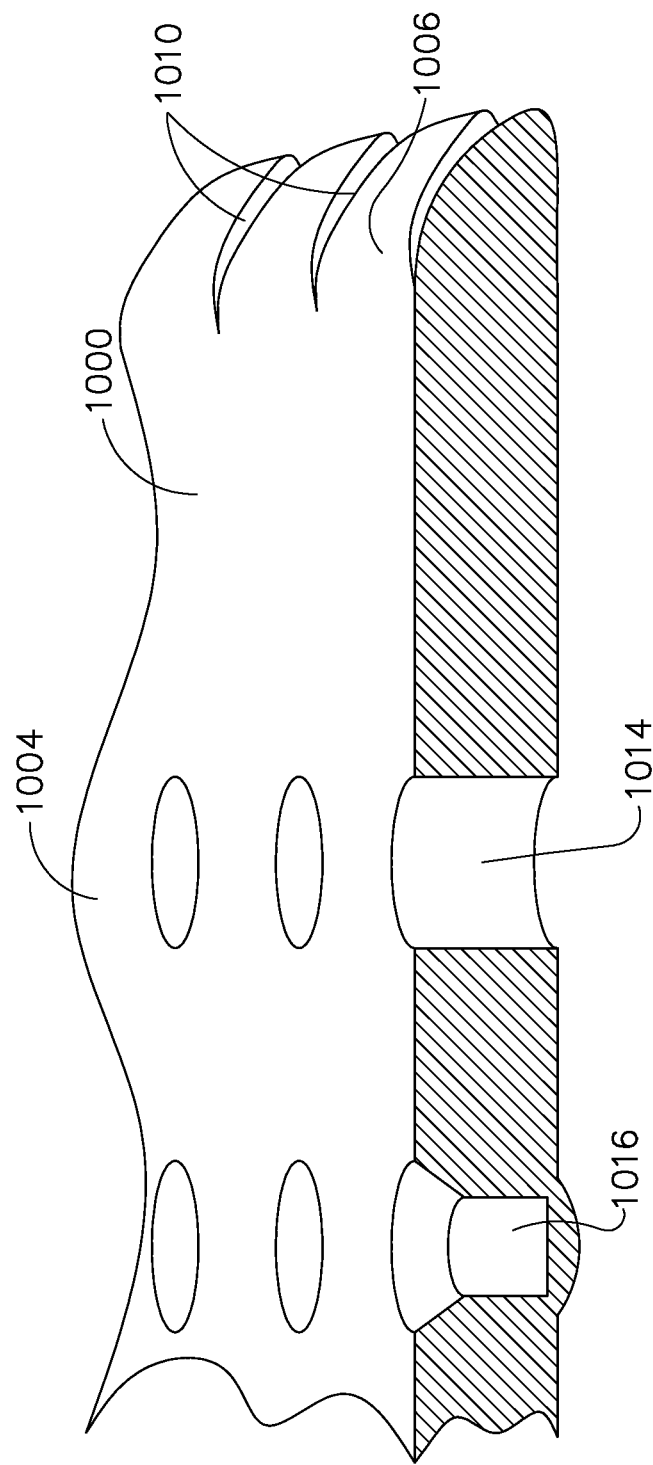
FIG. 35 is a partial cross sectional view of a tissue thickness compensator including a plurality of openings and a plurality of cavities according to various embodiments.

Referring now to FIG. 35, tissue thickness compensator 1000 may include a plurality of openings 1014 extending therethrough. As illustrated in FIG. 35, the openings 1014 may comprise generally cylindrical shapes. Alternatively, openings 1014 may comprise cone shapes which can be narrow on one side and wide on the other side of tissue thickness compensator 1000. Other geometrical shapes for openings 1014 are contemplated within the scope of this disclosure. Tissue thickness compensator 1000 may also include multiple cavities 1016. As illustrated in FIG. 35, cavities 1016 may comprise generally cylindrical shapes, sometimes with tapered outer portions. Other geometrical shapes for cavities 1016 are contemplated within the scope of this disclosure. For example cavities 1016 can include closed ended cones. Openings 1014 and/or cavities 1016 may provide regions of localized flexibility within tissue thickness compensator 1000 and can be positioned within the outer portion 1006, the inner portion 1004 and/or both portions 1004 and 1006 to enhance the flexibility of the tissue thickness compensator 1000. Furthermore, as illustrated in FIG. 35, tissue thickness compensator 1000 can include combinations of slits 1010, openings 1014, and/or cavities 1016 to yield a desired degree of flexibility.

Referring now to FIGS. 36-39, to improve its flexibility, the thickness of the tissue thickness compensator 1000 can include patterns that may provide regions of localized flexibility. Such patterns can be embossed patterns which can be molded or carved into the tissue thickness compensator 1000. As illustrated in FIG. 36, tissue thickness compensator 1000 can include a pattern 1020 comprising a plurality of pyramids 1018 which can be arranged, for example, in rows. Pyramids 1018, as illustrated in FIG. 37, can be separated from each by a distance "D." The degree of flexibility of tissue thickness compensator 1000 can, in part, be controlled by increasing or decreasing distance "D" between pyramids 1018. Pyramids 1018 can be arranged in other pattern arrangements which are contemplated within the scope of the present disclosure. In addition, other geometrical shapes, cones for example, and combinations thereof can also be used and are contemplated within the scope of the present disclosure. As illustrated in FIG. 38, tissue thickness compensator 1000 may comprise a corrugated pattern 1022. FIG. 38 shows a cross sectional view of corrugated pattern 1022 of tissue thickness compensator 1000 which may include multiple peaks 1024 and multiple valleys 1026. The various patterns illustrated herein and combinations thereof can be positioned within the outer portion 1006 and/or the inner portion 1004 to enhance the flexibility of the tissue thickness compensator 1000.

Further to the above, referring to FIGS. 40 and 41, the outer edge 1008 of tissue thickness compensator 1000 can comprise a generally atraumatic profile which can minimize an impact upon tissue T, for example, during and/or after the capturing of the tissue T and the tissue thickness compensator 1000 by staples 1002. For example, as illustrated in FIGS. 40 and 41, outer edge 1008 can comprise a generally scalloped profile. Other atraumatic profiles such as a feathered profile, for example, for the outer edge 1008 are also contemplated within the scope of the current disclosure. In addition, tissue thickness compensator 1000 may also comprise an atraumatic nose portion 1028 and/or an atraumatic tail portion 1030. As illustrated in FIGS. 40 and 41, atraumatic nose portion 1028 can comprise, for example, a generally curved shape and atraumatic tail portion 1030 may, for example, comprise a split tail with flexible ends 1032. Other atraumatic shapes for the nose portion 1028 and/or the tail portion 1030 are also contemplated within the scope of the current disclosure.

Referring again to FIGS. 40 and 41, tissue thickness compensator 1000 can comprise a gripping member 1034, which can reduce slippage between the tissue thickness compensator 1000 and the cartridge deck 1064 when the tissue thickness compensator 1000 is placed against the cartridge deck 1064. As illustrated in FIG. 40, gripping member 1034 can comprise multiple cylindrically shaped protrusions 1036, for example, which can be joined with corresponding recesses in the cartridge deck 1064. Gripping member 1034, as illustrated in FIG. 41, can comprise an arrow head shaped protrusion 1038 which can be matted with a corresponding recess in the cartridge deck 1064. Other gripping means for gripping tissue thickness compensator 1000 to cartridge deck 1064 are contemplated within the scope of the present disclosure. Gripping member 1034, as illustrated in FIGS. 40 and 41, can be positioned in the nose portion 1028. Alternatively, gripping member 1034 can be positioned in other portions of tissue thickness compensator 1000 such as, for example, tail portion 1030.

Figure 42:
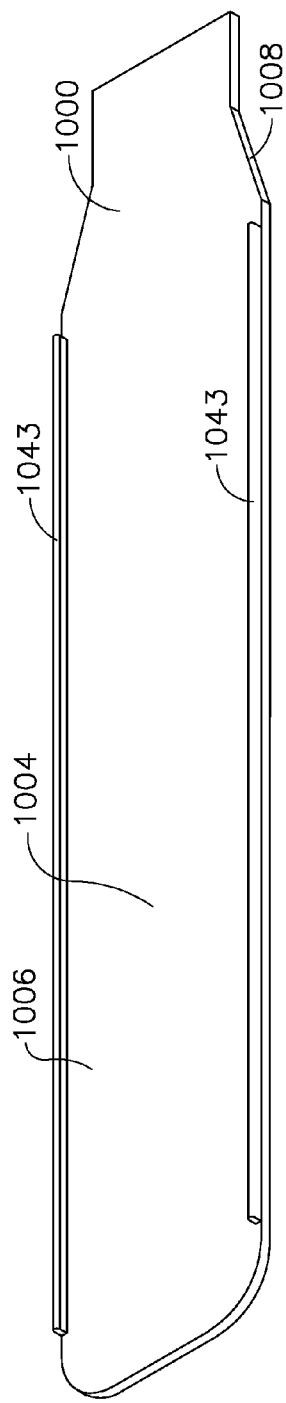
FIG. 42 is a perspective view of a tissue thickness compensator including a cushioning member according to various embodiments.
Figure 43:
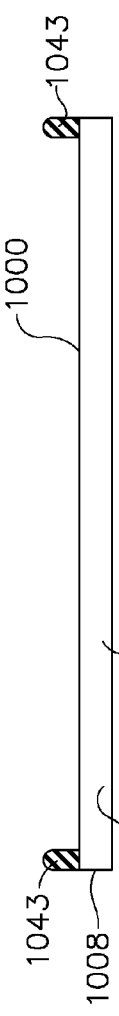
FIG. 43 is a cross sectional view of the tissue thickness compensator in FIG. 42.
Figure 44:
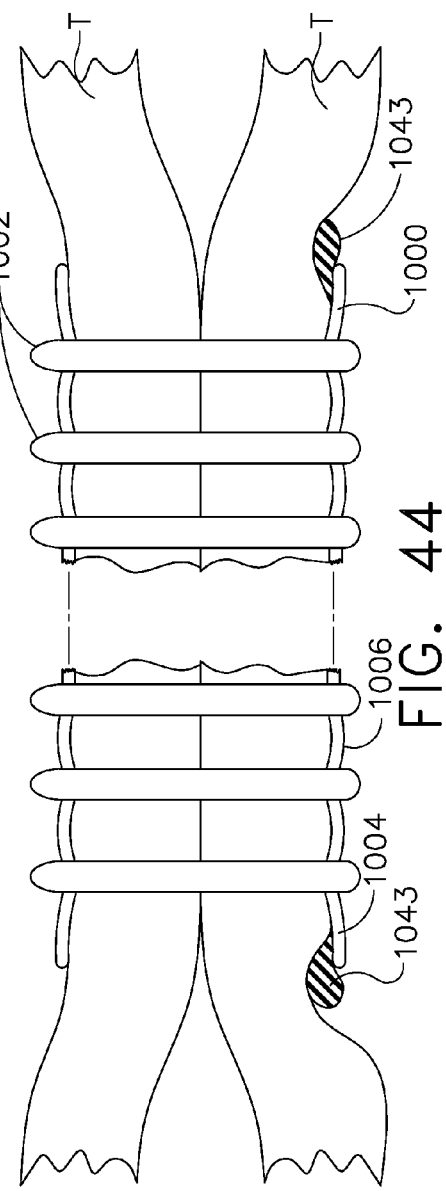
FIG. 44 is a cross sectional view of the tissue thickness compensator of FIG. 42 fastened to tissue according to various embodiments.

Referring now to FIGS. 42-44, outer portion 1006 of tissue thickness compensator 1000 can comprise a cushioning member 1043 which can provide a pliable edge that contacts tissue T, for example, during and/or after the capturing of the tissue T and the tissue thickness compensator 1000 by staples 1002. In at least one embodiment, as illustrated in FIG. 44, cushioning member 1043 may comprise sufficient structural elasticity to collapse and/or bend when compressed against the tissue T. As illustrated in FIG. 43, cushioning member 1043 can partially extend over the outer edge 1008 and may be attached to outer edge 1008 by an adhesive, for example. Other attachment means for attaching cushioning member 1043 to outer edge 1008 are contemplated within the scope of the current disclosure. Alternatively, cushioning member 1043 can be an integral part of tissue thickness compensator 1000 that may be manufactured therewith. Cushioning member 1043 may comprise a biocompatible foam which can be comprised of a biodegradable material such as, for example, PGA, PCL, PLLA, and/or combinations thereof, for example. Furthermore, cushioning member 1043 may be comprised, at least in part, of alginate and/or oxidized regenerated cellulose (ORC). For example, cushioning member 1043 may include a plurality of alginate and/or ORC beads which may soften upon implantation in a patient which may increase the softness of cushioning member 1043.

The outer edge 1008 of the compensator 1000 may comprise a thickness greater than the thickness of the outer portion 1006. The greater thickness of the outer edge 1008 may provide an atraumatic surface that contacts tissue T. Referring to FIGS. 45 and 46, outer portion 1006 of tissue thickness compensator 1000 can comprise a rolled outer edge 1046 which can be at least partially extended around outer portion 1006 and inwardly rolled towards the inner portion 1004. Similar to the above, rolled outer edge 1046 can provide a pliable outer edge that contacts tissue T, for example, during and/or after the capturing of the tissue T and the tissue thickness compensator 1000 by staples 1002.

Figure 47:
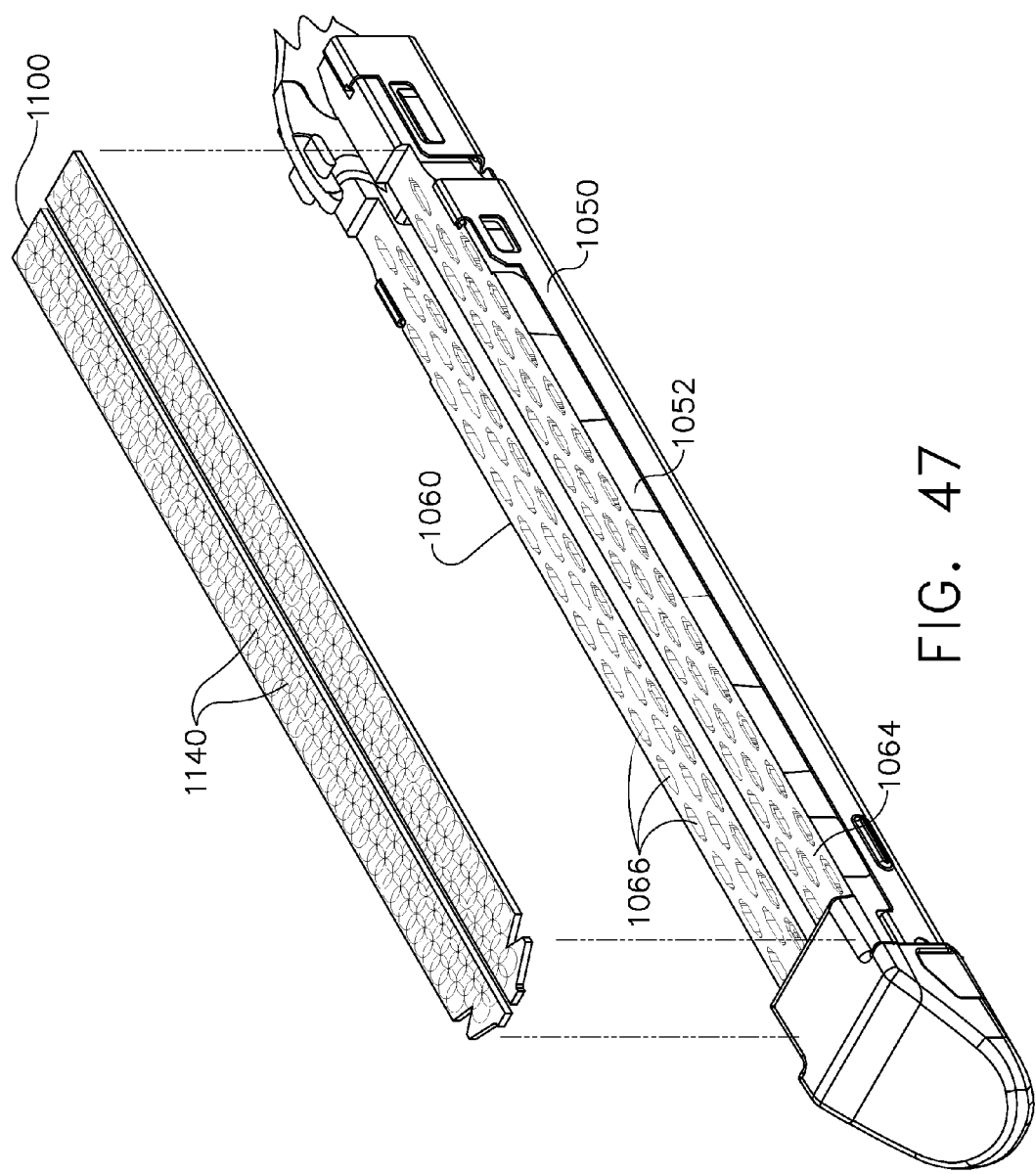
FIG. 47 is an exploded perspective view of an end effector of a stapling instrument comprising a staple cartridge and a tissue thickness compensator according to various embodiments.
Figure 48:
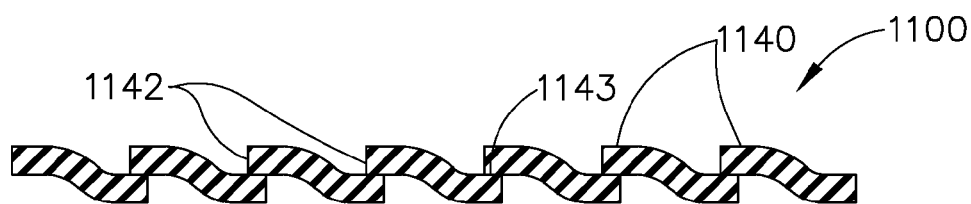
FIG. 48 is a cross sectional view of the tissue thickness compensator in FIG. 47 according to various embodiments.
Figure 49:
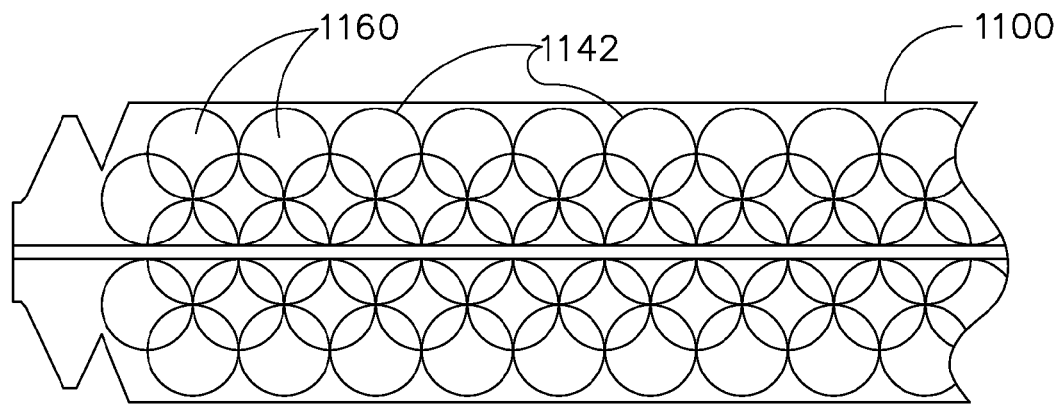
FIG. 49 is a top view of a tissue thickness compensator including a plurality of circular pieces according to various embodiments.

Referring to FIGS. 47-49, as described above, the staple cartridge channel 1050 can be configured to receive a staple cartridge 1060 which can comprise a cartridge body 1062, a cartridge deck 1064. In addition, a tissue thickness compensator such as, for example, tissue thickness compensator 1100 may be removably positioned against or adjacent cartridge deck 1064, as illustrated in FIG. 47.

Referring again to FIGS. 47-49, a tissue thickness compensator may be configured to be absorbed after implantation in a patient. The absorption process may initially reduce the tissue thickness compensator into smaller pieces which may include rough edges that may have undesirable effects on surrounding tissue T. To mitigate these effects, tissue thickness compensator 1100 may be at least partially assembled from a plurality of pieces 1140, which each may have atraumatic outer peripheries and may be joined together to form a single structure, as illustrated in FIG. 48. Pieces 1140 can be joined to form tissue thickness compensator 1100 in a manner such that the absorption process may first reduce tissue thickness compensator 1100 into pieces 1140 thereby minimizing the presence of rough edges. For example, pieces 1140 may comprise circular profiles and may be joined together by thermal bonding to form tissue thickness compensator 1100. Other profiles and other means for joining pieces 1140 are contemplated within the scope of the present disclosure. In one example, pieces 1140 can be joined together by an adhesive 1143 (See FIG. 48) configured to be absorbed faster than pieces 1140 to allow separation of the pieces 1140 in an initial stage of the absorption process. As illustrated in FIG. 48, pieces 1140 can be arranged in an overlapping array wherein an end portion of one of the pieces 1140 may overlap with an end portion of another one of the pieces 1140 such that the two end portions of the pieces 1140 are releasably attached to each other, for example, by an adhesive. Under certain circumstances, pieces 1140 can be arranged in another overlapping array wherein one of the pieces 1140 can be positioned over and releasably attached to a plurality of pieces 1140, as illustrated in FIG. 49.

Figure 50:
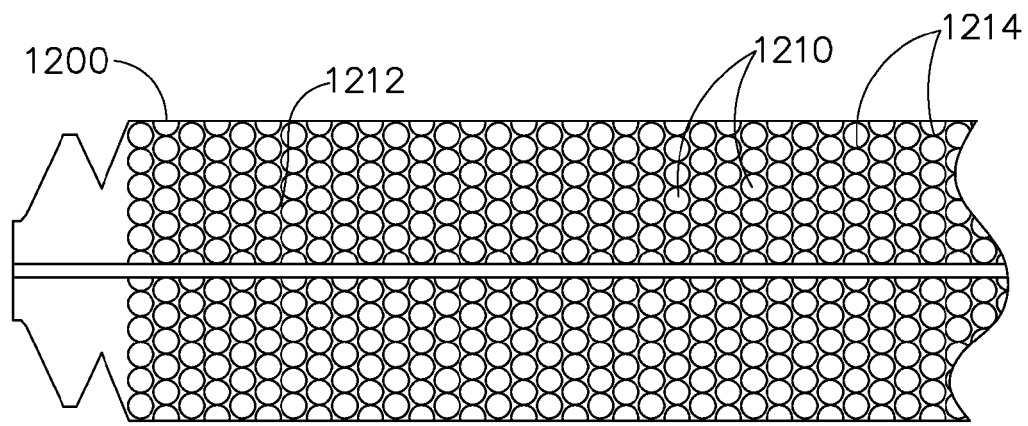
FIG. 50 is a top view of a tissue thickness compensator including a plurality of circular pieces according to various embodiments.
Figure 51:
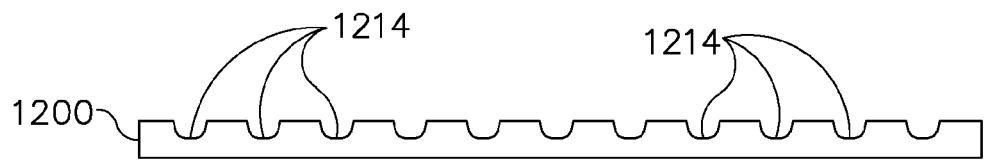
FIG. 51 is a cross sectional view of a tissue thickness compensator according to various embodiments.
Figure 52:
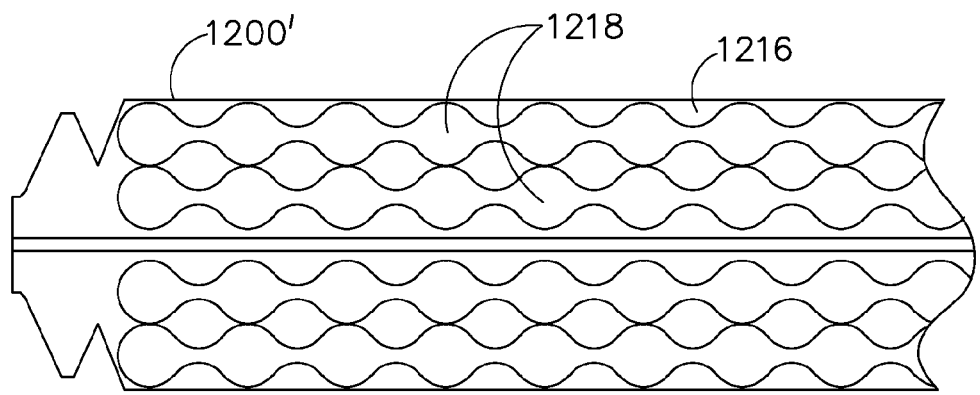
FIG. 52 is a top view of a tissue thickness compensator according to various embodiments.
Figure 53:
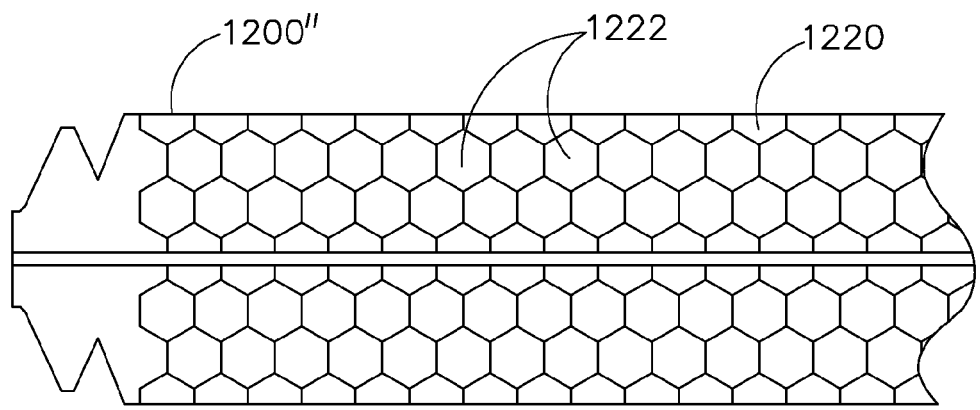
FIG. 53 is a top view of a tissue thickness compensator including a plurality of hexagonal pieces according to various embodiments.

Referring to FIGS. 50-53, as described above, a tissue thickness compensator may be configured to be absorbed after implantation in a patient and the absorption process may initially reduce the tissue thickness compensator into random smaller pieces. Guiding the absorption process to yield small pieces with atraumatic outer edges can be achieved, as described above, by starting with small pieces having atraumatic outer edges. Another approach may include modifying the tissue thickness compensator in such a manner that allows its separation into smaller pieces having atraumatic peripheries in an initial stage of the absorption process. For example, as illustrated in FIG. 50, a tissue thickness compensator 1200 may comprise a pattern such as pattern 1212, for example, which can be molded or carved into the tissue thickness compensator 1200 to yield, for example, a plurality of circular shaped portions 1210. The portions 1210 may be defined by reducing the thickness of tissue thickness compensator 1200 along circumferences 1214 of the circular shaped portions 1210, as illustrated in the cross-sectional view in FIG. 51. In result, a faster absorption along the circumferences 1214 of circular shaped portions 1210 may occur which may lead to a separation of the circular shaped portions 1210 from each other in an initial stage of the absorption process. Patterns comprising portions with other geometrical shapes with atraumatic outer peripheries are contemplated within the scope of the current disclosure. For example, as illustrated in FIG. 52, tissue thickness compensator 1200' may comprise a pattern 1216 comprising portions 1218 which may include profiles that extend longitudinally in a wave-like profile along a length of tissue thickness compensator 1200'. In another example, as illustrated in FIG. 53, tissue thickness compensator 1200" may comprise a pattern 1220 which may include hexagonal shaped portions 1222.

Figure 54:
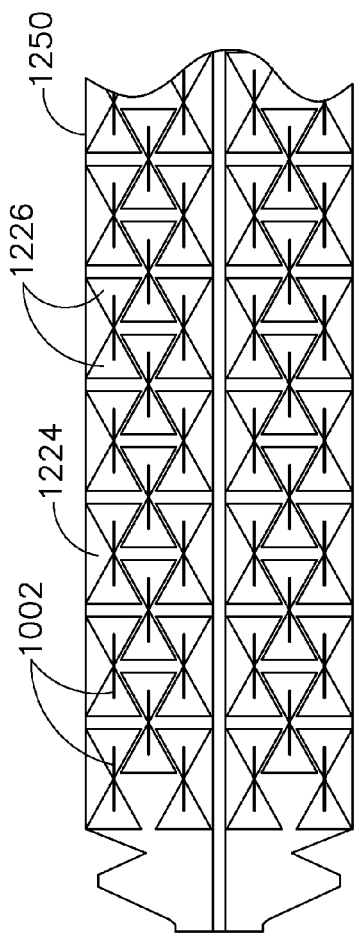
FIG. 54 is a top view of a fastened tissue thickness compensator including a plurality of pieces according to various embodiments.

Referring to FIG. 54, as described above, a tissue thickness compensator, such as tissue thickness compensator 1250, may be captured along with tissue T by staples, such as staples 1002, for example, and may be configured to be reduced into atraumatic pieces, such as pieces 1226, for example, in an initial stage of the absorption process after implantation in a patient. Upon separation, pieces 1226 can move and/or slide relative to each other which may impact surrounding tissue T. To minimize relative motion between pieces 1226, fired staples 1002 can be spatially arranged onto tissue thickness compensator 1250 such that a staple 1002 may capture multiple pieces 1226, as illustrated in FIG. 54. This may also aid in maintaining tissue thickness compensator 1250 in a substantially singular structure even after pieces 1226 are separated from each other in the initial stage of the absorption process. As such, the tissue thickness compensator 1250 may continue to provide support for tissue T captured by staples 1002 after pieces 1226 are separated from each other in the initial stage of the absorption process.

Figure 55:
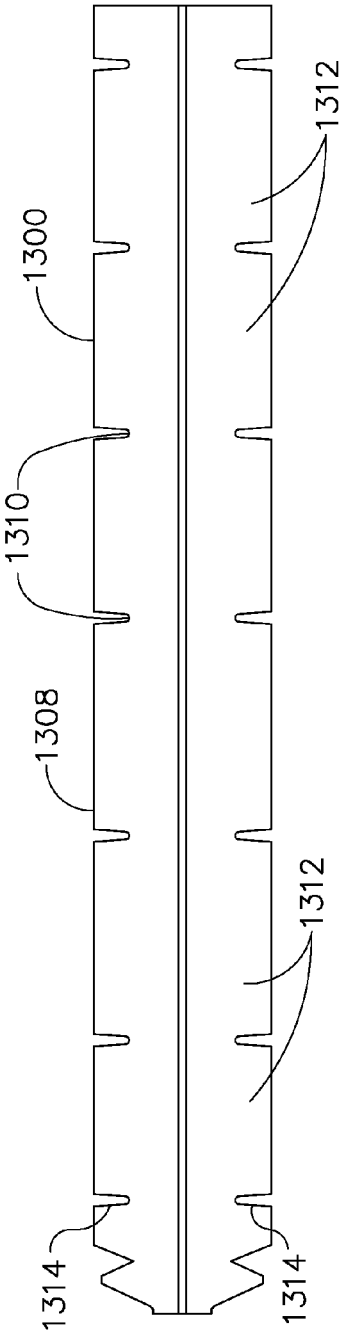
FIG. 55 is a top view of a tissue thickness compensator including a plurality of slits according to various embodiments.

Further to the above, referring now to FIG. 55, yet another approach can be taken to guide the absorption process of a tissue thickness compensator to yield small pieces with atraumatic outer edges. For example, as illustrated in FIG. 55, a tissue thickness compensator such as tissue thickness compensator 1300 may comprise a plurality of slits 1310 which can be strategically positioned to improve the flexibility of tissue thickness compensator 1300, as described above. In addition, slits 1310 may partially divide tissue thickness compensator 1300 into a plurality of portions 1312 which may separate from each other during an initial stage of the absorption process. Slits 1312 can reduce the width of tissue thickness compensator 1300 along outer peripheries 1314 of portions 1312, as illustrated in FIG. 55. This reduction in width may lead to faster absorption along the outer peripheries 1314 of portions 1312, which can result in reducing tissue thickness compensator 1300 into separate portions 1312 during the initial stage of the absorption process.

Figure 55A:
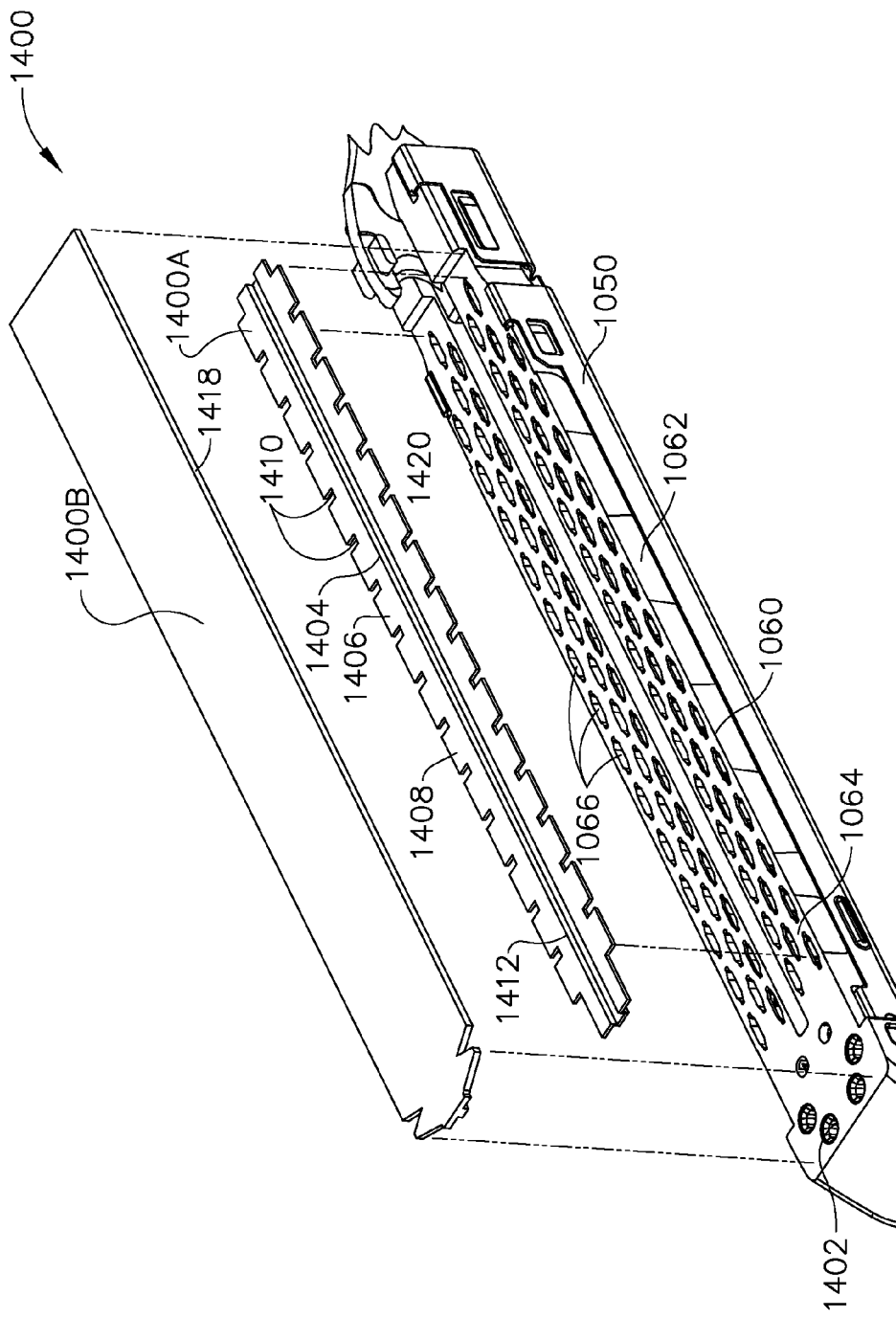
FIG. 55A is an exploded perspective view of an end effector of a stapling instrument comprising a staple cartridge and a tissue thickness compensator according to various embodiments.

Referring generally to FIGS. 55A-57, as described above, the staple cartridge channel 1050 can be configured to receive a staple cartridge 1060, for example, which in at least one embodiment, can be removably retained within the staple cartridge channel 1050. In various embodiments, the staple cartridge 1060 can comprise a cartridge body 1062, a cartridge deck 1064, and a tissue thickness compensator 1400 wherein, in at least one embodiment, as illustrated in FIG. 55A, tissue thickness compensator 1400 may be removably positioned against or adjacent cartridge deck 1064 and may comprise protrusions (not shown), as described above for mating engagement with recesses 1402.

Figure 55B:
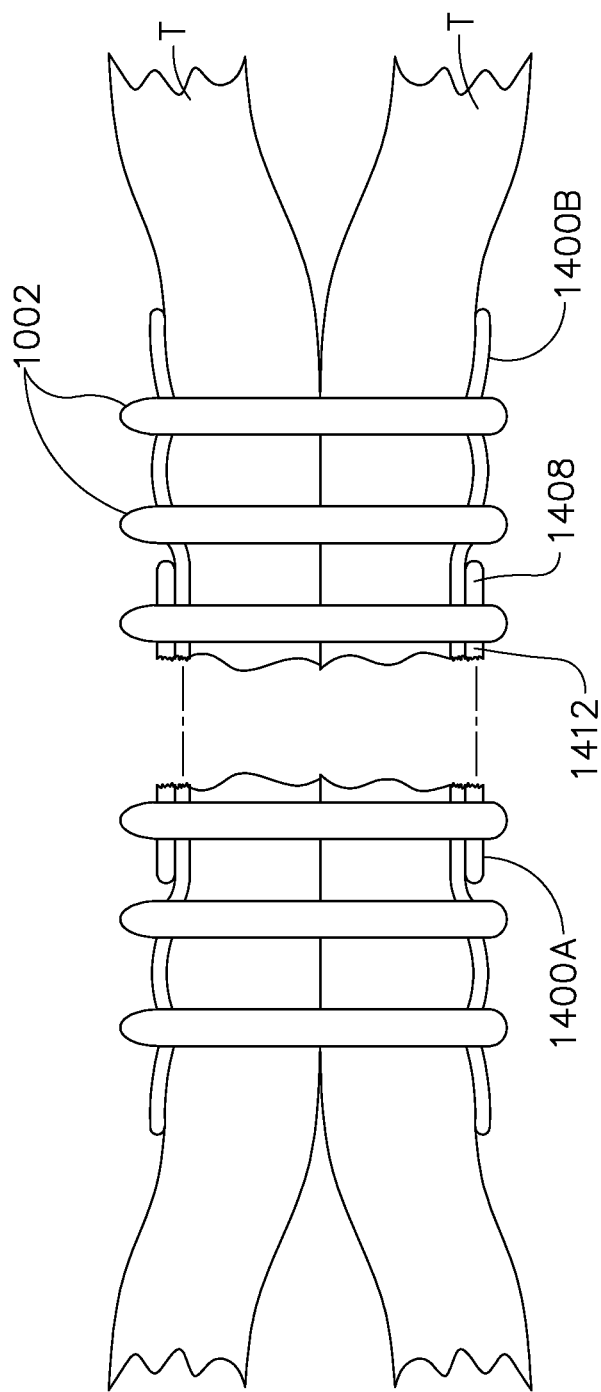
FIG. 55B is a cross sectional view of tissue thickness compensators fastened to tissue according to various embodiments.

Referring again to FIGS. 55A-57, compensator 1400 may comprise a plurality of layers. For instance, compensator 1400 may comprise a first layer 1400A, and a second layer 1400B, which can be positioned over the first layer 1400A. In addition, an outer periphery 1418 of the second layer 1400B may be at least partially extended beyond an outer periphery 1420 of the first layer 1400A. Furthermore, the first layer 1400A and the second layer 1400B may comprise different degrees of stiffness. For example, the second layer 1400B may be configured to be more flexible than the first layer 1400A. As illustrated in FIG. 55B, this arrangement may provide tissue thickness compensator 1400 with a sufficiently rigid inner region, comprised from the first layer 1400A and the second layer 1400 B, which may be suitable to provide adequate support for staples 1002, and a sufficiently flexible outer region, comprised from the second layer 1400B, which may be suitable to provide sufficient flexibility to soften the impact upon tissue T, for example, during and/or after the capturing of the tissue T and the tissue thickness compensator 1400 by staples 1002. Layers 1400A and 1400B can be joined together, for example, by an adhesive. Other attachment means for attaching the first layer 1400A to the second layer 1400B are contemplated within the scope of the current disclosure.

Further to the above, referring again to FIG. 55A, the first layer 1400A may include an inner portion 1404 and an outer portion 1406 at least partially surrounding the inner portion 1404, wherein the outer portion 1406 may be configured to be more flexible than the inner portion 1404. For example, as illustrated in FIG. 55A, the outer portion 1404 may comprise a plurality of slits 1410, which as described above, may increase the flexibility of the outer portion 1404. Furthermore, as described above, the second layer 1400B may be configured to be more flexible than the first layer 1400A. This arrangement may provide tissue thickness compensator 1400 with three regions of different rigidity including a first inner region having the most rigidity, the inner region being comprised of inner portion 1404 of first layer 1400A and second layer 1400B, a middle region having an intermediate rigidity, the middle region being comprised of outer portion 1408 of first layer 1400A and the second layer 1400B, and a third outer region having the least rigidity, the third region being comprised solely of the second layer 1400B.

Figure 56:
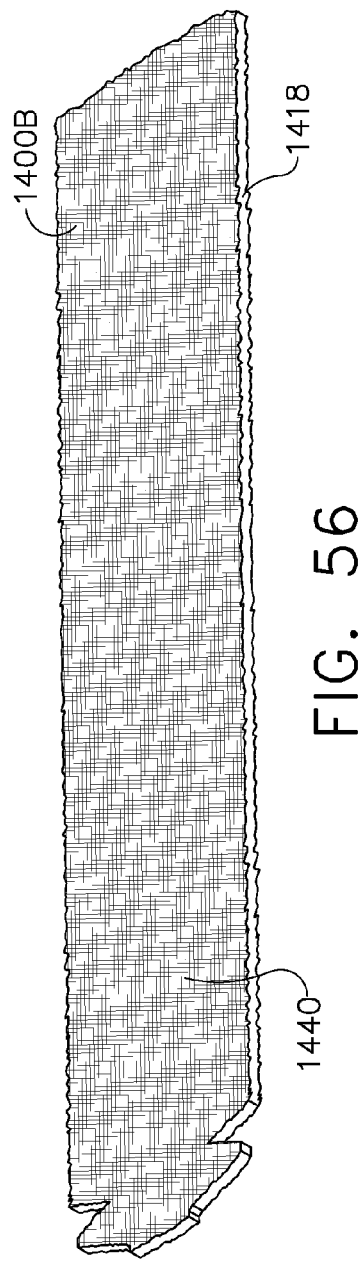
FIG. 56 is a perspective view of a tissue thickness compensator according to various embodiments.
Figure 57:
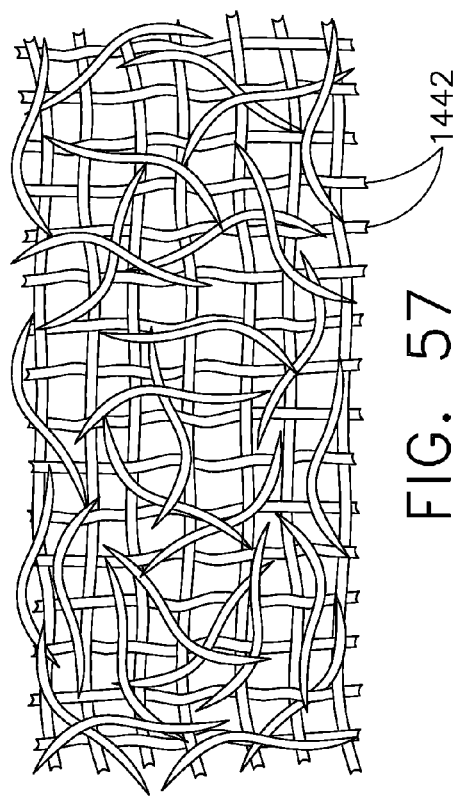
FIG. 57 is a detail view of the tissue thickness compensator in FIG. 56.

Referring now to FIGS. 56 and 57, the second layer 1400B of tissue thickness compensator 1400 can comprise a woven structure 1440, which may include a plurality of fibers 1442 which may be woven into woven structure 1440. The woven structure 1440 may provide the second layer 1400B with sufficient flexibility to soften the impact upon tissue T, for example, during and/or after the capturing of the tissue T and the tissue thickness compensator 1400 by staples 1002. Furthermore, the outer periphery 1418 can be comprised of fibers 1042 which can provide an atraumatic tissue contacting surface to minimize impact upon tissue T, as described above. Woven structure 1440 and fibers 1042 can be comprised of biocompatible materials. Furthermore, woven structure 1040 and/or fibers 1042 can be comprised from a bioabsorbable material such as PLLA, PGA, PCL, and/or combinations thereof, for example.

Figure 60:
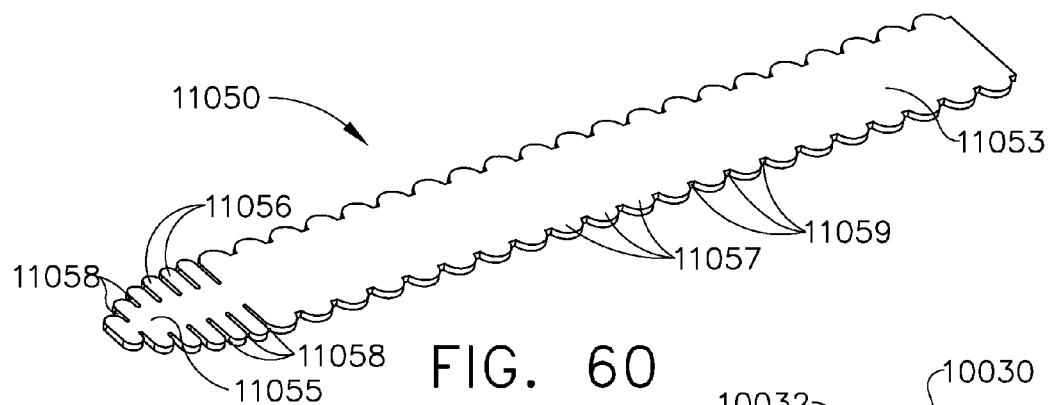
FIG. 60 is a perspective view of a layer configured to be used in connection with a staple cartridge.
Figure 60A:
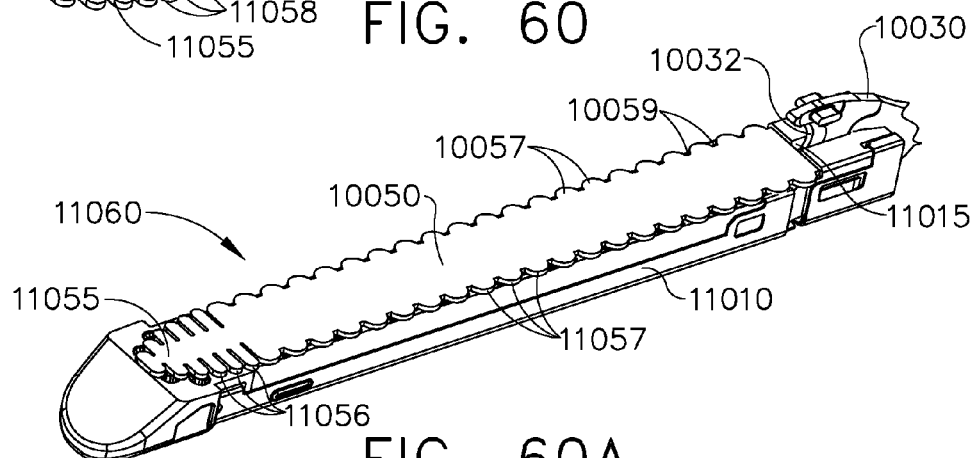
FIG. 60A is a perspective view of the layer of FIG. 60 attached to a staple cartridge.
Figure 60B:
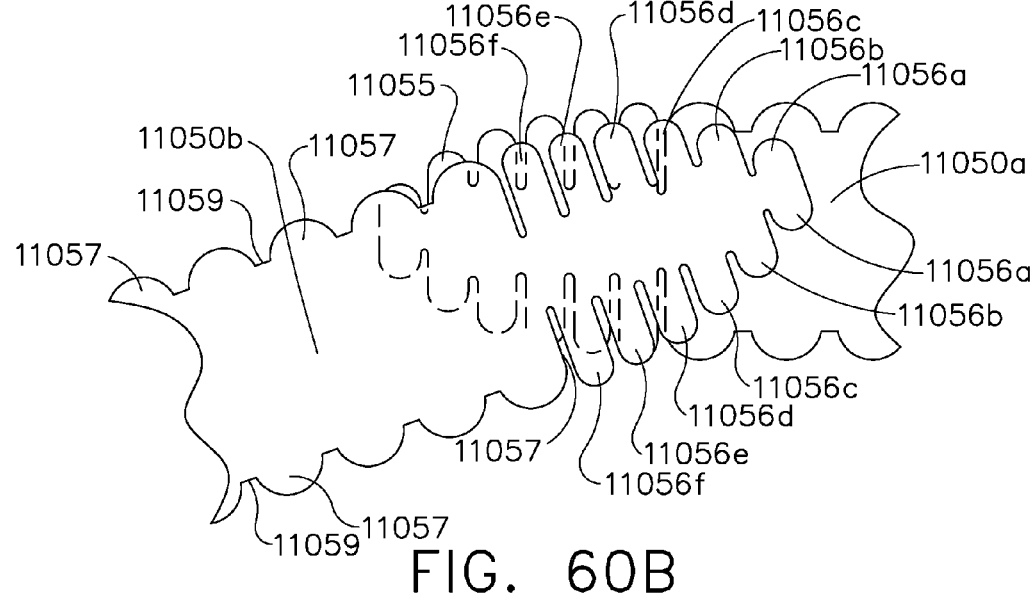
FIG. 60B is a detail view of adjacent layers at least partially overlapping with each other.

Referring now to FIGS. 60-60B, as described in greater detail below, a tissue thickness compensator 11050 can comprise a proximal end 11053 and a distal end 11055 wherein the proximal end 11053 and/or the distal end 11055 can comprise one or more strain relief portions which can reduce the rigidity of the tissue thickness compensator 11050 and the rigidity of the tissue being stapled. The distal end 11055 of the tissue thickness compensator 11050 can comprise one or more slots 11058 defined therein. The slots 11058 can comprise cuts and/or notches, for example, defined in the tissue thickness compensator 11050. The slots 11058 can define projections, or tabs, 11056 which can be configured to at least partially move and/or flex relative to one another and/or the body portion of the tissue thickness compensator 11050. Stated another way, the slots 11058 can provide localized strain relief to the tissue thickness compensator 11050 and the underlying tissue. In certain circumstances, the tabs 11056 of a first tissue thickness compensator 11050 can be overlapped with a proximal end 11053 of a second tissue thickness compensator 11050. In various circumstances, the slots 11058 can permit the first tissue thickness compensator 11050 and the second tissue thickness compensator to pivot relative to one another. In certain circumstances, referring primarily to FIG. 60B, the tabs 11056 of a first tissue thickness compensator 11050 can be overlapped with the tabs 11056 of a second tissue thickness compensator 11050. In various circumstances, the slots 11058 in the overlapped distal ends 11055 can further reduce the rigidity within the underlying tissue. Although the illustrated embodiment of tissue thickness compensator 11050 only comprises an arrangement of tabs 11057 and slots 11058 on one end thereof, a tissue thickness compensator may comprise an arrangement of tabs 11056 and slots 11058 on both ends thereof, for example.

In certain embodiments, further to the above, each tab 11056 can comprise a tapered profile. For instance, each tab 11056 can comprise a base attached to the body of the tissue thickness compensator 11050 having a base width and a free end on the opposite end thereof having an end width, wherein the base width can be wider than the end width. In certain embodiments, the end width can be wider than the base width. Referring primarily to FIG. 60B, an end 11055 can comprise a plurality of tabs 11056 having different configurations. For instance, the tabs 11056 can have different lengths. As illustrated in FIG. 60B, an end-most tab 11056a can have a first length, a second tab 11056b can have a second length which is longer than the first length, a third tab 11056c can have a third length which is longer than the second length, a fourth tab 11056d can have a fourth length which is longer than the third length, a fifth tab 11056e can have a fifth length which is longer than the fourth length, and a sixth tab 11056f can have a sixth length which is longer than the fifth length, for example. In such an embodiment, the tabs 11056 can become progressively shorter toward the distal end of the tissue thickness compensator 11050. In other embodiments, the lengths of the tabs 11056 can be arranged in any other suitable arrangement.

In various circumstances, further to the above, a layer can comprise edges which define the perimeter of the layer. These edges may be straight, substantially straight, linear, and/or substantially linear, in certain circumstances. In some such circumstances, the layer edges may impinge on and/or otherwise affect the surrounding tissue. Also, in some such circumstances, the edges may be rigid and may rigidly support the tissue. In effect, certain portions of the tissue may be unsupported by the layer which are adjacent to other portions of the tissue which are rigidly supported by the layer without transition therebetween. Referring to FIGS. 60-60B once again, the perimeter of the tissue thickness compensator 11050 can include a contoured configuration which can provide a region of transitional rigidity to the underlying tissue. The perimeter of the tissue thickness compensator 11050 can comprise a plurality of notches or recesses 11059 defined therein which can define tabs 11057. Similar to the above, the tabs 11057 can extend from the body of the tissue thickness compensator 11050 and can move relative thereto. Also similar to the above, each tab 11057 can comprise a base end attached to the body of the tissue thickness compensator 11050 and free end which is movable relative to the base end. In certain circumstances, the free end of a tab 11057 can have a width which is narrower than the width of the base end of the tab 11057 while, in other circumstances, the free end of a tab 11057 can have a width which is wider than the width of the base end of the tab 11057. The tabs 11057 can comprise any suitable configuration such as a semi-circular, or an at least partially arcuate, configuration, for example. As a result of the above, the tissue underlying and/or fastened to the body portion of the tissue thickness compensator 11050 can be rigidly supported by the body portion, the tissue underlying and/or fastened to the tabs 11057 can be less than rigidly supported by the tabs 11057, and the tissue adjacent to the tabs 11057, but not underlying the tabs 11057, may be unsupported by the tissue thickness compensator 11050.

Referring now to FIGS. 58 and 59, a staple cartridge assembly 11100 can comprise a cartridge body 11110 and a tissue thickness compensator 11150 attached to the cartridge body 11110. The cartridge assembly 11100 can further comprise one or more attachment members 11160 configured to releasably hold the tissue thickness compensator 11150 to the cartridge body 11110. In at least one circumstance, each attachment member can comprise a strap which extends around the cartridge body 11110 and the tissue thickness compensator 11150. In use, further to the above, a firing member 10030 can be advanced through the staple cartridge 11100 to incise the tissue thickness compensator 11150, fire the staples at least partially stored in the cartridge body 11110, and sever the attachment members 11160. The tissue thickness compensator 11150 can comprise a first, or proximal, end 11157 and a second, or distal, end 11155. The distal end 11155 can comprise an elongate projection 11156 extending from a body portion 11153 of the tissue thickness compensator 11150. As illustrated in FIG. 58, the elongate projection 11156 can extend distally with respect to the distal-most attachment member 11160. In at least the illustrated embodiment, the cartridge body 11110 can comprise a deck 11113 within which staple cavities of the cartridge body 11110 can be defined. In various circumstances, the body 11153 of the tissue thickness compensator 11150 can be configured and arranged such that it covers the deck 11113 and the staple cavities defined in the cartridge body 11110. In at least some circumstances, as also illustrated in FIG. 58, the elongate projection 11156 can extend distally from the deck 11113 and extend distally with respect to the staple cavities defined in the deck 11113.

In use, further to the above, the tissue thickness compensator 11150 can be fastened to tissue and can provide tissue thickness compensation properties, as described herein. Similar to the above, the tissue underlying the tissue thickness compensator 11150 may be rigidly supported by the tissue thickness compensator 11150 and the staples securing the same whereas the tissue surrounding the tissue thickness compensator 11150 may be unsupported by the tissue thickness compensator 11150 and may be flexible. In such circumstances, the tissue between the flexible unsupported tissue and the rigidly supported tissue underlying the tissue thickness compensator 11150, i.e., the transition tissue, can undergo an undesirable amount of strain. Such strain may negatively impact the transition tissue. For instance, when a tissue thickness compensator is secured to pulmonary, or lung, tissue, for example, the tissue immediately surrounding the perimeter of the tissue thickness compensator, i.e., the perimeter tissue, may tear in certain circumstances, especially the perimeter tissue adjacent to and/or surrounding the distal end of the tissue thickness compensator, i.e., the end perimeter tissue. The distal projection 11156 of the tissue thickness compensator 11150, however, can support the end perimeter tissue. Stated another way, the distal projection 11156 can provide transitional support to the end perimeter tissue. Such transitional support can be less than the support provided by the body of the tissue thickness compensator 11150 and can mitigate the change in strain between the unsupported tissue and the fully supported tissue underlying the tissue thickness compensator 11150. In various circumstances, the distal projection 11156 can provide an enlarged area in which force can be transmitted between the unstapled tissue and the stapled tissue. The distal projection 11156 can be configured to flex and move with the unsupported tissue and the tissue thickness compensator 11150. In various circumstances, the distal projection 11156 can move relative to the body portion of the tissue thickness compensator 11150 and/or the unsupported tissue.

The tissue thickness compensator 11150, referring again to FIGS. 58 and 59, can further comprise a notch 11157 defined in the proximal end 11153 thereof. The notch 11157 can be defined between two distally extending projections 11158. The notch 11157 can comprise any suitable shape, such as a parabolic shape, for example. Similar to the above, the distally extending projections 11158 can provide transitional support to the proximal end perimeter tissue. Such transitional support can be less than the support provided by the body of the tissue thickness compensator 11150 and can mitigate the change in strain between the unsupported tissue and the fully supported tissue underlying the tissue thickness compensator 11150. In various circumstances, the proximal projections 11158 can provide an enlarged area in which force can be transmitted between the unstapled tissue and the stapled tissue. The proximal projections 11158 can be configured to flex and move with the unsupported tissue and the tissue thickness compensator 11150. In various circumstances, the proximal projections 11158 can move relative to the body portion of the tissue thickness compensator 11150, each other, and/or the unsupported tissue. Various alternative embodiments are envisioned in which more than two projections extend from the proximal end and/or distal end of a tissue thickness compensator.

As illustrated in FIG. 59, two or more tissue thickness compensators 11150 can be implanted in an end-to-end manner along a path. In such circumstances, the distal end 11155 of a first tissue thickness compensator 11150 can overlap with the proximal end 11153 of a second tissue thickness compensator 11150. Similarly the distal end 11155 of the second tissue thickness compensator 11150 can overlap with the proximal end 11153 of a third tissue thickness compensator 11150. In various circumstances, the distal projection 11156 of the first tissue thickness compensator 11150 can be aligned, or at least substantially aligned, with the recess 11157 of the second tissue thickness compensator 11150. Also, in various embodiments, the distal projection 11156 and the proximal recess 11558 can be sized and configured such that they have substantially the same size and/or shape. In various circumstances, a distal projection 11156 can be configured to be positioned within a proximal recess 11157 of an adjacent tissue thickness compensator 11150.

Figure 61:
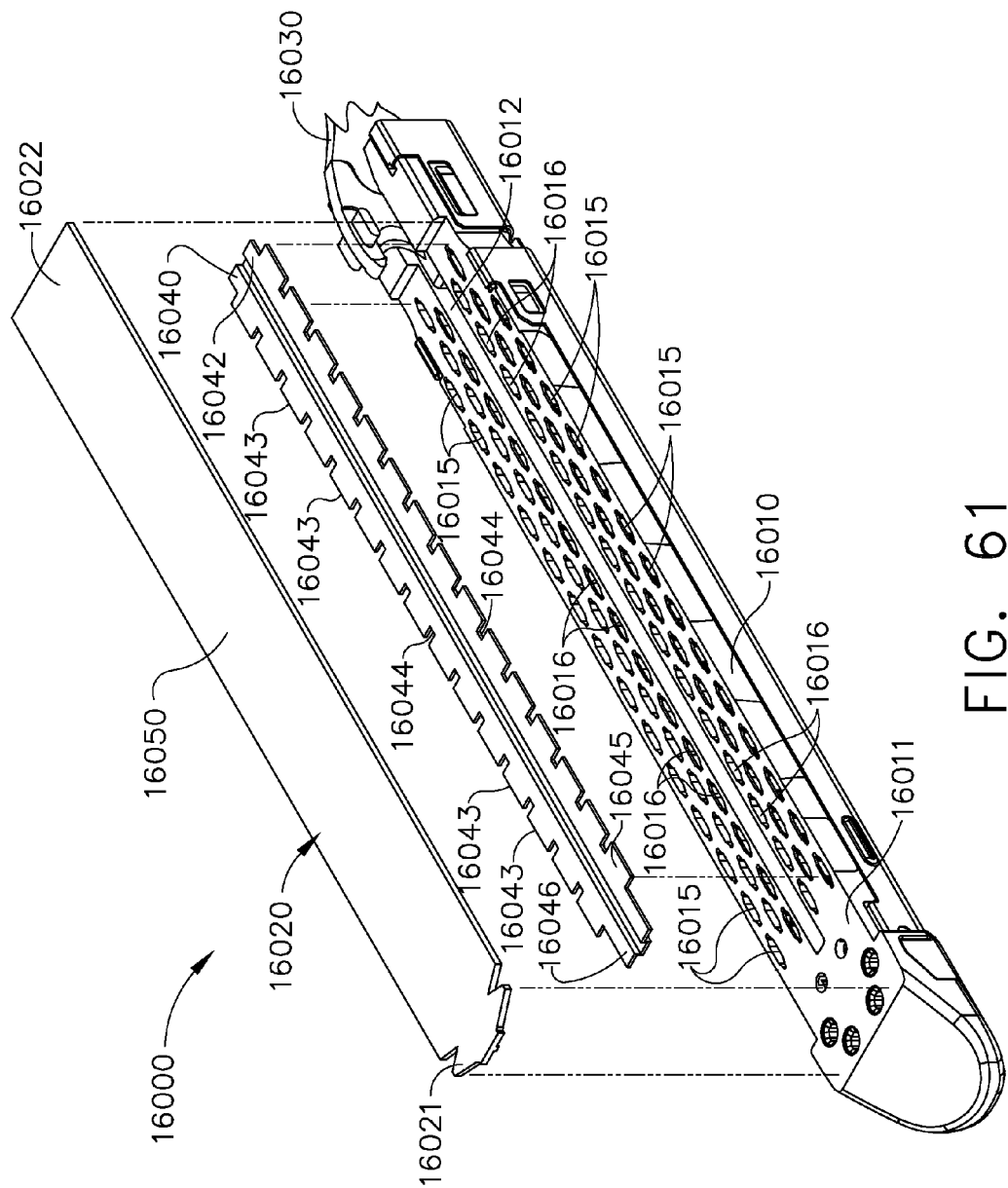
FIG. 61 is an exploded view of a staple cartridge assembly including a cartridge body and a layer assembly which includes a first layer and a second layer.

In various embodiments, referring now to FIG. 61, a staple cartridge assembly 16000 can comprise a cartridge body 16010 and a layer assembly 16020. The cartridge body 16010 can comprise a deck 16011 and a longitudinal slot 16012 defined in the deck 16011 which can be configured to slidably receive a cutting member 16030 therein. The cartridge body 16010 can further comprise a plurality of staple cavities defined therein which can each be configured to removably store a staple therein. The staple cavities can be part of two or more groups. For instance, the staple cavities can be divided into a first group of staple cavities 16015 and a second group of staple cavities 16016. In various circumstances, the groups of staple cavities can be organized in rows while, in other circumstances, the groups of staple cavities can overlap, or be inter-dispersed, with each other. In either event, the layer assembly 16020 can comprise a plurality of layers which can extend over the staple cavities. In use, as described in greater detail further below, the staples, when ejected from the staple cavities, can capture at least a portion of the layer assembly 16020 therein. The layers of the layer assembly 16020 can be configured such that only certain layers of the layer assembly 16020 extend over certain staple cavities. For instance, the layer assembly 16020 can comprise a first layer 16050 which can extend over the first group of staple cavities 16015 and the second group of staple cavities 16016 and, in addition, a second layer 16040 which can extend over the second group of staple cavities 16016 but may not extend over the first group of staple cavities 16015.

Figure 62:
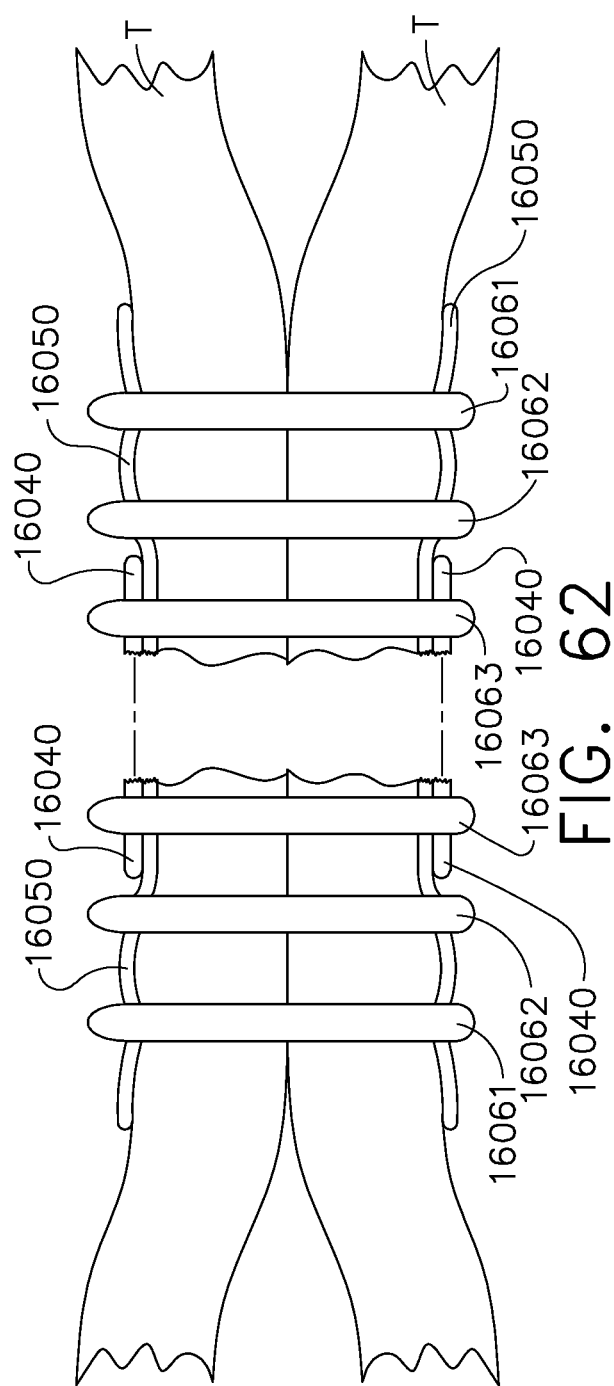
FIG. 62 is a side view of tissue T captured between layer assemblies by fired staples from the staple cartridge assembly of FIG. 61.
Figure 63:
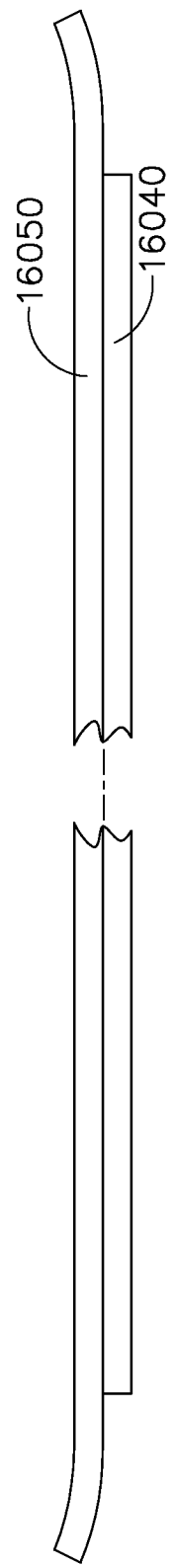
FIG. 63 is a cross-sectional view of the layer assembly of FIG. 61 showing the first layer and the second layer.

In use, as a result the above and referring primarily to FIG. 62, certain staples deployed from the staple cartridge 16000 may capture only the first layer 16050 of the layer assembly 16020 while other staples may capture only the second layer 16040 of the layer assembly 16020. For instance, one or more outer rows of staples 16061 may capture only the first layer 16050 while one or more inner rows of staples 16063 may capture both the first layer 16050 and the second layer 16040. In various embodiments, one or more intermediate rows of staples 16062 can include some staples which capture only the first layer 16050 and other staples which capture both the first layer 16050 and the second layer 16040. In at least one embodiment, the second layer 16040 can comprise a plurality of tabs 16043 which can be configured to be captured within the staples 16062 of the intermediate row. The tabs 16043 can be separated by slots 16044 which can permit the tabs 16043 to move and flex relative to one another. For instance, the arrangement of slots 16044 and tabs 16043 can introduce flexibility within the staple tissue. In certain embodiments, the tabs 16043 can be sufficiently spaced apart such that some of the intermediate staples 16062 may capture a tab 16043 therein while others may not. Referring primarily to FIG. 61 once again, the second layer 16040 can include a longitudinal projection 16042 extending therefrom which can be configured to extend into the longitudinal slot 16012 defined in the cartridge body 16010. In various circumstances, the longitudinal projection 16042 can be releasably secured or within the longitudinal slot 16012. In at least one embodiment, the longitudinal projection 16042 can fit snugly within the longitudinal slot 16012 via a press-fit engagement, for example. In any event, the engagement between the longitudinal slot 16012 and the longitudinal projection 16042 can maintain the alignment between the second layer 16040 and the cartridge body 16010. Moreover, the first layer 16050 can be mounted to the second layer 16040 such that the projection 16042 can also hold the first layer 16050 in position.

Further to the above, the first layer 16050 of the layer assembly 16020 can cover a first group of staple cavities and the second layer 16040 can cover a second group of staple cavities. Stated another way, the first layer 16050 of the layer assembly 16020 can have a different footprint than the second layer 16040. In various embodiments, the first layer 16050 of the layer assembly 16020 and the second layer 16040 can be comprised of different materials. In at least one such embodiment, the second layer 16040 can comprise a rigid material and can be configured to support the first layer 16050. The first layer 16050 can be comprised of a flexible material, or at least a material which is more flexible than the material comprising the second layer 16050. Referring primarily to FIG. 62, the flexible first layer 16050 can extend laterally beyond the second layer 16040. In such circumstances, the first layer 16050 can provide for a more flexible lateral edge of the layer assembly 16020. After the layer assembly 16020 has been implanted against the tissue T by the staples and transected by the cutting member 16030, referring primarily to FIG. 62, the second layer 16050 can support the tissue T located adjacent to the transection line while the first layer 16040 can extend laterally away alongside the tissue T. In various circumstances, the first layer 16040 can provide a flexible transition between the tissue T supported by the second layer 16050 and the tissue T unsupported by the layer assembly 16020. In various circumstances, the first layer 16050 can comprise a tissue thickness compensator and the second layer 16040 can be comprised of a laminate material, for example.

In various embodiments, referring primarily to FIG. 61, the layer assembly 16020 can be attached to the cartridge body 16010. In at least one embodiment, the cartridge assembly 16000 can comprise at least one tie, or connector, which can releasably hold the layer assembly 16020 to the cartridge body 16010. For instance, the cartridge assembly 16000 can comprise a first connector releasably holding a distal end 16021 of the layer assembly 16020 to a distal end of the cartridge body 16010 and a second connector holding a proximal end 16022 of the layer assembly 16020 to a proximal end of the cartridge body 16010. As the firing member 16030 is advanced from the proximal end to the distal end of the cartridge body 16010 to deploy the staples therefrom and incise the layer assembly 16020, the firing member 16030 can also transect and/or otherwise defeat the connectors holding the layer assembly 16020 to the cartridge body 16010.

Referring now to FIGS. 64-66, an end effector assembly 5400 can include a first jaw, illustrated elsewhere, and a second jaw 5402. In various embodiments, the second jaw 5402 can include a fastener cartridge body 5450 and a layer of material 5458 releasably secured to the fastener cartridge body 5450 and/or to the second jaw 5402. The fastener cartridge body 5450 and the layer of material 5458 releasably secured thereto can comprise a fastener cartridge assembly, for example. In various embodiments, the layer of material 5458 can comprise a piece of buttress material and/or a tissue thickness compensator, for example. In certain embodiments, the layer of material 5458 can be a piece of buttress material releasably secured to the fastener cartridge body 5450, for example. The second jaw 5402 can have a proximal portion 5404 and a distal portion 5406. In various embodiments, the second jaw 5402 can have a proximal connector 5480*a* (FIGS. 65 and 66) at the proximal portion 5404 and a distal connector 5480*b* (FIG. 66) at the distal portion 5406. The proximal connector 5480*a* and the distal connector 5480*b* can secure the layer of material 5458 relative to the cartridge body 5450. The connectors 5480*a*, 5480*b* can comprise bands and/or cords, for example.

Referring primarily to FIG. 64, the cartridge body 5450 can include a deck 5452. A slot 5456 can extend from the proximal portion 5404 toward the distal portion 5406 of the second jaw 5402, for example, and can be defined in a portion of the deck 5452, for example. In various embodiments, fastener cavities 5454 can also be defined in the deck 5452. Further, the second jaw 5402 can include fasteners, such as surgical staplers, for example, removably positioned in the fastener cavities 5454. For example, a fastener can be ejectably positioned in each fastener cavity 5454 of the cartridge body 5450. In various embodiments, the fasteners can be ejected from their respective fastener cavities 5454 by a sled 5434 (FIGS. 65 and 66) during a firing stroke.

Referring primarily to FIGS. 65 and 66, a firing assembly 5430 can include a firing bar 5432, a cutting edge 5436, and a foot 5438. The cutting edge 5438 can cut tissue and/or the layer of material 5458, for example, and the foot 5438 can guide the firing assembly 5430 along the slot 5456 in the cartridge body 5450 (FIG. 64), for example. In various embodiments, the firing assembly 5430 can move along the slot 5456 in the cartridge body 5450 during a firing stroke. The firing assembly 5430 can engage the sled 5434 in the cartridge body 5430 and can drive the sled 5434 at least partially through the cartridge body 5450, for example. In certain embodiments, the sled 5434 can have a camming surface or ramp 5442, which can engage drivers in the fasteners cavities 5454 during the firing stroke. When the ramp 5442 engages a driver in a fastener cavity 5454, the ramp 5442 can cam the driver and the corresponding fastener toward the cartridge deck 5452, and can eject the fastener from the fastener cavity 5454, for example. In certain embodiments, referring primarily to FIG. 65, at the beginning of the firing stroke, the firing assembly 5430 can be positioned at a proximal portion 5404 of the second jaw 5402. In such embodiments, referring primarily to FIG. 66, the firing bar 5432 can drive the firing assembly 5430 distally during the firing stroke. In various embodiments, the cutting edge 5436 can cut the proximal connector 5480*a* and the distal connector 5480*b* during the firing stroke. The cutting edge 5436 can cut the proximal connector 5480*a* at or near the beginning of the firing stroke, for example, and can cut the distal connector 5480*b* at or near the end of the firing stroke, for example.

Referring still to FIGS. 64-66, the layer of material 5458 can be secured to the deck 5452 of the cartridge body 5450 (FIG. 64) by the proximal connector 5480*a* (FIG. 65) and by the distal connector 5480*b* (FIGS. 65 and 66). Furthermore, the layer of material 5458 can include at least one mount 5460. The mount 5460 can be integrally molded with the layer of material 5458, for example. In certain embodiments, when the layer of material 5458 is secured to the deck 5452, the mount 5460 can extend from the layer of material 5458 into the slot 5456 of the cartridge body 5450. Referring primarily to FIG. 65, the mount 5460 can extend into the slot 5456 (FIG. 64) between the proximal connector 5480*a* and the distal connector 5480*b*, for example. In other words, the mount 5460 can extend from an intermediate portion 5468 of the layer of material 5458. In various embodiments, the mount 5460 can be sized to fit in the slot 5456 when the layer of material 5458 is positioned on the deck 5452 cartridge body 5450. Furthermore, the mount 5460 can be sized for unforced removal from the slot 5456 when the layer of material 5458 is lifted and/or peeled away from the cartridge body 5458. For example, the mount 5460 may not be friction fit in the slot 5456 and, in certain embodiments, when the mount 5460 is positioned in the slot 5456, a clearance or gap can exist between the mount 5460 and the slot 5456. The clearance can be approximately 0.12 mm, for example. In certain embodiments, the clearance can be up to approximately 0.24 mm, for example. In some embodiments, an interference of approximately 0.01 mm to approximately 0.12 mm can exist between the mount 5460 and the slot 5456, for example, such that the mount 5460 is compressed when positioned in the slot 5456, for example.

Referring still to FIGS. 64-66, the mount-slot engagement can prevent and/or limit lateral shifting and/or buckling of the intermediate portion 5468 of the layer of material 5458. For example, when the end effector assembly 5400 is placed and/or moved relative to tissue at a surgical site, the mount 5460 can remain positioned within the slot 5456 (FIG. 64) to hold the intermediate portion 5468 in position relative to the cartridge deck 5452. Some shifting of the layer of material 5458 may be possible owing to the clearance defined between the mount 5460 and the slot 5456, for example. In various embodiments, the mount 5460 may not resist lifting and/or peeling of the layer of material 5458 away from the cartridge body 5450. For example, the mount 5460 may not be friction fit in the slot 5456, and the mount 5460 can be easily removed from the slot 5456 when the layer of material 5458 is lifted away from the deck 5452 of the cartridge body 5450, for example, after the cutting edge 5436 cuts the proximal connector 5680a and the distal connector 5680b. For example, as the firing assembly 5430 is driven distally during the firing stroke, an element of the firing assembly 5430 can contact the mount 5460 within the slot 5456. Referring primarily to FIG. 66, the sled 5434 can contact the mount 5460 when the sled 5434 is driven distally by the firing assembly 5430. Further, the sled 5434 can flex the mount 5460 out of the sled's path and out of the slot 5456. In other words, the sled 5434 can flex the mount 5460 to remove the mount 5460 from the slot 5456.

In various embodiments, the layer of material 5458 can include multiple mounts 5460, which can extend from the layer of material 5458 into the slot 5456 (FIG. 64) in the cartridge body 5450. The mounts 5460 can be spaced along at least a portion of the length of the slot 5456, for example. In certain embodiments, at least one mount 5460 can be positioned in the proximal portion 5404 of the second jaw 5402, and at least one mount 5460 can be positioned in the distal portion 5406 of the second jaw 5402. Further, the mounts 5460 can be positioned intermediate the proximal and distal connectors 5480a, 5480b (FIG. 65), for example. As the firing assembly 5430 (FIGS. 65 and 66) is fired distally during the firing stroke, the sled 5434 can sequentially engage each mount 5460 in the slot 5456 to flex and remove each mount 5460 from the slot 5456. When each mount 5460 is released from the slot 5456 and the proximal and distal connectors 5480a, 5480b are cut or otherwise overcome, the layer of material 5458 can be unsecured relative to the deck 5452 of the cartridge body 5450.

Referring still to FIGS. 64-66, a mount 5460 can include a flexible stem 5462 and a head 5464. The flexible stem 5462 of the mount 5460 can flex when an element of the firing assembly 5430, such as the sled 5434, pushes against the head 5464 during the firing stroke. In certain embodiments, the head 5464 can have an enlarged, rounded shape to minimize the clearance between the head 5464 and the slot 5456 of the cartridge body 5450. In various embodiments, the head 5464 can fit within the slot 5456, and can be easily and smoothly removed from the slot 5456 when the layer of material 5458 lifted and/or peeled away from the cartridge body 5450.

Referring now to FIGS. 67-70, an end effector assembly 5500 can include a first jaw, illustrated elsewhere, and a second jaw 5502. In various embodiments, the second jaw 5502 can include the cartridge body 5450 and a layer of material 5558 releasably secured to the cartridge body 5450 and/or to the second jaw. The cartridge body 5450 and the layer of material 5558 releasably secured thereto can comprise a fastener cartridge assembly, for example. In various embodiments, the layer of material 5558 can comprise a piece of buttress material and/or a tissue thickness compensator, for example. In certain embodiments, the layer of material 5558 can be a piece of buttress material releasably secured to the cartridge body 5450. Further, the second jaw 5502 can have a proximal portion 5504 and a distal portion 5506. In various embodiments, the second jaw 5502 can have a proximal connector 5580a (FIGS. 68 and 69) at the proximal portion 5504 and a distal connector 5580b (FIG. 68) at the distal portion 5506. The proximal connector 5580a and the distal connector 5580b can secure the layer of material 5558 relative to the cartridge body 5450. In various embodiments, the layer of material 5558 can include a ridge 5560. The ridge 5560 can be integrally molded with the layer of material 5558, for example. Referring primarily to FIG. 67, the ridge 5560 can extend longitudinally along at least a portion of the length of the layer of material 5558.

Figure 69:
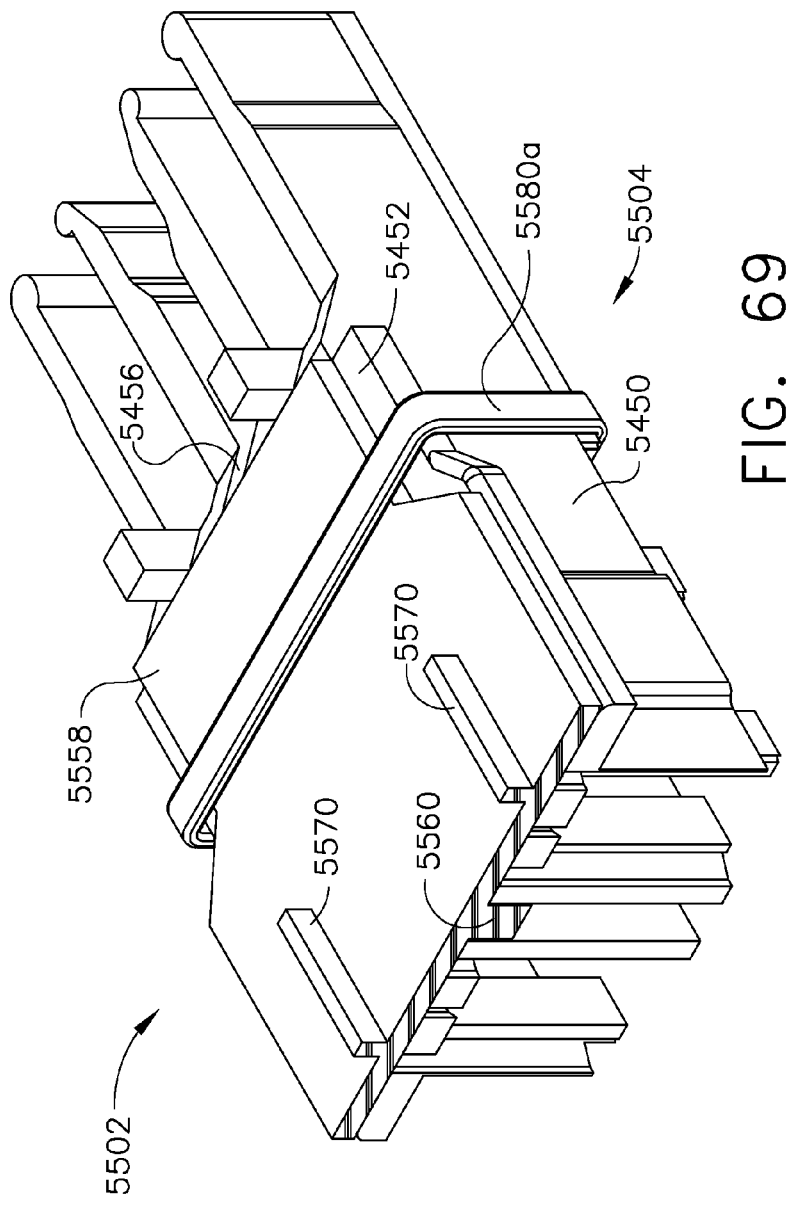
FIG. 69 is a cross-sectional, perspective view of the fastener cartridge assembly of FIG. 67 taken along the plane indicated in FIG. 68, depicting the layer of material secured to the cartridge body by the proximal connector.

Referring primarily to FIG. 69, when the layer of material 5558 is secured to the cartridge body 5460, the ridge 5560 can extend into the slot 5456 in the cartridge body 5450. The ridge 5560 can extend into the slot 5456 between the proximal connector 5580a and the distal connector 5580b, for example. In various embodiments, the ridge 5560 can be sized to fit in the slot 5456 when the layer of material 5558 is positioned on the cartridge body 5450. Furthermore, the ridge 5560 can be sized for unforced removal from the slot 5456 when the layer of material 5558 is lifted and/or peeled away from the cartridge body 5458. For example, the ridge 5560 may not be friction fit in the slot 5456 and, in certain embodiments, when the ridge 5560 is positioned with the slot 5456, a clearance or gap can exist between the ridge 5560 and the slot 5456. The clearance can be approximately 0.08 mm, for example. In certain embodiments, the clearance can be up to approximately 0.24 mm, for example. In some embodiments, an interference of approximately 0.01 mm to approximately 0.06 mm can exist between the ridge 5560 and the slot 5456, for example, such that the ridge 5560 is compressed when positioned in the slot 5456, for example.

In various embodiments, the ridge-slot engagement can prevent and/or limit lateral shifting and/or buckling of the layer of material 5558 relative to the deck 5452 of the cartridge body 5450. For example, when the end effector assembly 5500 is placed and/or moved relative to tissue at a surgical site, the ridge 5560 can remained positioned in the slot 5456 to hold the layer of material 5558 in position relative to the cartridge deck 5452. Some shifting of the layer of material 5558 relative to the cartridge body 5450 may be possible owing to the clearance defined between the ridge 5560 and the slot 5456, for example. In various embodiments, the ridge 5560 may not resist lifting and/or peeling of the layer of material 5558 away from the cartridge body 5450. For example, the ridge 5560 may not be friction fit in the slot 5456, and the ridge 5560 can be easily and smoothly removed from the slot 5456 when the layer of material 5550 is lifted away from the deck 5452 of the cartridge body 5450, for example, after the cutting edge 5436 cuts the proximal connector 5680a and the distal connector 5680b. In various embodiments, the cutting edge 5436 of the firing assembly 5430 can cut the layer of material 5558, as well as the ridge 5560, for example, when the cutting edge 5436 is driven distally during the firing stroke.

Figure 70:
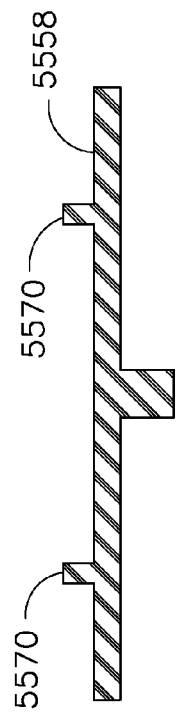
FIG. 70 is a cross-sectional, elevation view of the layer of material of FIG. 67 taken along the plane indicated in FIG. 68.

Referring primarily to FIGS. 68-70, the layer of material 5558 can include a reinforcement feature 5570, which can extend along at least a portion of the length of the layer of material 5558. The reinforcement feature 5570 can extend from a proximal portion 5504 of the second jaw 5502 toward the distal portion 5506 of the second jaw 5502, for example. The reinforcement feature 5570 can be integrally molded with the layer of material 5558, for example. In various embodiments, the reinforcement feature 5570 can increase the moment of inertia of the layer of material 5558 such that the reinforcement feature 5570 can reinforce, support and/or rigidify the layer of material 5558. For example, when the cutting edge 5436 (FIGS. 65 and 66) traverses the layer of material 5558 during the firing stroke, the reinforcement feature 5570 can prevent and/or limit shifting and/or buckling of the layer of material 5558 relative to the cartridge body 5450. Further, the reinforcement feature 5570 can engage tissue clamped between the first jaw and the second jaw 5502 of the end effector assembly 5500. In certain embodiments, the reinforcement feature 5570 can prevent and/or limiting shifting of the clamped tissue relative to the cartridge body 5450, for example. In various embodiments, the layer of material 5558 can include multiple reinforcement features 5570, which can extend along at least a portion of the length of the layer of material 5558. The reinforcement features 5570 can be parallel, for example, and can extend on either side or both sides of the ridge 5560, for example. In various embodiments, the reinforcement feature 5570 and/or the ridge 5560 can extend along a portion of the length of the layer of material 5558 and can stop before reaching the distal portion thereof. The absence of the reinforcement feature 5570 and/or the ridge 5560 at the distal portion can lend flexibility to the distal portion of the layer of material 5558.

Figure 71:
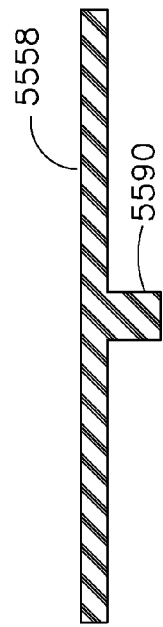
FIG. 71 is a cross-sectional, elevation view of a layer of material for use with an end effector assembly according to various embodiments of the present disclosure.

Referring now to FIG. 71, a layer of material 5588 for use with an end effector assembly can have a longitudinal ridge 5590, similar to the ridge 5560, for example. In various embodiments, the layer of material 5588 and/or the ridge 5590 can be a piece of buttress material and/or a tissue thickness compensator, for example. The ridge 5590 can extend along at least a portion of the length of the layer of material 5588. Further, the ridge 5590 can be received within a slot in the end effector, such as the slot 5456 in the cartridge body 5450 (FIG. 67), for example. In certain embodiments, the ridge 5590 can provide sufficient reinforcement, support, and rigidity to the layer of material 5588, without the addition of supplementary reinforcement features, for example.

Referring now to FIGS. 72-75, an end effector assembly 5600 can include a first jaw, illustrated elsewhere, and a second jaw 5602. In various embodiments, the second jaw 5602 can include the cartridge body 5450 and a layer of material 5658 releasably secured to the cartridge body 5450 and/or to the second jaw 5602. In various embodiments, the cartridge body 5450 and the layer of material 5458 releasably secured thereto can comprise a fastener cartridge assembly, for example. The layer of material 5658 can comprise a piece of buttress material and/or a tissue thickness compensator, for example. In certain embodiments, the layer of material 5658 can be a piece of buttress material releasably secured to the cartridge body 5450, for example. Further, the second jaw 5602 can have a proximal portion 5604 and a distal portion 5606. In various embodiments, the second jaw 5602 can have a proximal connector 5680a (FIGS. 73 and 74) at the proximal portion 5604 and a distal connector 5680b (FIG. 73) at the distal portion 5606. The proximal connector 5680a and the distal connector 5680b can secure the layer of material 5658 relative to the cartridge body 5450. In various embodiments, the layer of material 5658 can include a ridge 5660. The ridge 5660 can be integrally molded with the layer of material 5658, for example. Referring primarily to FIG. 72, the ridge 5660 can extend longitudinally along at least a portion of the length of the layer of material 5658. In various embodiments, the ridge 5660 can be a folded portion of the layer of material 5658. For example, the layer of material 5658 can be crimped, creased and/or folded over itself to form a thicker portion, which can be the ridge 5660. Referring primarily to FIGS. 74 and 75, the ridge 5660 can be folded into a U-shape, for example, and can include a rounded tip 5662.

Referring primarily to FIG. 74, when the layer of material 5658 is secured to the cartridge body 5460, the ridge 5660 can extend into the slot 5456 in the cartridge body 5450. In certain embodiments, the slot 5456 can be structured to receive the ridge 5660. The ridge 5660 can be sized to fit in the slot 5456 when the layer of material 5658 is positioned on the cartridge body 5450. Furthermore, the ridge 5660 can be sized for unforced removal from the slot 5456 when the layer of material 5658 is lifted and/or peeled away from the cartridge body 5458. For example, the ridge 5660 may not be friction fit in the slot 5456 and, in certain embodiments, when the ridge 5660 is positioned within the slot 5456, a clearance or gap can exist between the ridge 5660 and the slot 5456. The clearance can be approximately 0.12 mm, for example. In certain embodiments, the clearance can be up to approximately 0.24 mm, for example. In some embodiments, an interference of approximately 0.01 mm to approximately 0.18 mm can exist between the ridge 5660 and the slot 5456, for example, such that the ridge 5660 is compressed when positioned in the slot 5456, for example.

In various embodiments, the ridge-slot engagement can prevent and/or limit lateral shifting and/or buckling of the layer of material 5658. For example, when the end effector assembly 5600 is placed and/or moved relative to tissue at a surgical site, the ridge 5660 can remained positioned in the slot 5456 to hold the layer of material 5658 in position relative to the cartridge deck 5452. Shifting of the layer of material 5658 relative to the cartridge body 5450 can be limited by the clearance. For example, some sifting of the layer of material 5658 may be possible owing to the clearance defined between the ridge 5660 and the slot 5456. In various embodiments, the ridge 5660 may not resist lifting and/or peeling of the layer of material 5658 away from the cartridge body 5450. For example, the ridge 5660 may not be friction fit in the slot 5456, and the ridge 5660 can be easily removed from the slot when the layer of material 5658 is lifted away from the deck 5452 of the cartridge body 5450, for example, after the cutting edge 5436 cuts the proximal connector 5680a and the distal connector 5680b. In various embodiments, when the firing assembly 5430 (FIGS. 65 and 66) is fired along the slot 5456 during a firing stroke, the sled 5434 and/or another element of the firing assembly 5430 can easily and smoothly release the ridge 5660 from the slot 5456, for example, to release the layer of material 5658 from the cartridge body 5450. The cutting edge 5436 of the firing assembly 5430 can cut the layer of material 5658, as well as the ridge 5660, for example, when the cutting edge 5436 is driven distally during the firing stroke.

Referring primarily to FIGS. 73-75, the layer of material 5658 can include a reinforcement feature 5670, which can extend along at least a portion of the length of the layer of material 5658. The reinforcement feature 5670 can extend from the proximal end of the second jaw 5602 to the distal end of the second jaw 5602, for example. The reinforcement feature 5670 can be integrally molded with the layer of material 5658, for example. In various embodiments, the reinforcement feature 5670 can be a folded portion of the layer of material 5658. For example, the layer of material 5658 can be creased, crimped and/or folded over itself to form a thicker portion, which can form the reinforcement feature 5670. Referring primarily to FIGS. 74 and 75, the reinforcement feature 5670 can be crimped into a V-shape, and can include a pointed tip 5672, for example. In various embodiments, the reinforcement feature 5670 can reinforce, support and/or rigidify the layer of material 5658. In some embodiments, the reinforcement feature 5670 can be configured to bend along the tip 5672 thereof to resist a lateral force applied along the edge of the layer of material 5658 such that the layer of material 5658 remains positioned on the cartridge body 5450. For example, when the cutting edge 5436 (FIGS. 65 and 66) traverses the layer of material 5658 during the firing stroke, the reinforcement feature 5670 can prevent and/or limit shifting and/or buckling of the layer of material 5658 relative to the cartridge body 5450. Further, the reinforcement feature 5670 can engage tissue clamped between the first jaw and the second jaw 5602 of the end effector assembly 5600. For example, the reinforcement feature 5670 can prevent and/or limiting shifting of the clamped tissue relative to the cartridge body 5450. The pointed tip 5672 can engage the tissue, and can hold the tissue in place relative to the layer of material 5658 during the firing stroke, for example. In various embodiments, the layer of material 5658 can include multiple reinforcement features 5670 which can extend along at least a portion of the length of the layer of material 5658. The reinforcement features 5670 can be parallel, for example, and can extend on either side or both sides of the ridge 5660, for example.

Referring now to FIGS. 76 and 77, an end effector assembly 5700 can include a first jaw, illustrated elsewhere, and a second jaw 5702. In various embodiments, the second jaw 5702 can include a cartridge body 5750 and a layer of material 5758 releasably secured to the cartridge body 5750 and/or to the second jaw 5702. In various embodiments, the cartridge body 5750 and the layer of material 5758 releasably secured thereto can comprise a fastener cartridge assembly, for example. The layer of material 5758 can comprise a piece of buttress material and/or a tissue thickness compensator, for example. In certain embodiments, the layer of material 5758 can be a piece of buttress material releasably secured to the cartridge body 5750, for example. The second jaw 5702 can have a proximal portion 5704 and a distal portion 5706. In various embodiments, the second jaw 5702 can have a proximal connector 5780a (FIG. 77) at the proximal portion 5704 and a distal connector 5780b (FIG. 77) at the distal portion 5706. The proximal connector 5780a and the distal connector 5780b can secure the layer of material 5758 relative to the cartridge body 5750.

Referring primarily to FIG. 76, the cartridge body 5750 can include a deck 5752. A slot 5756 can extend from the proximal portion 5704 toward the distal portion 5706 of the second jaw 5702, and can be defined in a portion of the deck 5752, for example. In various embodiments, fastener cavities 5754 can be defined in the deck 5752. The second jaw 5702 can also include fasteners, such as surgical staplers, removably positioned in the fastener cavities 5754. For example, a fastener can be ejectably positioned in each fastener cavity 5754 of the cartridge body 5750. In various embodiments, the fasteners can be ejected from their respective fastener cavities 5754 in the cartridge body 5750 by a sled, similar to sled 5434 (FIGS. 65 and 66) during a firing stroke.

Referring still to FIGS. 76 and 77, a firing assembly, such as the firing assembly 5430 (FIGS. 65 and 66) can move along the slot 5756 in the cartridge body 5750 during the firing stroke. As described previously, the firing assembly 5430 can include a firing bar 5432, a cutting edge 5436, and a foot 5438 (FIGS. 65 and 66), for example. In various embodiments, the firing assembly 5430 can engage the sled in the cartridge body 5730 and can drive the sled at least partially through the cartridge body 5750 during the firing stroke. In certain embodiments, the sled can have a camming surface or ramp, which can engage drivers in the fasteners cavities 5754 during the firing stroke. When the ramp engages a driver in a fastener cavity 5754, the ramp can cam the driver and corresponding fastener toward the cartridge deck 5752, and can eject the fastener from the fastener cavity 5754, for example. In various embodiments, the cutting edge 5436 can cut the proximal connector 5780a and the distal connector 5780b (FIG. 77) during the firing stroke. The cutting edge 5436 can cut the proximal connector 5780a at or near the beginning of the firing stroke, for example, and can cut the distal connector 5780b at or near the end of the firing stroke, for example.

Referring still to FIGS. 76 and 77, the layer of material 5758 can be releasably secured to the deck 5752 of the cartridge body 5750 by the proximal connector 5780a and by the distal connector 5780b (FIG. 77). In various embodiments, the cartridge body 5750 can include at least one notch 5748a (FIG. 76), which can be defined in the deck 5752, for example. The notch 5748a can be positioned between the proximal connector 5780a and the distal connector 5780b, for example. Further, in various embodiments, the layer of material 5758 can include a mount 5760a (FIG. 76), which can be integrally molded with the layer of material 5758, for example. In certain embodiments, when the layer of material 5758 is secured to the deck 5752, the mount 5760a can extend from the layer of material 5758 into the notch 5748a of the cartridge body 5750. The mount 5760a can remain positioned within the notch 5748a to hold the layer of material 5758 relative to the deck 5752 of the cartridge body 5750. The mount 5760a can be sized to fit in the notch 5748a when the layer of material 5758 is positioned on the cartridge body 5750. Furthermore, the mount 5760a can be sized for unforced removal from the notch 5748a when the layer of material 5758 is lifted and/or peeled away from the cartridge body 5758. For example, the mount 5760 may not be friction fit in the notch 5748a, and, in certain embodiments, when the mount 5760a is positioned in the notch 5748a, a clearance or gap can exist between the mount 5760a and the notch 5748a. The clearance can be approximately 0.08 mm, for example. In certain embodiments, the clearance can be up to approximately 0.24 mm, for example. In some embodiments, an interference of approximately 0.01 mm to approximately 0.06 mm can exist between the mount 5760a and the notch 5748a, for example, such that the mount 5760a is compressed when positioned in the notch 5748a, for example.

In various embodiments, the mount-notch engagement can prevent and/or limit lateral shifting and/or buckling of the layer of material 5758 relative to the cartridge body 5750. For example, when the end effector assembly 5700 is placed and/or moved relative to tissue at a surgical site and/or when the cutting edge 5436 (FIGS. 65 and 66) cuts the layer of material 5758, the mount 5760a can remain positioned in the notch 5748a to hold the layer of material 5758 in position relative to the cartridge deck 5752. In certain embodiments, shifting of the layer of material 5758 relative to the cartridge body 5750 can be limited by the clearance defined between the mount 5760a and the notch 5748a. For example, some shifting of the layer of material 5758 may be possible owing to the clearance. Further, after the cutting edge 5436 cuts the proximal connector 5780a and the distal connector 5780b, the mount 5760a can smoothly disengage and/or be removed from the notch 5748a as the layer of material 5758 is lifted and/or peeled away from the cartridge body 5750.

Referring primarily to FIG. 76, the cartridge body 5750 can include at least one pair of notches 5748a, 5748b, and the layer of material 5758 can include a pair of mounts 5760a, 5760b. The first notch 5748a can be positioned on a first longitudinal side of the cartridge body 5750, for example, and the second notch 5748b can be positioned on a second longitudinal side of the cartridge body 5750, for example. In other words, each notch of the pair of notches 5748a, 5748b can be positioned on opposite sides of the slot 5756 in the cartridge body 5750. In certain embodiments, the second notch 5748b can be a mirror image reflection of the first notch 5748a across the slot 5756, for example. Further, when the layer of material 5758 is secured to the cartridge body 5750, each mount of the pair of mounts 5760a, 5760b can be aligned with a notch of the pair of notches 5748a, 5748b such that the first mount 5760a extends into the first notch 5748b and the second mount 5760b extends into the second notch 5748b. In various embodiments, the pair of notches 5748a, 5748b in the cartridge body 5750 can be positioned at the perimeter of the cartridge body 5750. Further, in certain embodiments, the pair of mounts 5760a, 5760b can be positioned at the perimeter of the layer of material 5758.

In various embodiments, the mount-notch engagement on both sides of the cartridge body 5750 can further prevent and/or limit lateral shifting and/or buckling of both longitudinal sides of the layer of material 5758. For example, when the cutting edge 5436 of the firing assembly 5430 (FIGS. 65 and 66) cuts the layer of material 5758, the pair of mounts 5760a, 5760b can remain positioned in the pair of notches 5748a, 5748b to hold the perimeter of the layer of material 5758 in position relative to the perimeter of the cartridge deck 5752. In other words, the pair of mounts 5760a, 5760b can prevent at least a portion of the layer of material 5758 from slipping laterally relative to the cartridge deck 5752. Further, as the layer of material 5758 is lifted and/or peeled away from the cartridge body 5750, for example, after the cutting edge 5436 cuts the proximal and distal connectors, the pair of mounts 5760a, 5760b can be easily and smoothly removed from the pair of notches 5748a, 5748b. In various embodiments, the layer of material 5758 can include multiple pairs of mounts 5760a, 5860b, and the cartridge body 5750 can include multiple pairs of notches 5748a, 5748b. When the layer of material 5758 is secured to the cartridge body 5750, each pair of mounts 5760a, 5760b of the layer of material 5758 can be aligned with a pair of notches 5748, for example. In such embodiments, the mount-notch engagement along a length of the perimeter of the lower jaw 5702 can further prevent and/or limit lateral shifting and/or buckling of a length of the layer of material 5758 relative to the cartridge body 5750.

Figure 78:
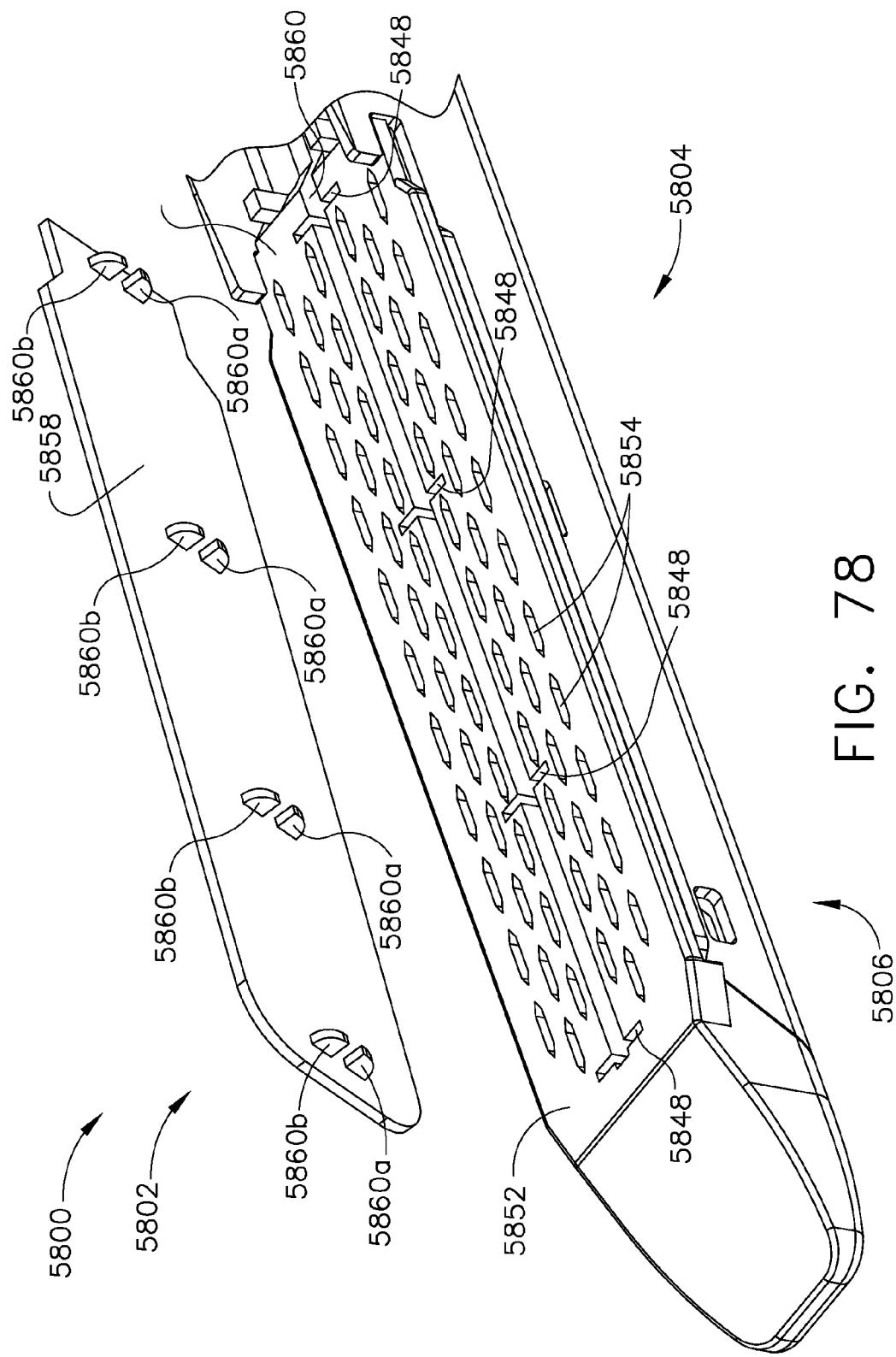
FIG. 78 is a perspective view of a fastener cartridge assembly for use with an end effector assembly according to various embodiments of the present disclosure, depicting a layer of material released from a cartridge body of the fastener cartridge assembly.
Figure 79:
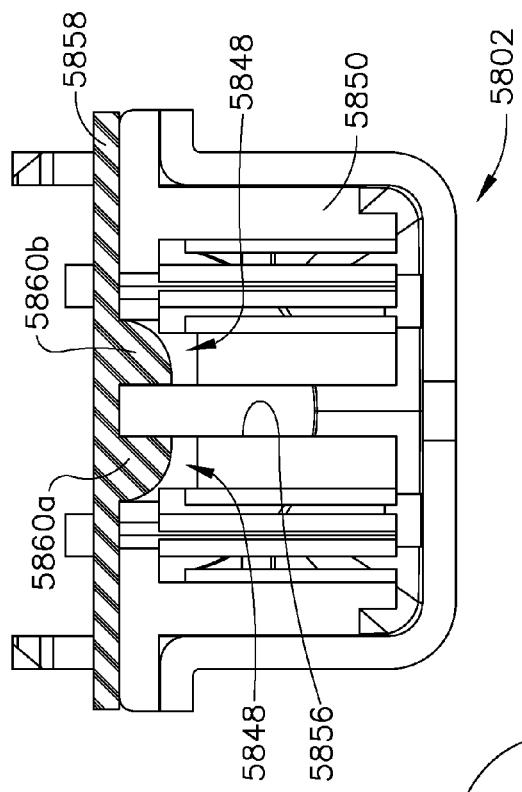
FIG. 79 is a cross-sectional, elevation view of the fastener cartridge assembly of FIG. 78, depicting the layer of material secured to the cartridge body.
Figure 80:
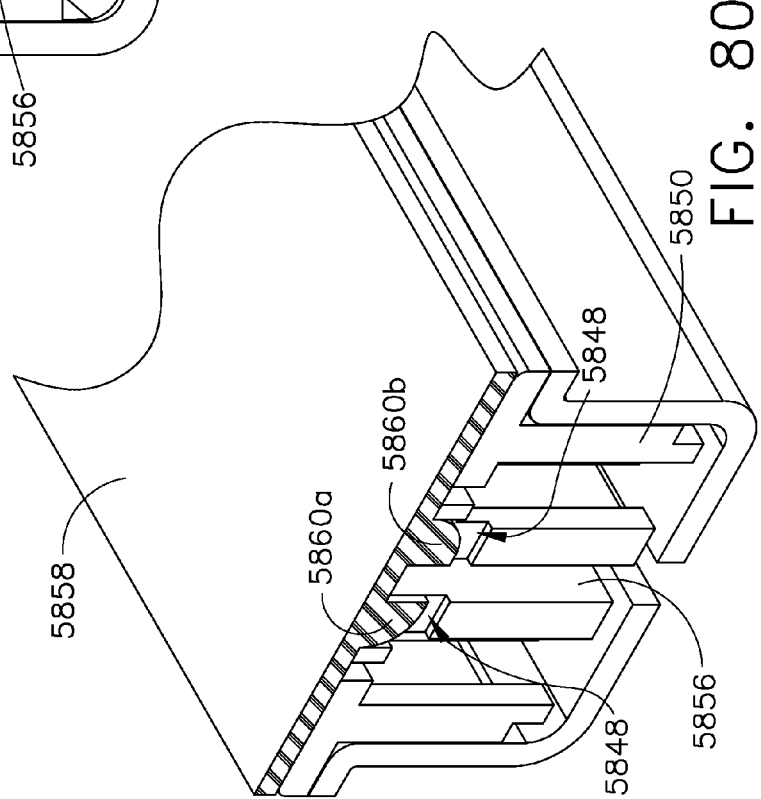
FIG. 80 is a cross-sectional, perspective view of the fastener cartridge assembly of FIG. 78, depicting the layer of material secured to the cartridge body.

Referring now to FIGS. 78-80, an end effector assembly 5800 can include a first jaw, illustrated elsewhere, and a second jaw 5802. In various embodiments, the second jaw 5802 can include a cartridge body 5850 and a layer of material 5858 releasably secured to the cartridge body 5850 and/or to the second jaw 5802. In various embodiments, the cartridge body 5850 and the layer of material 5858 releasably secured thereto can comprise a fastener cartridge assembly, for example. The layer of material 5858 can comprise a piece of buttress material and/or a tissue thickness compensator, for example. In certain embodiments, the layer of material 5858 can be a piece of buttress material releasably secured to the cartridge body 5850, for example. The second jaw 5802 can have a proximal portion 5804 and a distal portion 5806. In various embodiments, the second jaw 5802 can have a proximal connector, similar to proximal connector 5780a (FIG. 77), at the proximal portion 5804 and a distal connector, similar to distal connector 5880b (FIG. 77), at the distal portion 5406. The proximal connector and the distal connector can secure the layer of material 5858 relative to the cartridge body 5850.

Referring primarily to FIG. 78, the cartridge body 5850 can include a deck 5852. A slot 5856 can extend from the proximal portion 5804 toward the distal portion 5806 of the second jaw 5802, and can be defined in a portion of the deck 5852, for example. In various embodiments, fastener cavities 5854 can be defined in the deck 5852. The second jaw 5802 can also include fasteners, such as surgical staplers, removably positioned in the fastener cavities 5854. For example, a fastener can be ejectably positioned in each fastener cavity 5854 of the cartridge body 5850. In various embodiments, the fasteners can be ejected from their respective fastener cavities 5854 in the cartridge body 5850 by a sled, similar to sled 5434 (FIGS. 65 and 66) during a firing stroke.

A firing assembly, such as firing assembly 5430 (FIGS. 65 and 66) can move along the slot 5856 in the cartridge body 5850 during the firing stroke. The firing assembly 5430 can include a firing bar 5432, a cutting edge 5436, and a foot 5438, for example. In various embodiments, the firing assembly 5430 can engage the sled in the cartridge body 5850 and can drive the sled at least partially through the cartridge body 5850 during the firing stroke. In certain embodiments, the sled can have a camming surface or ramp, which can engage drivers in the fasteners cavities 5854 during the firing stroke. When the ramp engages a driver in a fastener cavity 5854, the ramp can cam the driver and the corresponding fastener toward the cartridge deck 5852, and can eject the fastener from the fastener cavity 5854, for example. In various embodiments, the cutting edge 5436 can cut the proximal and distal connectors during the firing stroke. The cutting edge 5436 can cut the proximal connector at or near the beginning of the firing stroke, for example, and can cut the distal connector at or near the end of the firing stroke, for example.

Referring still to FIGS. 78-80, the cartridge body 5850 can include at least one notch 5848, which can be defined in the deck 5852 (FIG. 78), for example. The notch 5848 can be positioned between the proximal connector and the distal connector, for example. Further, in various embodiments, the layer of material 5858 can include a pair of mounts 5860a, 5860b. The pair of mounts 5860a, 5860b can be integrally molded with the layer of material 5858, for example. In certain embodiments, when the layer of material 5858 is secured to the deck 5852, the pair of mounts 5860a, 5860b can extend from the layer of material 5858 into the notch 5848 of the cartridge body 5850. The pair of mounts 5860a, 5860b can be positioned the notch 5848 to hold the layer of material 5858 relative to the deck 5852 of the cartridge body 5850. In various embodiments, the pair of mounts 5860a, 5860b can be sized to fit in the notch 5848 when the layer of material 5858 is positioned on the cartridge body 5850. Furthermore, the pair of mounts 5860a, 5860b can be sized for unforced removal from the notch 5848 when the layer of material 5858 is lifted and/or peeled from the cartridge body 5858. In certain embodiments, when the pair of mounts 5860a, 5860b are positioned within the notch 5848, a clearance or gap can exist between each mount 5860a, 5860b and the notch 5848. The clearance can be approximately 0.12 mm, for example. In certain embodiments, the clearance can be up to approximately 0.24 mm, for example. In some embodiments, an interference of approximately 0.01 mm to approximately 0.18 mm can exist between the each mount 5860a, 5860b and the notch 5848, for example, such that each mount 5860a, 5860b is compressed when positioned in the notch 5848, for example.

In various embodiments, the mount-notch engagement can prevent and/or limit lateral shifting and/or buckling of the layer of material 5858. For example, when the cutting edge 5436 (FIGS. 65 and 66) cuts the layer of material 5858, the pair of mounts 5860a, 5860b can remain positioned in the notch 5848 to hold the layer of material 5858 in position relative to the cartridge deck 5852. Shifting of the layer of material 5858 relative to the cartridge body 5850 can be limited by the clearance defined between each mount 5860a, 5860b and the notch 5848, for example. For example, some shifting of the layer of material 5858 may be possible owing to the clearance. In various embodiments, the mounts 5860a, 5860b may not resist lifting and/or peeling of the layer of material 5858 away from the cartridge body 5850. For example, the mounts 5860a, 5860b may not be friction fit in the notch 5848, and the mounts 5860a, 5860b can be easily and smoothly removed from the notch 5848 when the layer of material is lifted away from the deck of the cartridge body 5850, for example, after the cutting edge 5436 cuts the proximal and distal connectors.

Referring primarily to FIG. 78, the notch 5848 can extend from the slot 5856 in the cartridge body 5850, and can intersect the slot 5856, for example. In such embodiments, when the pair of mounts 5860a, 5860b extends into the notch 5848, the mount 5860a can be positioned on a first side of the slot 5856 and the mount 5860b can be positioned on a second side of the slot 5856, for example. In certain embodiments, the mount 5860b can be a mirror image reflection of the mount 5860b across the slot 5856, for example. Further, referring primarily to FIG. 79, the pair of mounts 5860a, 5860b may not overlap the slot 5856, for example. In such embodiments, the cutting edge 5436 of the firing assembly 5430 (FIGS. 65 and 66) can transect the layer of material 5858 during the firing stroke without cutting the mounts 5860a, 5860b, for example. In other words, the firing assembly 5430 can pass between the pair of mounts 5860a, 5860b during the firing stroke. In such embodiments, the mount-notch engagement on both sides of the slot 5856 can further prevent and/or limit lateral shifting and/or buckling of both longitudinal sides of the layer of material 5858, for example. Referring primarily to FIG. 78, the cartridge body 5850 can include multiple notches 5848 spaced along a portion of the length of the cartridge body 5850. Further, the layer of material 5858 can include multiple pairs of mounts 5860a, 5860b. When the layer of material 5858 is secured to the cartridge body 5850, the pairs of mounts 5860a, 5860b of the layer of material 5758 can be aligned with the notches 5748, for example. In such embodiments, the mount-notch engagement along a portion of the length of the lower jaw 5802 can further prevent and/or limit lateral shifting and/or buckling of a length of the layer of material 5858.

Referring now to FIGS. 80A and 80B, a layer of material 5958 for use with an end effector can have a perimeter 5970 that defines the edge of the layer of material 5958. In various embodiments, the layer of material 5958 can be a piece of buttress material or a tissue thickness compensator, for example. Further, the perimeter 5970 can include contours 5974 and indentations 5972. In various embodiments, an indentation 5972 can be positioned intermediate each contour 5974 to form a scalloped edge along at least a portion of the perimeter 5970. In various embodiments, the perimeter can be a scalloped perimeter. In certain embodiments, a portion of the perimeter 5970 can be a scalloped perimeter, and a portion of the perimeter can be a non-scalloped perimeter. The scalloped edge of the perimeter 5970 can prevent and/or limit abrasions and/or other damage to tissue that contacts the perimeter 5970 while the layer of material 5958 is positioned relative to the surgical site.

Referring still to FIGS. 80A and 80B, the layer of material 5958 can include a top surface 5962 (FIG. 80A) and a bottom surface 5966 (FIG. 80B). The top surface 5962 can be positioned relative to the first jaw or anvil of an end effector, for example, and the bottom surface 5966 can be positioned relative to a second jaw or fastener cartridge of the end effector, for example. In various embodiments, the layer of material 5958 can include a proximal portion 5904 and a distal portion 5906. In certain embodiments, the layer of material 5958 can include a mount 5960, 5964 extending from the top surface 5962 and/or the bottom surface 5966 thereof. In various embodiments, the mount 5960, 5964 can be positioned in an indentation or notch in the end effector 5902, such as a notch in the cartridge body and/or in the anvil. In certain embodiments, the mount 5960, 5964 can support, reinforce and/or rigidify the layer of material 5958. For example, when the cutting edge 5436 (FIGS. 65 and 66) traverses the layer of material 5958 during a firing stroke, the mount 5960 can prevent and/or limit shifting and/or buckling of the layer of material 5958 relative to the cartridge body. Further, one of the mounts 5960, 5964 can engage tissue clamped between the first jaw and the second jaw of the end effector 5902, for example. In such embodiments, the mount 5960, 5964 can prevent and/or limiting shifting of the clamped tissue relative to the cartridge body, for example. Referring primarily to FIG. 80A, the mount 5960 can be at the distal portion 5906 of the layer of material 5958. The mount 5960 can include multiple projections or buttons extending from the top surface 5962, for example. In various embodiments, the buttons of the mount 5960 can be arranged in a triangle, for example. Referring primarily to FIG. 80B, the mount 5964 can extend from the bottom surface 5966 of the layer of material 5958, for example. The mount 5964 can be at the distal portion 5906 of the layer of material 5958, and can be V-shaped, for example.

Referring now to FIGS. 81-84, an end effector assembly 5000 can include a first jaw, illustrated elsewhere, and a second jaw 5002. In various embodiments, the second jaw 5002 can include a fastener cartridge assembly comprising a fastener cartridge body 5050 and a layer of material 5058 releasably secured to the fastener cartridge body 5050. In various embodiments, the layer of material 5058 can comprise a tissue thickness compensator and/or piece of buttress material. For example, the layer of material 5058 can be a piece of buttress material releasably secured to the fastener cartridge body 5050. Referring primarily to FIG. 81, the fastener cartridge body 5050 can have fastener cavities 5054 defined therein. Further, the second jaw 5002 and/or the fastener cartridge body 5050 can include fasteners, such as surgical staples, for example, which can be removably positioned in the fastener cavities 5054. For example, a fastener can be ejectably positioned in each fastener cavity 5054 of the cartridge body 5050. In certain embodiments, the cartridge body 5050 can include a slot 5056, which can extend from a proximal portion 5004 of the second jaw 5002 toward a distal portion 5006 of the second jaw 5002. In various embodiments, a firing assembly 5030 can translate along the slot 5056 of the cartridge body 5050. For example, the firing assembly 5030 can translate within the slot 5056 during a firing stroke, and can eject the fasteners from the fastener cavities 5054 during the firing stroke.

Referring still to FIGS. 81-84, the firing assembly 5030 can include a firing bar, a cutting edge 5036 (FIGS. 81 and 82), a crossbar 5038 (FIGS. 81 and 82), a nose 5040 (FIG. 81) and a foot 5034. The cutting edge 5036 can cut tissue and/or cut the layer of material 5058 as the firing assembly 5030 is fired through the second jaw 5002 during a firing stroke. The crossbar 5038 can engage the first jaw, such as a slot in the anvil thereof, to hold the first jaw relative to the cartridge body 5050, and the foot 5034 can engage the second jaw 5002, such as the slot 5056 (FIG. 81) in the cartridge body 5050, to hold the firing assembly 5030 relative to the cartridge body 5050, for example. In various embodiments, the firing assembly 5030 can engage a sled in the cartridge body 5050 during the firing stroke. An element of the firing assembly 5030, such as the nose 5040, for example, can engage the sled and push the sled distally during the firing stroke to eject fasteners from the fastener cavities 5054, for example.

Referring primarily to FIG. 81, the layer of material 5058 can be releasably secured to the cartridge body 5050 by at least one connector. In certain embodiments, multiple connectors can secure the layer of material 5058 to the cartridge body 5050. For example, a proximal connector can secure the layer of material 5058 to the cartridge body 5050 at the proximal portion 5004 of the second jaw 5002, and a distal connector 5080 can secure the layer of material 5058 to the cartridge body 5050 at the distal portion 5006 of the second jaw 5002. In various embodiments, a mount 5064 can extend from the layer of material 5058 at the distal portion of the second jaw 5002. The distal connector 5080 can extend or wrap around at least part of the second jaw 5002 and/or the cartridge body 5050, as well as the mount 5064 to hold the layer of material 5058 relative to the cartridge body 5050, for example. In certain embodiments, additional connectors can secure the layer of material 5058 to the cartridge body 5050. In such embodiments, the additional connectors can be spaced along at least a portion of the length of the cartridge body 5050, and can be positioned between the proximal connector and the distal connector 5080, for example. In various embodiments, a connector can be a band, a tie, and/or a suture, and can include braided and/or intertwined fibers, for example. The end of a cut and/or severed connector may be sharp, for example, and may pierce and/or lacerate adjacent tissue as the surgeon removes the end effector assembly from the patient's tissue. However, the end of a braided connector can be less sharp than the end of a non-braided connector. For example, the cut end of a braided connector may fray, which can result in a less sharp end. With braided connectors, puncturing and/or lacerations to the tissue by the cut and/or severed end of the connector can be reduced and/or substantially eliminated. In various embodiments, a braided connector can have at least substantially the same tensile holding strength as a non-braided connector, for example. Further, in certain embodiments, when cut and/or severed, a braided connector can have substantially less compressive strength than a non-braided connector, for example.

Still referring primarily to FIG. 81, the distal connector 5080 can hold the layer of material 5058 relative to the cartridge body 5050. The layer of material 5058 can be released from the cartridge body 5050 when the distal connector 5080, as well as any additional connectors, are broken, cut, dislodged or otherwise overcome. In certain embodiments, the firing assembly 5030 can overcome the distal connector 5080 as the firing assembly 5030 translates along the slot 5056 in the fastener cartridge 5050 during a firing stroke. For example, during the firing stroke, the firing assembly 5030 can cut tissue clamped between the first jaw and the second jaw 5002, and can also move the fasteners from the fastener cavities 5054 into the clamped tissue and the layer of material 5058. In various embodiments, the firing assembly 5030 can push the sled distally during the firing stroke. The sled can have a camming surface or ramp, for example, which can engage drivers in the fastener cavities 5054. When the ramp engages a driver, the ramp can push the driver toward the layer of material 5058 to eject the fastener from the fastener cavity 5054. Further, the firing assembly 5030 can cut the layer of material 5058 and/or the distal connector 5080 during the firing stroke.

Referring still to FIGS. 81-84, in various embodiments, the second jaw 5002 can overcome the connector or connectors, such as or including the distal connector 5080, at or near the beginning of the firing stroke. In other words, an element of the second jaw 5002 can overcome the distal connector 5080 at or near the beginning of the firing stroke. The second jaw 5002 and/or the fastener cartridge assembly can include an actuator 5010, for example, which can overcome the distal connector 5080 before the fasteners are ejected from the fastener cavities 5054. The actuator 5010 can overcome the distal connector 5080, and the layer of material 5058 can be released from the cartridge body 5050 even when the firing stroke terminates prematurely, i.e., before the firing assembly 5030 reaches the distal portion 5006 of the second jaw 5002, for example. In various embodiments, the actuator 5010 can include a bottom side 5016, sidewalls 5018, and/or rims 5026. The sidewalls 5018 can extend from the bottom side 5016 and around at least a portion of the cartridge body 5050. The rims 5026 can extend from the sidewalls 5018 and around at least a portion of the cartridge body 5050. In various embodiments, the rims 5026 can extend into slits 5052 in the cartridge body 5050, for example. The bottom side 5016, the sidewalls 5018, and/or the rims 5026 can extend past and/or around the cartridge body 5050 and the fasteners positioned in the fastener cavities 5054 thereof. Further, the actuator 5010 can be moveably held relative to the cartridge body 5050. For example, the actuator 5010 can move from a pre-actuated position (FIG. 81) to an actuated position (FIG. 82). In certain embodiments, the rims 5026 of the actuator 5010 can slide in the slits 5052 in the cartridge body 5050 when the actuator 5010 moves relative to the cartridge body 5050. When the actuator 5010 moves relative to the cartridge body 5050, the actuator 5010 can slide relative to the fasteners positioned in the fastener cavities 5054 of the cartridge body 5050. For example, the actuator 5010 can slide past and/or around the fasteners positioned in the cartridge body 5050.

Referring primarily to FIGS. 81-84, the actuator 5010 can include a slot 5012, which can extend from the proximal portion 5004 toward the distal portion 5006 of the second jaw 5002 when the actuator 5010 is positioned relative to the cartridge body 5050. The slot 5012 in the actuator 5010 can correspond to and/or be aligned with the slot 5056 (FIG. 81) in the cartridge body 5050, for example. Further, the firing assembly 5030 can translate within the slot 5012 in the actuator 5010 as the firing assembly 5030 translates within the slot 5056 in the cartridge body 5050 during the firing stroke. In various embodiments, the firing assembly 5030 can engage the actuator 5010 to move the actuator 5010 distally when the firing assembly 5030 is at or near the beginning of the firing stroke. In such embodiments, the firing assembly 5030 can actuate the actuator 5010 at the proximal portion 5004 of the second jaw 5002. When the actuator 5010 is actuated and moves distally, a distal end of the actuator 5010 can cut or otherwise overcome the distal connector 5080, for example. In other words, the proximal actuation of the actuator 5010 can effectuate the distal release of the layer of material 5058 from the cartridge body 5050. In various embodiments, the actuator 5010 can merely shift distally to overcome the distal connector 5080. In at least one embodiment, the actuator 5010 can shift approximately 1.0 mm before overcoming the distal connector 5080. In certain embodiments, the actuator 5010 can shift approximately 0.5 mm to approximately 5.0 mm before overcoming the distal connector 5180.

Referring primarily to FIGS. 81 and 82, the actuator 5010 can move from the pre-actuated position (FIG. 81) to the actuated position (FIG. 82) when the firing assembly 5030 moves between an unfired position and a partially fired position during part of the firing stroke. In various embodiments, the slot 5012 in the actuator 5010 can include a release stop 5014. The release stop 5014 can include a frangible bridge across the slot 5012, for example. Referring primarily to FIG. 82, an element of the firing assembly 5030 can push against the release stop 5014 as the firing assembly 5030 translates along the slot 5056 (FIG. 81) during the firing stroke. The firing assembly 5030 can push against the release stop 5014 at or near the beginning of the firing stroke, for example. In certain embodiments, the release stop 5014 can be near the proximal end of the slot 5012, and an element of the firing assembly 5030, such as the nose 5040, can abut the release stop 5014 upon the initiation of the firing stroke. When the nose 5040 is positioned against the release stop 5014, the nose 5040 can push against the actuator 5010 and move the actuator 5010 distally. In certain embodiments, referring primarily to FIG. 82, the actuator 5010 can be moved distally until it reaches a hard stop 5060, for example. The hard stop 5060 can be at the distal portion 5006 of the second jaw 5002, and can prevent further distal movement of the actuator 5010, for example. In various embodiments, the actuator 5010 can abut the hard stop 5060 before the firing assembly 5030 ejects the fasteners from the fastener cavities 5054. In certain embodiments, the actuator can abut the hard stop 5060 as the firing assembly 5030 ejects at least one fastener from a fastener cavity 5054 and/or after the firing assembly 5030 ejects at least one fastener from a fastener cavity 5054.

Referring still to FIG. 82, when the actuator 5010 is pushed distally by the firing assembly 5030, the actuator 5010 can cut or otherwise overcome the distal connector 5080 to release the layer of material 5058 from the cartridge body 5050 at the distal portion 5006 of the second jaw 5002. In certain embodiments, the actuator 5010 can include a notch 5024 for receiving and holding the distal connector 5080. The notch 5024 can hold the distal connector 5080 as the actuator 5010 shifts distally toward the hard stop 5060. Further, the actuator 5010 can include a cutting edge 5020, for example, along a portion of the notch 5024. In certain embodiments, when the actuator 5010 moves toward the hard stop 5060, the distal connector 5080 can be pushed between the hard stop 5060 and the cutting edge 5020 of the actuator 5010. In various embodiments, the cutting edge 5020 can cut the distal connector 5080 when the cutting edge 5020 is pushed into the hard stop 5060. In such embodiments, the distal connector 5080 can be cut by the cutting edge 5020 of the actuator 5010 at or near the beginning of the firing stroke and before the fasteners are fired from the fastener cavities 5054. In various embodiments, the actuator 5010 can overcome the distal connector 5080 without cutting it. For example, the actuator 5010 can dislodge or stretch the distal connector 5080 out of position such that the distal connector 5080 no longer holds the layer of material 5058 relative to the cartridge body 5050. In various embodiments, distal movement of the actuator 5010 can overcome or unlock a restraint, such as a cam-lock, that locks and/or tightens the distal connector 5080 around the layer of material 5058. For example, referring to FIG. 30, a restraint 694 can be positioned in the lower jaw 680 and, for example, can be positioned between the pan 680a and the cartridge body 682. In various embodiments, the restraint 694 can be used when assembling the end effector, and the connector S3 can be connected thereto. When the restraint 694 is pushed and secured in place, the restraint 694 can tighten the connector S3 around the layer B2, and can be adjustably positioned to adjust the tightness of the connector S3 around the layer B2. In various embodiments, referring again to FIG. 82, the actuator 5010 can unlock a restraint, such as restraint 694 (FIG. 30), for example. The actuator 5010 can cam the restraint, such that the restraint loosens and/or releases the distal connector 5080.

In various embodiments, additional connectors along the length of the cartridge body 5050 can be cut or otherwise overcome by the actuator 5010 at or near the beginning of the firing stroke. For example, a proximal cutting edge on the actuator 5010 can cut an additional proximal connector, and/or an intermediate cutting edge on the actuator 5010 can cut an additional immediate connector. The various cutting edges and/or portions of the actuator 5010 can cut or otherwise overcome each of the connectors at and/or near the beginning of the firing stroke. Additionally or alternatively, the cutting edge 5036 of the firing assembly 5030 can cut or otherwise overcome the additional connectors. For example, the cutting edge 5036 of the firing assembly 5030 can cut a connector at the proximal portion 5004 of the second jaw 5002 and the cutting edge 5020 of the actuator 5010 can cut the distal connector 5080 before the fasteners are ejected from the fastener cavities 5054 of the cartridge body 5050. In certain embodiments, the actuator 5010 can over the distal connector 5080 as at least one fastener is ejected from a fastener cavity 5054 and/or after at least one fastener is ejected from a fastener cavity 5054.

Referring primarily to FIGS. 83 and 84, when the actuator 5010 is blocked from further distal movement by the hard stop 5060, the firing assembly 5030 can push through the release stop 5014 in the slot 5012 of the actuator 5010. For example, the nose 5040 of the firing assembly 5030 can break the frangible bridge of the release stop 5014 to continue moving distally along the slot 5012 during the firing stroke. The frangible bridge can be sufficiently rigid to withstand the force of the firing assembly 5030 as the actuator 5010 shifts distally toward the hard stop 5060, and can be sufficiently frangible to break when the actuator 5010 reaches the hard stop 5060 without requiring excessive force by a motor and/or an operator. The actuator 5010 and/or the frangible bridge thereof can comprise stainless steel, titanium, aluminum, liquid crystal polymer (LCP), nylon and/or ultem, for example. In certain embodiments, the actuator 5010 can comprise stainless steel and the frangible bridge can comprise a thin piece of stainless steel. In certain embodiments, the frangible bridge can include a perforation, which can increase the frangibility thereof. The size and shape of the perforation can be selected such that the frangible bridge is appropriately breakable. In various embodiments, the actuator 5010 can overcome the distal connector 5080 before a fastener is fired from the fastener cartridge 5050. In certain embodiments, at least one fastener can be fired from a fastener cavity before or while the actuator 5010 overcomes the distal connector 5080. Upon breaking through the release stop 5014, the firing assembly 5030 can continue to move distally along the slot 5056 (FIG. 81) in the cartridge body 5050 and along the slot 5012 in the actuator 5010 to eject fasteners from the fastener cartridge 5050 during the remaining portion of the firing stroke. Stated differently, the firing assembly 5030 can actuate the actuator during a first stage or portion of the firing stroke, and can fire fasteners from the fastener cavities 5054 and/or cut tissue and/or the layer of material 5058 during a second stage or portion of the firing stroke.

Referring now to FIGS. 85 and 86, an end effector assembly can include a first jaw 5102 and a second jaw, illustrated elsewhere. In various embodiments, the first jaw 5102 can include an anvil frame 5170 and a layer of material releasably secured to the anvil frame 5170. The layer of material can comprise a tissue thickness compensator and/or a piece of buttress material, for example, similar to the layer of material 5058 (FIGS. 81-84). For example, the layer of material can be a piece of buttress material releasably secured to the anvil frame 5170. In certain embodiments, the anvil frame 5170 can include a slot 5172, which can extend from a proximal portion 5104 of the first jaw 5102 toward a distal portion 5106 of the first jaw 5102. In various embodiments, a firing assembly 5130 can translate along the slot 5172 of the anvil frame 5170. For example, the firing assembly 5130 can translate along the slot 5172 during a firing stroke. The translation of the firing assembly 5130 along the slot 5172 can correspond to the translation of a firing element through the second jaw of the end effector assembly. As the firing element translates through the second jaw, for example, the firing element can eject fasteners from the second jaw into the layer of material and the tissue clamped between the first jaw 5102 and the second jaw. Referring primarily to FIG. 85, the firing assembly 5130 can include a firing bar 5132 and a nose 5136. In various embodiments, the nose 5136 of the firing assembly 5130 can include a cutting edge for cutting tissue and the layer of material clamped between the first jaw 5102 and the second jaw.

Referring primarily to FIG. 85, the layer of material can be releasably secured to the anvil frame 5170 by at least one connector. In certain embodiments, multiple connectors can secure the layer of material to the anvil frame 5170. For example, a proximal connector can secure the layer of material to the anvil frame 5170 at the proximal portion 5104 of the first jaw 5102, and a distal connector 5180 can secure the layer of material to the anvil frame 5170 at the distal portion 5106 of the first jaw 5102. In certain embodiments, additional connectors can secure the layer of material to the anvil frame 5170. In such embodiments, the additional connectors can be spaced along at least a portion of the length of the anvil frame 5170, and can be positioned between the proximal connector and the distal connector 5180, for example.

Still referring primarily to FIG. 85, the distal connector 5180 can hold the layer of material relative to the anvil frame 5170. The layer of material can be released from the anvil frame 5170 when the distal connector 5180 and any additional connectors are broken, cut, dislodged or otherwise overcome. In certain embodiments, the firing assembly 5130 can overcome the distal connector 5180 as the firing assembly 5130 translates along the slot 5172 in the anvil frame 5170 during a firing stroke. In various embodiments, an element of the first jaw 5102 can overcome the connector or connectors, such as or including distal connector 5180, at or near the beginning of the firing stroke. In other words, the first jaw 5102 can overcome the distal connector 5180 at or near the beginning of the firing stroke and before a fastener is ejected into the clamped tissue. In various embodiments, the first jaw 5102 can include an actuator 5110, for example, which can overcome the distal connector 5080 at or near the beginning of the firing stroke. The actuator 5110 can overcome the distal connector 5180, and the layer of material 5158 can be released from the anvil frame 5170 even when the firing stroke terminates prematurely, i.e., before the firing assembly 5130 reaches the distal portion 5106 of the first jaw 5102, for example. In various embodiments, the actuator 5110 can comprise a longitudinal plate that extends along a length of the anvil frame 5170. In certain embodiments, the plate can include a longitudinal portion on one side of the anvil slot 5172, another longitudinal portion on another side of the anvil slot 5172, and a distal bridge 5174 extending between the longitudinal portions to reinforce the distal end of the actuator 5110. The actuator 5110 can extend through the first jaw 5102, and can be positioned between a fastener forming surface and an outer surface of the first jaw 5102, for example. Further, the actuator 5110 can be moveably held relative to the anvil frame 5170. For example, the actuator 5110 can move from a pre-actuated position (FIG. 85) to an actuated position (FIG. 86).

Referring primarily to FIG. 85, the actuator 5110 can include a slot 5112, which can extend from the proximal portion 5104 toward the distal portion 5106 of the first jaw 5102 when the actuator 5110 is positioned relative to the anvil frame 5170. The slot 5112 in the actuator 5110 can correspond to and/or be aligned with the slot 5172 in the anvil frame 5170, for example. Further, the firing assembly 5130 can translate along the slot 5112 in the actuator 5110 as the firing assembly 5130 translates along the slot 5172 in the anvil frame 5170 during the firing stroke. In various embodiments, the firing assembly 5130 can engage the actuator 5110 to move the actuator 5110 distally when the firing assembly 5130 is at or near the beginning of the firing stroke. In such embodiments, the firing assembly 5130 can actuate the actuator 5110 at the proximal portion 5104 of the first jaw 5102. When the actuator 5110 is actuated and moves distally, a distal end of the actuator 5110 can cut or otherwise overcome the distal connector 5180, for example. In other words, the proximal actuation of the actuator 5110 can effectuate the distal release of the layer of material from the anvil frame 5172. In various embodiments, the actuator 5110 can merely shift distally to overcome the distal connector 5180. In at least one embodiment, the actuator 5110 can shift approximately 1.0 mm before overcoming the distal connector 5180. In certain embodiments, the actuator 5110 can shift approximately 0.5 mm to approximately 5.0 mm before overcoming the distal connector 5180

Referring still to FIGS. 85 and 86, the actuator 5110 can move from the pre-actuated position (FIG. 85) to the actuated position (FIG. 86) when the firing assembly 5130 moves between an unfired position and a partially fired position during part of the firing stroke. In various embodiments, the slot 5112 in the actuator 5110 can include a release stop 5114. The release stop 5114 can have a narrower width than the portions of the slot 5112 adjacent to the release stop 5114, for example. Referring primarily to FIG. 85, an element of the firing assembly 5130 can push against the release stop 5114 as the firing assembly 5130 translates along the slot 5172 during the firing stroke. The firing assembly 5130 can push against the release stop 5114 at or near the beginning of the firing stroke, for example. In certain embodiments, the release stop 5114 can be near the proximal end of the slot 5112, and an element of the firing assembly 5130, such as the nose 5136, can abut the release stop 5114 upon the initiation of the firing stroke. When the nose 5136 is positioned against the release stop 5114, the nose 5136 can push against the actuator 5110 and move the actuator 5110 distally. In certain embodiments, the actuator 5110 can move distally until it reaches a hard stop 5160, for example. The hard stop 5160 can be at the distal portion 5106 of the first jaw 5102 and/or the anvil frame 5170, and can prevent further distal movement of the actuator 5110, for example.

Referring primarily to FIG. 86, when the actuator 5110 is pushed distally by the firing assembly 5130, the actuator 5110 can cut or otherwise overcome the distal connector 5180 to release the layer of material from the anvil frame 5172 at the distal portion 5106 of the first jaw 5102. In certain embodiments, the actuator 5110 can include a notch 5124 for receiving and holding the distal connector 5180. The notch 5124 can hold the distal connector 5180 as the actuator 5110 shifts distally toward the hard stop 5160. Further, the actuator 5110 can include a cutting edge 5120, for example, along the notch 5124. In certain embodiments, when the actuator 5110 moves toward the hard stop 5160, the distal connector 5180 can be pushed between the hard stop 5160 and the cutting edge 5120 of the actuator 5110. In various embodiments, the cutting edge 5120 can cut the distal connector 5180 when the cutting edge 5120 is pushed into the hard stop 5160. In such embodiments, the distal connector 5080 can be cut by the cutting edge 5120 of the actuator 5110 at or near the beginning of the firing stroke. In various embodiments, the actuator 5110 can overcome the distal connector 5180 without cutting it. For example, the actuator 5110 can dislodge or stretch the distal connector 5180 out of position such that the distal connector 5180 no longer holds the layer of material relative to the anvil frame 5170.

In various embodiments, additional connectors along the length of the anvil frame 5170 can be cut or otherwise overcome by the actuator 5110 at or near the beginning of the firing stroke. For example, a proximal cutting edge on the actuator 5110 can cut an additional proximal connector and/or an intermediate cutting edge on the actuator 5110 can cut an additional intermediate connector. The various cutting edges and/or portions of the actuator 5110 can cut or otherwise overcome each of the connectors at and/or near the beginning of the firing stroke. Additionally or alternatively, a cutting edge of the firing assembly 5130 can cut or otherwise overcome the additional connectors. For example, the firing assembly cutting edge can cut a connector at the proximal portion 5104 of the first jaw 5102 and the cutting edge 5120 of the actuator 5110 can cut the distal connector 5180 before the fasteners are ejected from the cartridge body of the second jaw. In certain embodiments, the actuator 5110 can overcome the distal connector 5180 as at least one fastener is ejected from a fastener cavity and/or after at least one fastener has been ejected from a fastener cavity. When the actuator 5110 is blocked from further distal movement by the hard stop 5160, the firing assembly 5130 can push through the release stop 5114 in the slot 5112 of the actuator 5110. When the firing assembly 5130 pushes through the release stop 5114, the firing assembly 5130 can widen the width of the slot 5112 to permit passage of the firing assembly 5130 therethrough. For example, the nose 5136 of the firing assembly 5130 can widen the release stop 5114 such that the firing bar 5132 can extend through the release stop 5114 and translate along the slot 5112. In various embodiments, the release stop 5114 can be sufficiently rigid to withstand the force of the firing assembly 5130 as the actuator 5110 shifts distally toward the hard stop 5160, and can be sufficiently flexible to widen when the actuator 5110 reaches the hard stop 5160 without requiring excessive force by a motor and/or an operator. The actuator 5110 and/or the release stop 5114 thereof can comprise stainless steel, titanium, aluminum, liquid crystal polymer (LCP), nylon and/or ultem, for example. In various embodiments, the actuator 5110 can overcome the distal connector 5180 before a fastener is fired from the fastener cartridge of the second jaw. In certain embodiments, the distal connector 5180 can be overcome after and/or while at least one fastener is ejected from a fastener cavity. Upon extending through the release stop 5114, the firing assembly 5130 can continue to move distally along the slot 5172 in the anvil frame 5172 and along the slot 5112 in the actuator 5110.

In various embodiments, an actuator can shift proximally when actuated by the firing assembly. The proximally-shifting actuator can overcome a proximal connector, for example. In certain embodiments, a first piece of an actuator can shift distally when actuated and a second piece of the actuator can shift proximally when actuated. The first and second pieces of the actuator can simultaneously overcome the connectors. For example, the first piece of the actuator can overcome a proximal connector as the second piece of the actuator overcomes the distal connector.

In various embodiments, an end effector assembly can include a first jaw and a second jaw. In certain embodiments, a layer of material can be releasably secured to the first jaw and another layer of material can be releasably secured to the second jaw. For example, a first layer of material can be releasably secured to a first jaw and/or an anvil frame, and a second layer of material can be releasably secured to a second jaw and/or a fastener cartridge assembly. In certain embodiments, an actuator, such as actuator 5010, for example, can release the first layer of material from the first jaw, and a second actuator, such as actuator 5110, for example, can release the second layer of material from the second jaw. The release of the first layer of material by the first actuator and the second layer of material by the second actuator can be timed. For example, the actuators can be arranged and/or configured such that the first and second layers of material can be released from the end effector assembly simultaneously and/or consecutively.

Referring generally to FIGS. 87-90, an end effector of a surgical stapling instrument can comprise a first jaw and a second jaw, wherein at least one of the first jaw and the second jaw can be configured to be moved relative to the other. The end effector can comprise a first jaw including a staple cartridge channel and a second jaw including an anvil such as, for example, anvil 2030 (FIG. 88A) which may include a plurality of forming pockets 2032 (FIG. 88A), wherein the anvil 2030 can be pivoted toward and/or away from the staple cartridge channel. The staple cartridge channel can be configured to receive a staple cartridge 2010 (FIG. 87) which can be removably retained within the staple cartridge channel. Tissue T can be captured between anvil 2030 and staple cartridge 2010, for example, when anvil 2030 is pivoted toward the staple cartridge channel.

Figure 87:
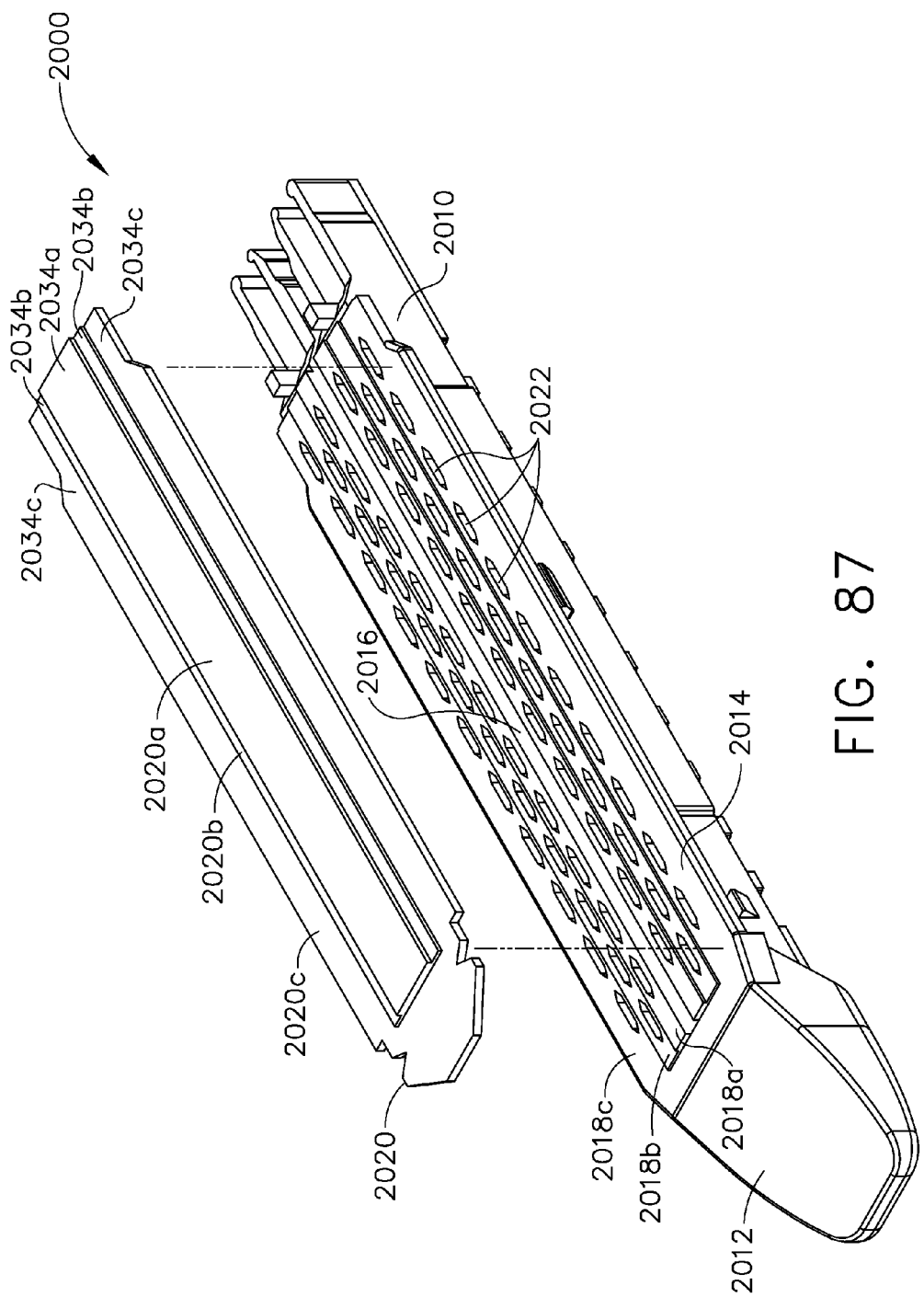
FIG. 87 is an exploded view of a staple cartridge and a tissue thickness compensator in accordance with at least one embodiment.

Referring primarily to FIG. 87, a staple cartridge assembly such as, for example, staple cartridge assembly 2000 can comprise a tissue thickness compensator, such as tissue thickness compensator 2020 and a staple cartridge, such as staple cartridge 2010, for example, which may comprise a cartridge body 2012 and a multistep cartridge deck 2014. As illustrated in FIG. 87, cartridge deck 2014 may comprise a slot 2016 extending longitudinally therethrough, wherein the slot 2016 can be configured to receive a cutting member which can be slidably moved through slot 2016.

Further to the above, as illustrated in FIG. 87, cartridge deck 2014 may comprise a plurality of surfaces 2018a-c extending longitudinally along slot 2016, wherein surface 2018a may lie closer to slot 2016 than surface 2018b which may lie closer to slot 2016 than surface 2018c. For example, surface 2018b may be laterally offset from surface 2018a in a direction away from slot 2016 and surface 2018c may be laterally offset from surface 2018b also in a direction away from slot 2016. In addition, surfaces 2018a-c can be vertically offset from each other. For example, surfaces 2018a-c may each lie, or at least substantially lie, in a separate plane wherein the planes of surfaces 2018a-c can be vertically offset from each other.

Further to the above, referring again to FIGS. 87-88B, the cartridge 2010 can comprise a plurality of staple cavities 2022 within cartridge body 2012, wherein cavities 2022 may comprise openings in surfaces 2018a-c of cartridge deck 2014. A staple can be positioned within each staple cavity 2022. For example, staples 2024a-c can be positioned within cavities 2022 and can be supported by staple drivers 2026a-c within cartridge body 2012. A sled and/or firing member, for example, can be advanced through the staple cartridge 2010 to lift the staple drivers 2026a-c upwardly within the staple cavities 2022 and eject the staples 2024a-c from cavities 2022 through the openings in the surfaces 2018a-c, respectively. The staples 2024a-c may be formed by advancing the staples 2024a-c against corresponding forming pockets 2032 defined in the anvil 2030 while the anvil 2030 is in the closed position.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Pat. No. 8,733,613, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety.

Figure 88A:
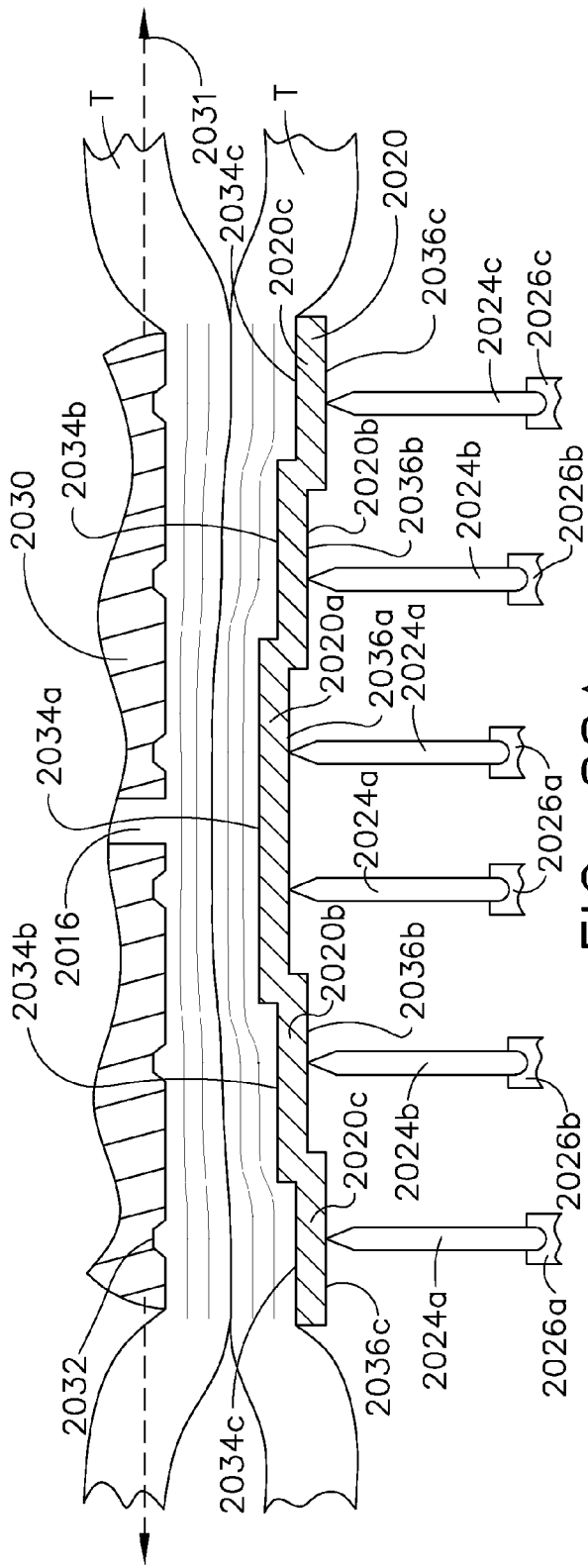
FIG. 88A is a cross-sectional view of the staple cartridge and the tissue thickness compensator of FIG. 87 showing unformed staples supported by staple drivers.

Referring again to FIGS. 87-88B, the tissue thickness compensator 2020 may include a plurality of portions, such as portions 2020a-c (See FIG. 87) which can be captured by staples 2024a-c, respectively. Portions 2020a-c, as illustrated in FIG. 88A, can be laterally offset from each other. For example, portions 2020b can be laterally offset from portions 2020a in a direction away from slot 2016 and portions 2020c can be laterally offset from portions 2020b also in a direction away from slot 2016. Furthermore, Portions 2020a-c, as illustrated in FIG. 88A, may include deck contacting surfaces 2036a-c, wherein compensator 2020 can be positioned against cartridge deck 2014 such that deck contacting surfaces 2036a-c may be removably positioned against or adjacent surfaces 2018a-c of deck 2014, respectively. Similar to surfaces 2018a-c, the deck contacting surfaces 2036a-c can be vertically offset from each other. For example, as illustrated in FIG. 88A, surfaces 2036a-c may each lie, or at least substantially lie, in a separate plane, wherein the planes of surfaces 2036a-c can be vertically offset from each other. In other words, surface 2036a may lie in a first plane, surface 2036b may lie in a second plane, and surface 2036c may lie in a third plane, wherein the first plane is closer than the second plane to a datum and the second plane is closer than the third plane to a datum such as, for example, datum 2031 at anvil 2030. As illustrated in FIG. 88A, datum 2031 may comprise a plane that passes through anvil 2030 when anvil 2030 is in the closed position, wherein datum 2031 may be parallel, or substantially parallel, to surfaces 2036a-c.

Further to the above, as illustrated in FIG. 88A, the distance between the planes of surfaces 2036a and 2036b can be the same, or at least substantially the same as the distance between the planes of surfaces 2036b and 2036c. Alternatively, the distance between the planes of surfaces 2036a and 2036b can be different from the distance between the planes of surfaces 2036b and 2036c. For example, the distance between the planes of surfaces 2036a and 2036b can be smaller than the distance between the planes of surfaces 2036b and 2036c.

Referring again to FIGS. 87-88B, portions 2020a-c may comprise tissue contacting surfaces 2034a-c which can be positioned against or adjacent tissue T. Similar to surfaces 2018a-c, as illustrated in FIG. 88A, the tissue contacting surfaces 2034a-c may be vertically offset from each other. For example, as illustrated in FIG. 88A, surfaces 2034a-c may each lie, or at least substantially lie, in a separate plane, wherein the planes of surfaces 2034a-c can be vertically offset from each other. In other words, surface 2034a may lie in a first plane, surface 2034b may lie in a second plane, and surface 2034c may lie in a third plane, wherein the first plane is closer than the second plane to a datum and the second plane is closer than the third plane to datum 2031, wherein datum 2031 may be parallel, or substantially parallel, to surfaces 2036a-c.

Further to the above, the distance between the planes of surfaces 2034a and 2034b can be the same, or at least substantially the same as the distance between the planes of surfaces 2034b and 2034c. Alternatively, the distance between the planes of surfaces 2034a and 2034b can be different from the distance between the planes of surfaces 2034b and 2034c. For example, the distance between the planes of surfaces 2034a and 2034b can be smaller than the distance between the planes of surfaces 2034b and 2034c.

Referring to FIGS. 88-90, portions 2020a-c of compensator 2020 may comprise a uniform, or substantially uniform uncompressed thickness. For example, as illustrated in the cross-sectional view in FIG. 88, portions 2020a may comprise a first uncompressed thickness between surfaces 2034a and surfaces 2036a and portions 2020b may comprise a second uncompressed thickness between surfaces 2034b and surfaces 2036b, wherein the first uncompressed thickness can be the same or substantially the same as the second uncompressed thickness. In addition, portions 2020c can comprise a third uncompressed thickness between surfaces 2034c and 2036c, wherein the third uncompressed thickness can be the same, or substantially the same as the first uncompressed thickness and/or the second uncompressed thickness.

Alternatively, compensator 2020 may comprise portions having different uncompressed thicknesses, wherein all or some of portions 2020a-c may comprise different uncompressed thicknesses. For example, as illustrated in FIG. 89, the third uncompressed thickness of portions 2020c may be greater than the second uncompressed thickness of portions 2020a while the first uncompressed thickness of portions 2020a may comprise the same, or substantially the same, uncompressed thickness as the second uncompressed thickness of portions 2020b. Under certain circumstances, the second uncompressed thickness can be greater than the first uncompressed thickness and the third uncompressed thickness can be greater than the second uncompressed thickness thereby forming a thickness gradient. Accordingly, compensator 2020 may comprise a thickness gradient, wherein the uncompressed thickness of certain portions of compensator 2020 may depend on the relative position of these portions. For example, compensator 2020 may comprise central portions having a minimum uncompressed thickness, peripheral portions having a maximum uncompressed thickness, and intermediate portions having a medium uncompressed thickness. Alternatively, the central portions may comprise a maximum uncompressed thickness and the peripheral portions may comprise a minimum uncompressed thickness. The reader will appreciate that the thickness of portions 2020a-c and their relative positions within the compensator 2020 can be configured to provide a desired thickness compensation for the tissue T within the formed staples 2024a-c.

Figure 88B:
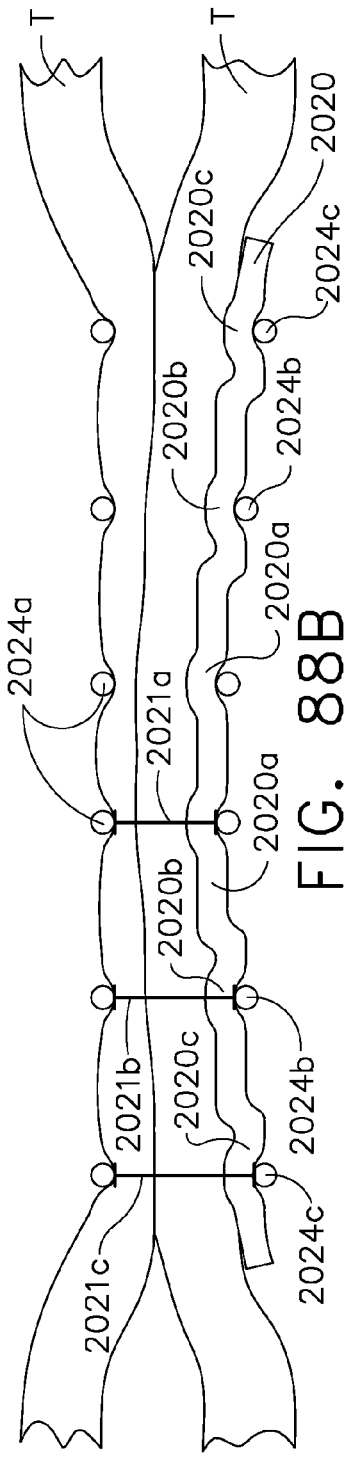
FIG. 88B is a cross-sectional view of the tissue thickness compensator of FIG. 87 captured by formed staples.

Further to the above, as illustrated in FIG. 88B, formed staples 2024a-c may capture tissue T and/or compensator 2020, wherein captured tissue T and captured compensator 2020 may compete for space within formed staples 2024a-c. Accordingly, tissue T and/or compensator 2020 can be compressed under compression forces applied thereto by formed staples 2024a-c which may depend, at least in part, on the formed heights of the staples 2024a-c, compressibility of tissue T, compressibility of compensator 2020, tissue T thickness, and/or compensator 2020 thickness. Accordingly, some or all of these parameters can be manipulated to yield a desired compression in the tissue T within the formed staples 2024a-c.

Further to the above, the compressibility of the tissue T may depend, at least in part, on the modulus of elasticity of the tissue T and the compressibility of compensator 2020 may depend, at least in part, on the modulus of elasticity of compensator 2020, wherein a greater modulus of elasticity may result in greater compressibility. For example, as illustrated in FIG. 88B, staples 2024a may capture corresponding portions 2020a of compensator 2020 and corresponding tissue T which may result in a competition for space between the portions 2020a and corresponding tissue T within the formed staples 2024a. In the example illustrated in FIG. 88B, the tissue T may comprise a greater modulus of elasticity than the corresponding portions 2020a. Accordingly, formed staples 2024a may compress tissue T to a greater degree than corresponding portions 2020a. Furthermore, as described above and as illustrated in FIG. 88B, the formed height 2021a of staples 2024a may be shorter than the formed height 2021b of staples 2024b and the formed height 2021b may be shorter than the formed height 2021c of staples 2024c. Accordingly, the space available within formed staples 2024a may be less than the space available within formed staples 2024b which may be less than the space available within formed staples 2024c. In result, the tissue T within formed staples 2024a may be compressed to a greater degree than the tissue T within formed staples 2024b which may be compressed to a greater degree than the tissue T within formed staples 2024c.

Further to the above, portions 2020a-c of compensator 2020 may comprise different moduli of elasticity which may result in different degrees of compressibility across compensator 2020. For example, portions 2020a may comprise a greater modulus of elasticity than the portions 2020b and the portions 2020b may comprise a greater modulus of elasticity than the portions 2020c. In result, a modulus of elasticity gradient may exist across the compensator 2020 wherein a central portion, for example one of the portions 2020a, may comprise a greater modulus of elasticity than a peripheral portion, for example one of the portions 2020c. In addition, an intermediate portion, for example one of the portions 2020b, may comprise a greater modulus of elasticity than the peripheral portion and a lesser modulus of elasticity than the central portion. Accordingly, tissue T within the formed staples 2024a-c may be configured to experience a desirable compression force by manipulating the modulus of elasticity of the corresponding portions 2020a-c.

Referring again to FIG. 88B, as described above, the compression forces experienced by the tissue T and the compensator 2020 may depend, at least in part, on the heights 2021a-c of the formed staples 2024a-c which may determine the total space available within formed staples 2024a-c for the tissue T and the corresponding portions 2020a-c of compensator 2020 to compete therein. For example, as illustrated in FIG. 88B, the space available within formed staples 2024c may be greater than the space available within formed staples 2024b and the space available within formed staples 2024b may be greater than the space available within formed staples 2024a. In result, tissue T and corresponding portions 2020a may experience greater compression forces within staples 2024a than that experienced by tissue T and corresponding portions 2020b within formed staples 2024b. In addition, tissue T and corresponding portions 2020b may experience greater compression forces within formed staples 2024b than that experienced by tissue T and corresponding portions 2020c within formed staples 2024c. Accordingly, a tissue compression gradient can be established, wherein tissue T within formed staples 2024a may experience a greater compression than tissue T within formed staples 2024b and tissue T within staples 2024b may experience a greater compression than tissue T within staples 2024c. Other embodiments are envisioned in which a tissue thickness compensator and formed staples can be made to induce a suitable compression through the tissue T within the formed staples.

Further to the above, referring to FIG. 89, a tissue thickness compensator 2020' may comprise a plurality of portions 2020'a-c. The compression forces experienced by tissue T and the compensator 2020' upon being captured by staples 2024a-c can depend, at least in part, upon the thickness of portions 2020'a-c of compensator 2020'. The portions 2020'a-c may comprise different uncompressed thicknesses. For example, as illustrated in FIG. 89, the portions 2020'c may comprise a greater uncompressed thickness than the portions 2020'a and 2020'b which may result in a greater compression in the tissue T captured by staples 2024c than the tissue T captured by staples 2024a and 2024b. Under certain circumstances, the compression forces experienced by captured tissue T and captured compensator 2020' may be directly proportional to the thickness of compensator 2020'.

Referring now to FIG. 90, a tissue thickness compensator composite such as, for example, composite 2060 can comprise multiple tissue thickness compensators. For example, composite 2060 may comprise tissue thickness compensator 2020 and tissue thickness compensator 2080, wherein compensator 2080 can be positioned, at least in part, adjacent or against compensator 2020. For example, compensator 2080 can be selectively positioned over certain portions of compensator 2020 to provide, for example, a desirable thickness and/or compliance. As illustrated in FIG. 90, compensator 2080 may comprise portions 2080c which can be positioned over, for example, portions 2020c of compensator 2020.

Further to the above, compensator 2080 and compensator 2020 can be joined together, for example, by an adhesive. Other attachment means for attaching compensator 2020 to compensator 2080 are contemplated within the scope of this disclosure. Similar to compensator 2020, the portions of compensator 2080 may comprise various thicknesses, moduli of elasticity, and/or relative spatial arrangements. Furthermore, the portions of compensator 2080 and the corresponding portions of compensator 2020 may comprise the same or different uncompressed thickness and/or moduli of elasticity. For example, portions 2080c may comprise a higher modulus of elasticity than portions 2020c to provide and may provide a compliant tissue contacting surface on a peripheral region of composite 2080.

Further to the above, compensator 2020 and/or compensator 2080 may be comprised of biocompatible materials. In addition, compensator 2020 and/or compensator 2080 may be comprised of biodegradable materials such as, for example, PGA, PCL, PLLA, and/or combinations thereof, for example. Compensator 2020 and compensator 2080 may be comprised of the same material or different materials to yield a desired localized compressibility across composite 2080.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Various embodiments described herein are described in the context of staples removably stored within staple cartridges for use with surgical stapling instruments. In some circumstances, staples can include wires which are deformed when they contact an anvil of the surgical stapler. Such wires can be comprised of metal, such as stainless steel, for example, and/or any other suitable material. Such embodiments, and the teachings thereof, can be applied to embodiments which include fasteners removably stored with fastener cartridges for use with any suitable fastening instrument.

Various embodiments described herein are described in the context of tissue thickness compensators attached to, and/or for use with, staple cartridges and/or fastener cartridges. Such tissue thickness compensators can be utilized to compensate for variations in tissue thickness from one end of a staple cartridge to another, or for variations in tissue thickness captured within one staple, or fastener, as compared to another. Such tissue thickness compensators can also be utilized to compensate for variations in tissue thickness from one side of a staple cartridge to another. Such embodiments, and the teachings thereof, can be applied to embodiments which include a layer, or layers, of material attached to, and/or for use with, staple cartridges and/or fastener cartridges. A layer can include buttress material.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An end effector assembly for use with a surgical instrument, the end effector assembly comprising:
   an anvil;
   a fastener cartridge comprising a plurality of fastener cavities;
   a plurality of fasteners, wherein each said fastener is removably positioned in one of said fastener cavities;
   a piece of buttress material releasably secured intermediate said anvil and said fastener cartridge;
   a connector, wherein said connector secures said piece of buttress material intermediate said anvil and said fastener cartridge at a location, and wherein the location is distal to at least one said fastener cavity; and
   an actuator configured to overcome said connector when actuated, wherein said actuator overcomes said connector prior to the removal of said fasteners from said fastener cavities, wherein said actuator comprises a slot, and wherein said slot comprises a release stop.

2. The end effector assembly of claim 1, wherein said actuator breaks said connector when actuated.

3. The end effector assembly of claim 2, wherein said piece of buttress material is released from said fastener cartridge when said connector breaks.

4. The end effector assembly of claim 1, wherein said actuator dislodges said connector when actuated to release said piece of buttress material from said fastener cartridge.

5. The end effector assembly of claim 1, comprising a firing element configured to move along said slot and configured to push through said release stop, wherein said firing element is configured to shift said actuator when said firing element pushes against said release stop.

6. The end effector assembly of claim 5, wherein said slot comprises a first width, wherein said release stop comprises a second width that is narrower than said first width, and wherein said firing element is configured to widen said second width to pass through said release stop.

7. The end effector assembly of claim 5, wherein said release stop comprises a breakable portion, and wherein said firing element breaks said breakable portion to pass through said release stop.

8. The end effector assembly of claim 5, comprising a hard stop, wherein said hard stop blocks distal movement of said actuator past said hard stop.

9. The end effector assembly of claim 1, wherein said connector comprises braided fibers.

10. The end effector assembly of claim 1, wherein said actuator extends through at least a portion of said anvil.

11. The end effector assembly of claim 1, further comprising a second piece of buttress material releasably secured to said anvil.

12. An end effector assembly for use with a surgical instrument, the end effector assembly comprising:
    an anvil;
    a fastener cartridge comprising a plurality of fastener cavities;
    a plurality of fasteners, wherein each said fastener is removably positioned in one of said fastener cavities;
    a piece of buttress material releasably secured intermediate said anvil and said fastener cartridge;
    a connector, wherein said connector secures said piece of buttress material intermediate said anvil and said fastener cartridge at a location, and wherein the location is distal to at least one said fastener cavity; and
    an actuator configured to overcome said connector when actuated, wherein said actuator overcomes said connector prior to the removal of said fasteners from said fastener cavities, wherein said actuator surrounds at least a portion of said fastener cartridge.

13. An end effector assembly for use with a surgical instrument, the end effector assembly comprising:
    an anvil;
    a fastener cartridge comprising a fastener cavity;
    a fastener removably positioned in said fastener cavity;
    a piece of buttress material releasably secured intermediate said anvil and said fastener cartridge;
    a connector, wherein said connector secures said piece of buttress material to one of said anvil or said fastener cartridge, and wherein said connector is positioned distal to said fastener cavity;
    an actuator configured to overcome said connector when actuated, wherein said actuator extends past said fastener in said fastener cavity, wherein said actuator is actuated proximal to said fastener cavity, and wherein said actuator comprises a slot; and
    a firing element configured to lift said fastener toward said anvil, wherein said firing element is configured to translate along said slot.

14. The end effector assembly of claim 13, wherein said slot comprises a release stop, wherein said firing element is configured to push through said release stop when translating along said slot, and wherein said firing element is configured to shift said actuator when said firing element pushes against said release stop.

15. The end effector assembly of claim 14, wherein said release stop comprises a breakable portion, and wherein said firing element breaks said breakable portion to pass through said release stop.

16. The end effector assembly of claim 14, comprising a hard stop, wherein said hard stop blocks distal movement of said actuator past said hard stop.

17. The end effector assembly of claim 13, further comprising a second piece of buttress material releasably secured to said anvil.

18. An end effector assembly for use with a surgical instrument, the end effector assembly comprising:
    an anvil;
    a fastener cartridge comprising a fastener cavity;
    a fastener removably positioned in said fastener cavity;
    a piece of buttress material releasably secured intermediate said anvil and said fastener cartridge;
    a connector, wherein said connector secures said piece of buttress material to one of said anvil or said fastener cartridge, and wherein said connector is positioned distal to said fastener cavity; and an actuator configured to overcome said connector when actuated, wherein said actuator extends past said fastener in said fastener cavity, wherein said actuator is actuated proximal to said fastener cavity, wherein said actuator comprises a distal cutting edge, and wherein said distal cutting edge cuts said connector when said actuator is actuated.

19. The end effector assembly of claim 18, wherein said actuator overcomes said connector prior to the removal of said fastener from said fastener cavity.

20. An end effector assembly, comprising:
an anvil;
a fastener cartridge comprising a fastener cavity;
a fastener removably positioned in said fastener cavity;
a piece of buttress material releasably secured intermediate said anvil and said fastener cartridge;
a connector, wherein said connector secures said piece of buttress material to one of said anvil or said fastener cartridge, and wherein said connector is positioned distal to said fastener cavity;
a firing element configured to lift said fastener toward said anvil during a firing stroke;
an actuator configured to overcome said connector when actuated, wherein said firing element is configured to actuate said actuator proximal to said fastener cavity, and wherein said actuator is configured to translate distally when actuated by said firing element.

* * * * *